United States Patent

Kato et al.

[11] Patent Number: 5,591,849
[45] Date of Patent: Jan. 7, 1997

[54] SPIRO[NAPHTHALENE-2(1H),2'-PIPERIDINE] AND THEIR USE

[75] Inventors: Kaneyoshi Kato, Kawanishi; Jun Terauchi; Yasuo Nagai, both of Osaka, all of Japan

[73] Assignee: Takeda Chemical Industries, Ltd., Osaka, Japan

[21] Appl. No.: 398,290

[22] Filed: Mar. 3, 1995

[30] Foreign Application Priority Data

Mar. 4, 1994 [JP] Japan .................. 6-034421

[51] Int. Cl.$^6$ .......... C07D 221/20; C07D 401/06; C07D 413/06; A61K 31/445
[52] U.S. Cl. .............. 544/70; 544/230; 546/17; 514/252; 514/278; 514/235.2; 540/543
[58] Field of Search ............ 544/230, 70; 514/252, 514/278, 235.2; 546/17

[56] References Cited

U.S. PATENT DOCUMENTS 3,903,087  9/1975  Kato et al. .................. 260/268
5,206,240  4/1993  Baldwin et al. .................. 514/231.5

FOREIGN PATENT DOCUMENTS 2356999  5/1974  Germany .

OTHER PUBLICATIONS

Crooks et al., Journal of Medicinal Chem., vol. 21, No. 6 (1978) 585–587. Month of publication not provided.
Crooks et al., Journal of Chemical Society Perkin I (1979) 2719–2726. Month of publication not provided.
Chemical Abstracts, vol. 80, No. 11 (Mar. 1974) (p. 357) 59915g.
Chemical Abstracts, vol. 82, No. 9 (Mar. 1975) (p. 578) 57732n.
Chemical Abstracts, vol. 87, No. 9 (Aug. 1977) (pp. 559–560) 68416s.
Chemical Abstracts, vol. 94, No. 17 (Apr. 1981) (p. 743) 139592d.
Chemical Abstracts, vol. 104, No. 9 (Mar. 1986) (p. 668) 68709j.

Primary Examiner—Mukund J. Shah
Assistant Examiner—King Lit Wong
Attorney, Agent, or Firm—Fitzpatrick, Cella, Harper & Scinto

[57] ABSTRACT

A spiro compound represented by the formula:

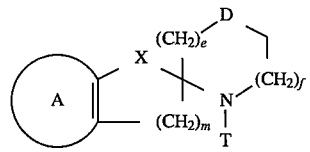

wherein ring A represents an optionally substituted aromatic ring; T represents an optionally substituted hydrogen atom or an optionally substituted hydrocarbon group; X represents —$CH_2$—, —CO— or —CH(OH)—; D represents —$CH_2$—, —O— or —NR— wherein R is a hydrogen atom or an optionally substituted hydrocarbon group and m, e and f independently represent an integer from 1 to 3, or a salt thereof. The spiro compound inhibits monoamine uptake, monoamine oxidase B and/or Ca ion uptake, and is a prophylactic and therapeutic drug for a central nervous diseases.

10 Claims, No Drawings

SPIRO[NAPHTHALENE-2(1H),2'-PIPERIDINE] AND THEIR USE

BACK GROUND OF THE INVENTION

1. Field of the Invention

The present invention relates to a new spiroamine derivative that promotes the normalization or activation of neuro transmitter, and is useful in preventing and treating nervous diseases such as a neuropathy and dysmnesia. The present invention relate to a method of producting the spiroamine, and a pharmaceutical use thereof.

2. Description of the Prior Art

It is well-known that substituted 2-aminotetralin derivatives act on an intracerebral monoamine nervous system and exhibit various effects on the central nervous system, because their stereostructures are similar to those of monoamines such as dopamine, norepinephrine and serotonin. Also, the "Journal of Medicinal Chemistry, Vol. 21, No. 6, pp. 585–587 (1978)" describes a compound represented by the formula:

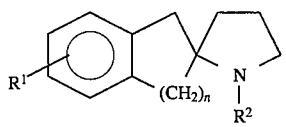

wherein $R^1$ represents H, OMe or OH; $R^2$ represents H, $CH_2CH_2CO_2Me$ or Me; n represents 1 or 2. The "Journal of Chemical Society Perkin Transaction I, pp. 2719–2726 (1979)" describes compounds represented by the formulas:

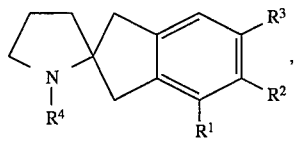

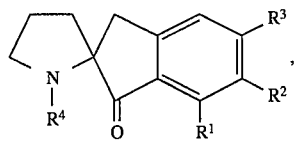

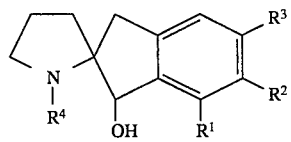

wherein $R^1$ represents H or OMe; $R^2$ represents H, OH or OMe; $R^3$ represents H, OH or OMe; $R^4$ represents H, COPh or $CH_2Ph$. These compounds have been reported as possessing a sedative or anti-reserpine activity. However, there is no report concerning compounds having a spiro moiety comprising a 6-membered or higher ring such as piperidine, or their pharmacological action.

SUMMARY OF THE INVENTION

There is strong need for the development of a new compound that has a chemical structure quite different from those of such conventional compounds and exhibits excellent action on a nervous system.

As a result of much research and study, the present inventors succeeded in synthesizing a new spiroamine derivative which shows excellent inhibition of a monoamine uptake, calcium ion ($Ca^{2+}$) uptake and/or monoamine-oxidase B (MAO-B) in a nervous system, and has very low toxicity.

DETAILED DESCRIPTION OF THE PREFERRED EMBODIMENTS

The present invention relates to:

(1) a spiroamine derivative (I) represented by the formula:

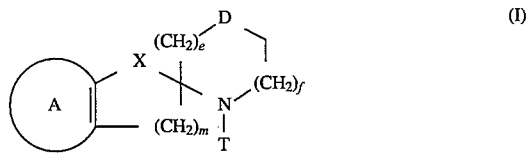

wherein ring A represents an optionally substituted aromatic ring; T represents a hydrogen atom or an optionally substituted hydrocarbon group; X represents $CH_2$—, —CO— or —CH(OH)—; D represents —$CH_2$—, —O— or —NR— wherein R is a hydrogen atom or an optionally substituted hydrocarbon group; and m, e and f independently represent an integer of 1 to 3, or a salt thereof which is structurally characterized by a spiro moiety comprising a 6-membered or higher ring. The present invention also relates to (2) a compound as defined hereinbelow, which is a compound of the formula:

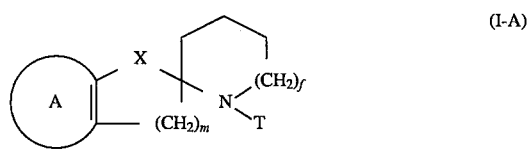

wherein all symbols are as defined hereinabove.

Preferably in Formulae (I) and (I-A), the substituent on the aromatic ring is a halogen atom or a group which may be bonded through an atom selected from a carbon, nitrogen, oxygen and sulfur atom.

Preferably in Formulae (I) and (I-A), the ring A is an aromatic ring which may be substituted by 1 to 3 substituents selected from the group consisting of (i) a halogen atom, (ii) a $C_{1-6}$ alkyl group, (iii) a $C_{1-6}$ alkoxy group, (iv) a nitro group, (v) a cyano group, (vi) a hydroxyl group, (vii) an amino, mono-$C_{1-6}$ alkylamino, di-$C_{1-6}$ alkylamino or benzylamino group, (viii) a $C_{1-6}$ alkyl-carbonyl group, (ix) a pyrrolidino, piperidino, morpholino, 2-pyridon-1-yl or 3-pyridon-1-yl group and (x) a carbamoyl, mono-$C_{1-6}$ alkylcarbamoyl or di-$C_{1-6}$ alkylcarbamoyl group.

Preferably in Formulae (I) and (I-A), the ring A is an aromatic ring which may be substituted by 1 to 3 substituents selected from the group consisting of a halogen atom, a $C_{1-6}$ alkoxy group and a hydroxyl group.

Preferably in Formulae (I) and (I-A), the ring A is an aromatic ring which may be substituted by 1 or 2 substituents selected from a group represented by the formula:

—O—$(CH_2)_p$—Q wherein p represents an integer from 0 to 4, and Q represents an optionally substituted aryl group or an optionally substituted heterocyclic group, Preferably in Formulae (I) and (I-A), wherein Q is more preferably a phenyl group which may be substituted by 1 to 3 substituents selected from the group consisting of a halogen atom, a $C_{1-6}$ alkyl group and a $C_{1-6}$ alkoxy group, Preferably in Formulae (I) and (I-A), the aromatic ring is a benzene ring.

Preferably in Formulae (I) and (I-A), the hydrocarbon group represented by T is a $C_{1-10}$ alkyl, $C_{2-10}$ alkenyl or $C_{2-10}$ alkynyl group.

Preferably in Formulae (I) and (I-A), T is a group represented by the formula:

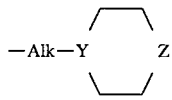

wherein Alk represents a $C_{1-10}$ alkylene group which may be substituted by an oxo group; Y represents a nitrogen atom or —CH<; and Z represents an oxygen atom, >CH-$(CH_2)_q$—W or >N—$(CH_2)_q$—W (q represents an integer from 0 to 4 and W represents a hydrogen atom, an optionally substituted aryl group or an optionally substituted heterocyclic group). Preferably in Formulae (I) and (I-A), wherein W is more preferably (i) a hydrogen atom or (ii) a phenyl group which may be substituted by 1 to 3 substituents selected from the group consisting of a halogen atom, a $C_{1-6}$ alkyl group and a $C_{1-6}$ alkoxy group.

Preferably in Formulae (I) and (I-A), T is a hydrogen atom.

Preferably in Formulae (I) and (I-A), X is a methylene group.

Preferably in Formulae (I) and (I-A), each of e and f is 1.

Preferably in Formulae (I) and (I-A), m is 2 and f is 1.

The present invention also relates to a process for producing a compound represented by the formula:

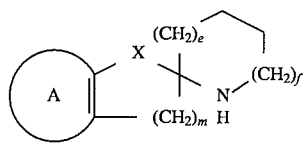

(I-a)

wherein all symbols are as defined above, or a salt thereof, which comprises subjecting to cyclization reaction a compound represented by the formula:

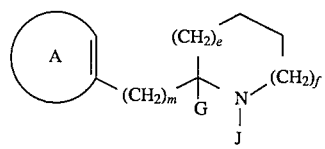

(II)

wherein G represents a cyano, carboxyl, $C_{1-6}$ alkoxy-carbonyl or benzyloxycarbonyl group; and J represents an amino-protecting group; or a salt thereof followed by hydrolysis and deprotection, with reduction as necessary.

The present invention relates further to a process for producing a compound represented by the formula:

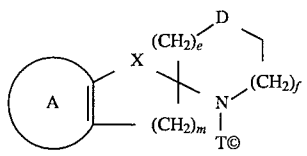

(I-b)

wherein T' is the same meaning as defined hereinafter, and the other symbols are as defined above, or a salt thereof, which comprises reacting the compound (I-a) or a salt thereof with a compound represented by the formula:

T'—L wherein T' represents an optionally substituted hydrocarbon group, L represents a leaving group, and so on.

With respect to the above formulas, "ring A" is an optionally substituted aromatic ring. The "aromatic ring" is exemplified by an aromatic hydrocarbon ring and an aromatic heterocyclic ring and so on. Examples of "an aromatic hydrocarbon" respresented by "ring A" include a monocyclic or condensed polycyclic aromatic hydrocarbon group having 6 to 14 carbon atoms, such as a benzene, indene, naphthalene and anthracene ring. Preferable examples are:

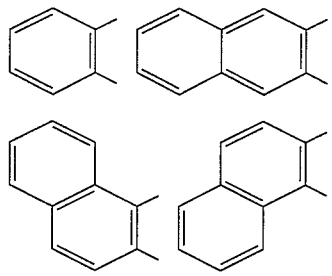

and so on. Most preferably, the alomatic ring is a benzene ring.

The "aromatic heterocyclic ring" represented by "ring A" include a 5- or 6-membered monocyclic aromatic heterocyclic ring containing 1 or 2 kinds of hetero atoms, preferably 1 or 2 hetero atoms selected from a nitrogen, sulfur and oxygen atom in addition to carbon atoms, or a condensed polycyclic aromatic heterocyclic ring formed by the monocyclic aromatic heterocyclic ring with 1 or 2 benzene rings such as pyridine, pyrazine, pyrimidine, pyridazine, pyrrole, imidazole, pyrazole, thiophene, furan, thiazole, isothiazole, oxazole, isoxazole, quinoline, isoquinoline, indole and isoindole ring. Preferable examples are a 5- or 6-membered monocyclic aromatic heterocyclic ring containing one atom of nitrogen, sulfur or oxygen, or a condensed polycyclic aromatic heterocyclic ring formed by the monocyclic aromatic heterocyclic ring with one benzene ring, such as the following:

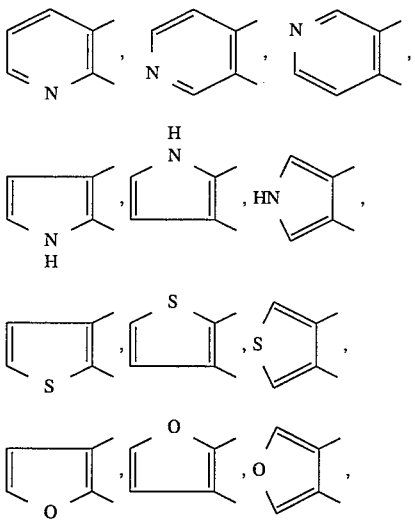

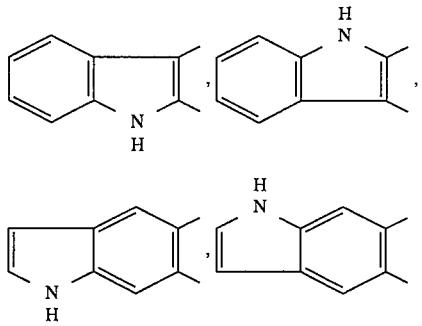

and so on. Specifically, a thiophene, pyrrole and indole ring are preferred. A thiophene and indole ring such as the following

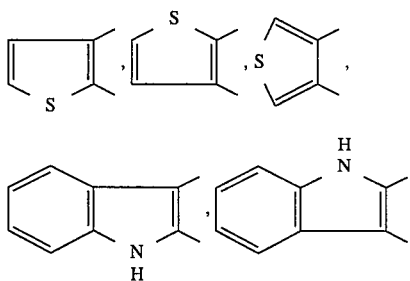

are commonly used.

The substituents that "aromatic ring" represented by "ring A" may have include a halogen atom and a group bonded through an atom selected from a carbon, nitrogen, oxygen and sulfur atom. Preferable examples are a halogen atom, an optionally substituted alkyl group, an optionally halogenated alkoxy group, an optionally halogenated alkylthio group, a $C_{2-6}$ alkenyl group (e.g., vinyl, allyl, 2-butenyl, isopropenyl, 2-pentenyl, 3-pentenyl, 4-pentenyl, 2-hexenyl, 3-hexenyl, 4-hexenyl, 5-hexenyl), a $C_{2-6}$ alkynyl group (e.g., propargyl, ethynyl, 1-hexynyl, 2-hexynyl, 3-hexynyl, 4-hexynyl), a $C_{3-8}$ cycloalkyl group (e.g., cyclopropyl, cyclobutyl, cyclopentyl, cyclohexyl), a nitro group, a cyano group, a sulfo group, a hydroxyl group, an amino group, a mono- or di-$C_{1-6}$ alkylamino group (e.g., methylamino, ethylamino, propylamino, dimethylamino, diethylamino), a $C_{7-16}$ aralkylamino group (e.g., benzylamino), a cyclic amino group that may have an oxo group (e.g., pyrrolidino, piperidino, morpholino, 2-pyridon-1-yl, 3-pyridon-1-yl), a mercapto group, a carbamoyl group, a mono- or di-$C_{1-6}$ alkyl-carbamoyl group (e.g., methylcarbamoyl, ethylcarbamoyl, dimethylcarbamoyl, diethylcarbamoyl), a $C_{6-14}$ aryl-carbamoyl group (e.g., phenylcarbamoyl), a $C_{1-6}$ alkoxy-carbonyl group (e.g., methoxycarbonyl, ethoxycarbonyl, propoxycarbonyl, isopropoxycarbonyl, butoxycarbonyl), a $C_{1-6}$ alkylsulfonylamino group (e.g., methylsulfonylamino, ethylsulfonylamino, propylsulfonylamino, butylsulfonylamino), a $C_{7-16}$ aralkyl group (e.g., benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl), a $C_{6-14}$ aryl group (e.g., phenyl, tolyl, xylyl, 1-naphthyl, 2-naphthyl, biphenyl, 2-indenyl, 2-anthryl), a heterocyclic group, a formyl group, a carboxyl group, a $C_{1-6}$ alkyl-carbonyl group (e.g., acetyl, propionyl, butyryl, valeryl), a $C_{2-6}$ alkenyl-carbonyl group (e.g., acryloyl), a $C_{2-6}$ -alkynyl-carbonyl group (e.g., propiolyl), a $C_{6-14}$ aryl-carbonyl group (e.g., benzoyl), a nicotinoyl group, a $C_{1-6}$ alkylsulfonyl group (e.g., methylsulfonyl, ethylsulfonyl, propylsulfonyl), a $C_{6-14}$ arylsulfonyl group (e.g., benzenesulfonyl), a $C_{1-7}$ acylamino group (e.g., formylamino, acetylamino, propionylamino, butyrylamino, benzoylamino), a $C_{1-3}$ acyloxy group (e.g., formyloxy, acetoxy, propionyloxy) and a $C_{6-14}$ aryloxy group (e.g., phenoxy). These substituents may be present at any possible positions on the aromatic ring, the number of substituents being 1 to 3. Two or more of such substituents may be the same or different. Ring A is also preferably substituted by only one methylenedioxy or ethylenedioxy group.

The "halogen atom" which may be substituted on the "aromatic ring" as substituents include a fluorine, chlorine, bromine and iodine, with preference given to fluorine, chlorine and bromine.

The alkyl group of the "optionally substituted alkyl group" which may be substituted on the "aromatic ring" as substituents include a $C_{1-6}$ alkyl group such as methyl, ethyl, propyl, isopropyl, butyl, isobutyl, sec-butyl, tert-butyl, pentyl, isopentyl, neopentyl and hexyl, and a $C_{1-4}$ alkyl group such as methyl, ethyl, propyl, isopropyl, butyl, isobutyl, sec-butyl and tert-butyl, are commonly used. These alkyl group may have 1 to 3 substituents selected from the group consisting of a hydroxyl group, an amino group, a carboxyl group, a nitro group, a mono- or di-$C_{1-6}$ alkylamino group (e.g., methylamino, ethylamino, dimethylamino, diethylamino), a $C_{1-6}$ alkyl-carbonyloxy group (e.g., acetoxy, ethylcarbonyloxy) and a halogen atom (e.g., fluorine, chlorine, bromine).

Preferable examples of the "optionally substituted alkyl group" which may be substituted on the "aromatic ring" as substituents include a $C_{1-6}$ alkyl group which may have 1 to 3 halogen atoms (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl), and a $C_{1-4}$ alkyl group which may have 1 to 3 halogen atoms (e.g., methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl) are commonly used.

The "optionally halogenated alkoxy group" which may be substituted on the "aromatic ring" as substituents include a $C_{1-6}$ alkoxy group which may be substituted by 1 to 3 substituents selected from the above-mentioned "halogen atom" such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy, with preference given to a $C_{1-4}$ alkoxy group such as methoxy, difluoromethoxy, trifluoromethoxy, ethoxy, 2,2,2-trifluoroethoxy, propoxy, isopropoxy, butoxy, 4,4,4-trifluorobutoxy, isobutoxy and sec-butoxy.

The "optionally halogenated alkylthio group" which may be substituted on the "aromatic ring" as substituents include a $C_{1-6}$ alkylthio group which may be substituted by 1 to 3 substituents selected from the above-mentioned "halogen atom" such as methylthio, difluoromethylthio, trifluoromethylthio, ethylthio, propylthio, isopropylthio, butylthio, 4,4,4-trifluorobutylthio, pentylthio and hexylthio, with preference given to a $C_{1-4}$ alkylthio group such as methylthio, difluoromethylthio, trifluoromethylthio, ethylthio, propylthio, isopropylthio, butylthio and 4,4,4-trifluorobutylthio.

In the description below, the expression "optionally halogenated" means "which may be substituted by 1 to 3 halogen atoms (e.g., fluorine, chlorine, bromine)."

The "heterocyclic group" which may be substituted on the "aromatic ring" as substituents include a 5- to 11-membered aromatic or non-aromatic heterocyclic group containing 1 to 3 hereto atoms selected from a nitrogen, sulfur and oxygen atom in addition to carbon atoms. Such groups include a 2-thienyl, 3-thienyl, 2-pyridyl, 3-pyridyl, 4-pyridyl, 2-furyl, 3-furyl, 2-quinolyl, 4-quinolyl, 8-quinolyl, 3-isoquinolyl, 4-isoquinolyl, pyrazinyl, 2-pyrimidinyl, 3-pyrrolyl, 1-imidazolyl, 2-imidazolyl, 1-pyrazolyl, 2-thiazolyl, 4-thiazolyl, 5-thiazolyl, 3-isothiazolyl, 4-isothiazolyl, 3-isoxazolyl, pyridazinyl, 1-pyrrolidinyl, 2-pyrrolidinyl, 3-pyrrolidinyl, 2-pyridon-1-yl, 3-pyridon-1-yl, 1-imidazolidinyl, 2-imidazolidinyl, 3-imidazolidinyl, piperidino, 2-piperidyl, 3-piperidyl, 4-piperidyl, 2-morpholinyl, 3-morpholinyl, 4-morpholinyl, 1-piperazinyl, 2-piperazinyl, 1-isoindolyl, 2-isoindolyl, 1-indolyl, 1-phthalimide and 2,3,4,5-tetrahydro-(1H)-3-benzoazepinyl group. Of these heterocyclic groups, a 5- or 6-membered heterocyclic group containing 1 to 3 hetero atoms selected from a nitrogen, sulfur and oxygen atom (e.g., 2-thienyl, 3-thienyl, 2-pyridyl, 3-pyridyl, 4-pyridyl, 2-furyl, 3-furyl, 1-pyrrolidinyl, 2-pyrrolidinyl, 3-pyrrolidinyl, 1-piperazinyl, 2-piperazinyl) are preferred.

In the substituents which may be substituted on the "aromatic ring" represented by "ring A", a substituent including an aromatic ring may have a halogen atom (e.g., fluorine, chlorine, bromine), a $C_{1-6}$ alkyl group (e.g., methyl, ethyl, propyl, isopropyl), a $C_{3-8}$ cycloalkyl group (e.g., cyclopropyl, cyclobutyl, cyclopentyl, cyclohexyl), a $C_{1-6}$ alkoxy group (e.g., methoxy, ethoxy, propoxy, isopropoxy), a nitro group, a cyano group, a sulfo group, a hydroxyl group, an amino group, a mono- or di-$C_{1-6}$ alkylamino group (e.g., methylamino, ethylamino, dimethylamino, diethylamino), a carbamoyl group, a mono- or di-$C_{1-6}$ alkylcarbamoyl group (e.g., methylcarbamoyl, ethylcarbamoyl, dimethylcarbamoyl, diethylcarbamoyl), a phenyl group, a benzyl group, and a $C_{1-6}$ alkyl-carbonyl group (e.g., acetyl, propionyl, butyryl, valeryl). These substituents may be presented at any possible positions on the aromatic ring, and may be the same or different, the number of substituents being 1 to 3. Preferable substituents include a halogen atom (e.g., fluorine, chlorine, bromine), a $C_{1-6}$ alkyl group (e.g., methyl, ethyl, propyl, isopropyl), a $C_{1-6}$ alkoxy group (e.g., methoxy, ethoxy, propoxy, isopropoxy), a cyano group, a hydroxyl group and an amino group.

"Ring A" may have 1 or 2 substituents at any possible positions thereon, preferably one substituent represented by the formula:

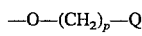

$$-O-(CH_2)_p-Q$$

wherein p represents an integer from 0 to 4; Q represents an optionally substituted aryl group or an optionally substituted heterocyclic group.

The "aryl group" represented by "Q" is exemplified by a $C_{6-14}$ aryl group, such as phenyl, tolyl, xylyl, 1-naphthyl, 2-naphthyl, biphenyl, 2-indenyl and 2-anthryl, with preference given to a phenyl group.

The "heterocyclic group" represented by "Q" is exemplified by the same heterocyclic groups as those which may be substituted on the "aromatic ring" represented by "ring A" as substituents, with preference given to a 5- or 6-membered heterocyclic group containing 1 to 3 hetero atoms selected from a nitrogen, sulfur and oxygen atom (e.g., 2-thienyl, 3-thienyl, 2-pyridyl, 3-pyridyl, 4-pyridyl, 2-furyl, 3-furyl, pyrazinyl, 2-pyrimidinyl, 3-pyrrolyl, 1-imidazolyl, 2-imidazolyl, 1-pyrazolyl, 2-thiazolyl, 5-thiazolyl, 3-isothiazolyl, 3-isoxazolyl, 3-pyridazinyl).

Preferable examples of "Q" is an optionally substituted phenyl group.

Substituents that the "aryl group" (particularly phenyl group) or "heterocyclic group" represented by "Q" may have include a halogen atom (e.g., fluorine, chlorine, bromine), a $C_{1-6}$ alkyl group (e.g., methyl, ethyl, propyl, isopropyl, butyl, isobutyl, sec-butyl, tert-butyl, pentyl, isopentyl, neopentyl, hexyl), a $C_{3-8}$ cycloalkyl group (e.g., cyclopropyl, cyclobutyl, cyclopentyl, cyclohexyl), a $C_{1-6}$ alkoxy group (e.g., methoxy, ethoxy, propoxy, isopropoxy), a nitro group, a cyano group, a sulfonyl group, a hydroxyl group, an amino group, a mono- or di-$C_{1-6}$ alkylamino group (e.g., methylamino, ethylamino, dimethylamino, diethylamino), a carbamoyl group, a mono- or di-$C_{1-6}$ alkylcarbamoyl group (e.g., methylcarbamoyl, ethylcarbamoyl, dimethylcarbamoyl, diethylcarbamoyl), a phenyl group, a benzyl group and a $C_{1-6}$ alkyl-carbonyl group (e.g., acetyl, propionyl, butyryl, valeryl). These substituents may be present at any possible positions on the "aryl or heteroyclic group" and may be the same or different, and the number of substituents being 1 to 3.

"Ring A" is preferably a benzene or thiophene ring, and so on. These rings may have the substituents listed in the following items A-(1), A-(2) and A-(3) at any possible positions thereon.

A-(1): 1 to 3 substituents selected from the group consisting of a halogen atom (e.g., fluorine, chlorine, bromine), a $C_{1-6}$ alkyl group (e.g., methyl, ethyl, propyl, isopropyl, butyl, isobutyl, sec-butyl, tert-butyl, pentyl, isopentyl, neopentyl, hexyl), a $C_{1-6}$ alkoxy group (e.g., methoxy, ethoxy, propoxy, isopropoxy, trifluoromethoxy), a nitro group, a cyano group, a hydroxyl group, an amino group, a mono- or di-$C_{1-6}$ alkylamino group (e.g., methylamino, ethylamino, dimethylamino, diethylamino), a benzylamino group, a $C_{1-6}$ alkyl-carbonyl group (e.g., acetyl), a pyrrolidino, piperidino, morpholino, 2-pyridon-1-yl or 3-pyridon-1-yl group, a carbamoyl group and a mono- or di-$C_{1-6}$ alkyl-carbamoyl group (e.g., methylcarbamoyl, ethylcarbamoyl, dimethylcarbamoyl, diethylcarbamoyl);

A-(2): 1 to 3 substituents selected from the group consisting of a halogen atom (e.g., fluorine, chlorine, bromine), a $C_{1-6}$ alkoxy group (e.g., methoxy, ethoxy, propoxy, isopropoxy), a hydroxyl group, etc.;

A-(3): 1 or 2, preferably one moiety represented by the formula:

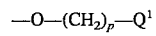

$$-O-(CH_2)_p-Q^1$$

wherein $Q^1$ represents a phenyl group which may be substituted by 1 to 3 substituents selected from the group consisting of a halogen atom (e.g., fluorine, chlorine, bromine), a $C_{1-6}$ alkyl group (e.g., methyl, ethyl, propyl, isopropyl, butyl, isobutyl, sec-butyl, tert-butyl, pentyl, isopentyl, neopentyl, hexyl) and a $C_{1-6}$ alkoxy group (e.g., methoxy, ethoxy, propoxy, isopropoxy); p is as defined hereinabove.

With respect to the above formulas, "T" represents a hydrogen atom or an optionally substituted hydrocarbon group, and "T'" represents an optionally substituted hydrocarbon group.

The "hydrocarbon group" represented by "T or T'" is exemplified by the groups listed in the following terms (1) and (2).

(1) Chain hydrocarbon group (straight ones preferred):
a) a $C_{1-10}$ alkyl group (e.g., methyl, ethyl, propyl, isopropyl, butyl, isobutyl, sec-butyl, tert-butyl, pentyl, isopentyl, neopentyl, hexyl, isohexyl, heptyl, octyl), particularly a $C_{1-6}$ alkyl group (e.g., methyl, ethyl, propyl, isopropyl, butyl, isobutyl, sec-butyl, tert-butyl, pentyl, hexyl);

b) a $C_{2-10}$ alkenyl group (e.g., vinyl, allyl, isopropenyl, butenyl, isobutenyl, sec-butenyl, 2-pentenyl, 3-pentenyl, 4-pentenyl, 2-hexenyl, 3-hexenyl, 5-hexenyl), particularly a $C_{2-6}$ alkenyl group (e.g., vinyl, allyl, isopropenyl, butenyl, isobutenyl, sec-butenyl);

c) a $C_{2-10}$ alkynyl group (e.g., propargyl, ethynyl, butynyl, 1-hexynyl, 2-hexynyl, 3-hexynyl, 4-hexynyl), particularly a $C_{2-6}$ alkinyl group (e.g., propargyl, ethynyl, butynyl, 1-hexynyl), (2) Cyclic hydrocarbon group:

a) a $C_{3-8}$ cycloalkyl group (e.g., cyclopropyl, cyclobutyl, cyclopentyl, 2-cyclopenten-1-yl, cyclohexyl, 2-cyclohexen-1-yl, cycloheptyl), particularly a $C_{3-6}$ cycloalkyl group (e.g., cyclopropyl, cyclobutyl, cyclopentyl, cyclohexyl);

b) a $C_{6-14}$ aryl group (e.g., phenyl, tolyl, xylyl, 1-naphthyl, 2-naphthyl, biphenyl, 2-indenyl, 2-anthryl), particularly phenyl group.

The "hydrocarbon group" represented by "T or T'" is preferably selected from items (1)-a), (1)-b) and (1)-c) above, and most preferably item (1)-a).

The "hydrocarbon group" represented by "T or T'" may have one or more substituents. Such substituents include a halogen atom (e.g., fluorine, chlorine, bromine, iodine), a nitro group, a cyano group, a hydroxy group, a $C_{1-6}$ alkoxy group (e.g., methoxy, ethoxy, propoxy, butoxy, isopropoxy), a $C_{1-6}$ alkylthio group (e.g., methylthio, ethylthio, propylthio), an amino group, a mono- or di-$C_{1-4}$ alkylamino group (e.g., methylamino, ethylamino, propylamino, dimethylamino, diethylamino), a cyclic amino group (e.g., pyrrolidinyl, piperidino, morpholino), a $C_{1-4}$ alkyl-carbonylamino group (e.g., acetylamino, propyonylamino, butyrylamino), a $C_{1-4}$ alkylsulfonylamino group (e.g., methylsulfonylamino, ethylsulfonylamino), a $C_{1-4}$ alkoxy-carbonyl group (e.g., methoxycarbonyl, ethoxycarbonyl, propoxycarbonyl), a carboxyl group, a $C_{1-6}$ alkyl-carbonyl group (e.g., methylcarbonyl, ethylcarbonyl, propylcarbonyl), a carbamoyl group, a mono- or di-$C_{1-4}$ alkylcarbamoyl group (e.g., methylcarbamoyl, ethylcarbamoyl, dimethylcarbamoyl) and a $C_{1-6}$ alkylsulfonyl group (e.g., methylsulfonyl, ethylsulfonyl, propylsulfonyl). Generally, the number of substituents is 1 to 5, preferably 1 or 2.

Most preferably, the "hydrocarbon group" represented by "T or T'" is be substituted by at most one substituent selected from a heterocyclic group, a $C_{6-10}$ aryl group (e.g., phenyl), a $C_{6-10}$ aryl-carbonyl group (e.g., benzoyl) and $C_{6-10}$ aryloxy group (e.g., phenoxy), etc.

The "heterocyclic group" which may be a substituent on "T or T'" is exemplified by those heterocyclic groups which may be substituents on "ring A". Particulaly, 1-phthalimide, 2,3,4,5-tetrahydro-(1H)-3-benzoazepinyl etc. are commonly used.

The "heterocyclic group", "$C_{6-10}$ aryl group", "$C_{6-10}$ aryl-carbonyl group" and "$C_{6-10}$ aryloxy group" which may be substituents on "T or T'" may have substituents thereon, such as those that the aryl group etc. represented by "Q" may have.

The "optionally substituted hydrocarbon group" represented by "T or T'" is also exemplified by a moiety represented by the formula:

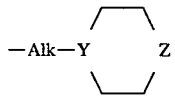

wherein all symbols are as defined hereinabove.

With respect to the above formula, "Alk" represents a $C_{1-10}$ alkylene group which may be substituted by an oxo group. The $C_{1-10}$ alkylene group is exemplified by the following:

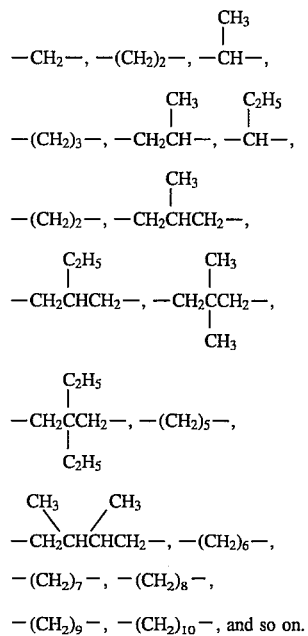

$-(CH_2)_7-$, $-(CH_2)_8-$, $-(CH_2)_9-$, $-(CH_2)_{10}-$, and so on.

Of these moieties, a straight $C_{1-6}$ alkylene group, such as $-CH_2-$, $-(CH_2)_2-$, $-(CH_2)_3-$ and $-(CH_2)_4-$, are commonly used. These $C_{1-10}$ alkylene groups may be substituted by 1 or 2 oxo groups. Such $C_{1-10}$ alkylene groups substituted by an oxo group such as followings:

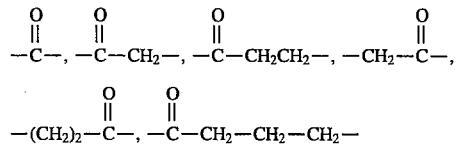

are commonly used.

Y represents a nitrogen atom or $-CH<$. Z represents an oxygen atom, $>CH-(CH_2)_q-W$ or $>N-(CH_2)_q-W$ (q represents an integer from 0 to 4; W represents a hydrogen atom or an optionally substituted aryl group or an optionally substituted heterocyclic group). The "optionally substituted aryl group or optionally substituted heterocyclic group" is exemplified by the same groups as defined "Q" hereinabove.

W is preferably:

(i) a hydrogen atom, (ii) a phenyl group which may be substituted by 1 to 3 substituents selected from the group consisting of a halogen atom (e.g., fluorine, chlorine, bromine, iodine), a $C_{1-6}$ alkyl group (e.g., methyl, ethyl, propyl, isopropyl, butyl, isobutyl, sec-butyl, tert-butyl, pentyl, isopentyl, neopentyl, hexyl) and a $C_{1-6}$ alkoxy groups (e.g., methoxy, ethoxy, propoxy, isopropoxy), etc.

Preferable examples for "T or T'" include:

(i) a $C_{1-6}$ alkyl group (e.g., methyl, ethyl, propyl, isopropyl, butyl, isobutyl, sec-butyl, tert-butyl, pentyl, isopentyl, neopentyl, hexyl) or a $C_{2-6}$ alkenyl group (e.g., vinyl, allyl, butyryl), and (ii) a group represented by the following formulas:

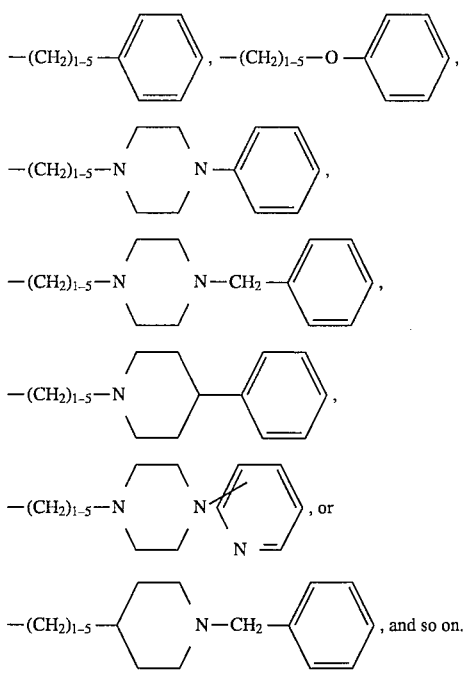

The "phenyl group, benzyl group and pyridyl group" in the groups listed in item (ii) may have at any possible positions thereon 1 to 3 substituents selected from the group consisting of a halogen atom (e.g., fluorine, chlorine, bromine, iodine), a $C_{1-6}$ alkyl group (e.g., methyl, ethyl, propyl, isopropyl, butyl, isobutyl, sec-butyl, tert-butyl, pentyl, isopentyl, neopentyl, hexyl), a $C_{1-6}$ alkoxy group (e.g., methoxy, ethoxy, propoxy, isopropoxy), a cyano group, a hydroxy group and an amino group, etc.

With respect to the above formulas, X is preferably —$CH_2$—, —CO— or —CH(OH)—, or —$CH_2$.

With respect to the above formulas, D represents —$CH_2$—, —O— or —NR— wherein R is a hydrogen atom or an optionally substituted hydrocarbon group.

The "optionally substituted hydrocarbon goroup" represented by "R" is exemplified by the same groups as defined "T and T'" hereinabove.

Preferable example of "R" is a hydrogen atom or a $C_{1-6}$ alkyl group (e.g. methyl, ethyl, etc.), and specifically a $C_{1-6}$ alkyl group (e.g. methyl).

Preferable example of "D" is —$CH_2$—.

With respect to the above formulas, m, e and f independently represent an integer from 1 to 3, and it is preferable that "m" be 2 and "e" and "f" be 1.

Preferable combinations of "ring A" and "T" include the following:

(1) Ring A is an aromatic ring which may be substituted by 1 to 3 substituents selected from the group consisting of a halogen atom, a $C_{1-6}$ alkoxy group and a hydroxyl group; and T is a group represented by the formula:

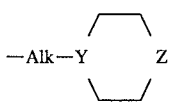

wherein Alk represents a $C_{1-10}$ alkylene group which may be substituted by an oxo group; Y represents a nitrogen atom or —CH<; Z represents an oxygen atom, >CH1'$(CH_2)_q$—W or >N—$(CH_2)_q$—W (q represents an interger from 0 to 4; W represents a hydrogen atom or an optionally substituted aryl group or an optionally substituted heterocyclic group), and (2) Ring A is an aromatic ring substituted by 1 or 2 substituents represented by the formula:

wherein p represents an integer from 0 to 4; Q represents an optionally substituted aryl group or an optionally substituted heterocyclic group; and T is a $C_{1-10}$ alkyl, $C_{2-10}$ alkenyl or $C_{2-10}$ alkynyl group.

Preferable examples of compound (I) or salt thereof are given below.

(A) A compound represented by the formula:

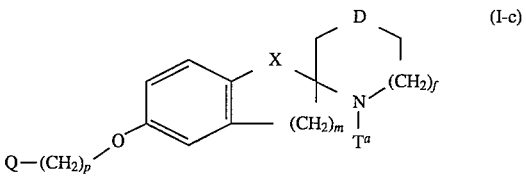

wherein $T^a$ represents an optionally substituted $C_{1-10}$ alkyl, $C_{2-10}$ alkenyl or $C_{2-10}$ alkynyl group; the other symbols are as defined hereinabove, or a salt thereof.

The "$C_{1-10}$ alkyl, $C_{2-10}$ alkenyl or $C_{2-10}$ alkynyl group" represented by "$T^a$" is exemplified by the same groups mentioned for "T" hereinabove. These groups may have substituents, and such substituents include the same substituents as those that the "hydrocarbon group" represented by "T or T'" hereinabove may have.

Preferable examples of "$T^a$" include a $C_{1-6}$ alkyl group (e.g., methyl, ethyl, propyl, isopropyl, butyl, isobutyl, sec-butyl, tert-butyl, pentyl, isopentyl, neopentyl, hexyl), with greater preference given to a $C_{1-4}$ alkyl group (e.g., methyl, ethyl, propyl, particularly propyl).

With respect to formula (I-c), "Q" is preferably a phenyl, 1-morpholinyl, 1-imidazolyl or 4-thiazolyl group, etc. which may be substituted by 1 to 3 substituents selected from the group consisting of a halogen atom (e.g., fluorine, chlorine, bromine, iodine), a $C_{1-6}$ alkyl group (e.g., methyl, ethyl, propyl, isopropyl, butyl, isobutyl, sec-butyl, tert-butyl, pentyl, isopentyl, neopentyl, hexyl), a $C_{1-6}$ alkoxyl group (e.g., methoxy, ethoxy, propoxy, isopropoxy) and a cyano group.

With respect to formula (I-c), "Q" is more preferably (i) a phenyl group which may be substituted by 1 or 2 substituents selected from the group consisting of a halogen atom (e.g., fluorine, chlorine, bromine, iodine) and a cyano group, or (ii) a phenyl group which may be substituted by one substituent selected from the group consisting of a halogen atom (e.g., fluorine, chlorine, bromine, iodine), a $C_{1-4}$ alkyl group (e.g., methyl, ethyl, propyl) and a $C_{1-4}$ alkoxy group (e.g., methoxy, ethoxy, propoxy, isopropoxy).

With respect to formula (I-c), it is preferable that "X" be —$CH_2$—, "m" be 2, "f" be 1 "D" be —$CH_2$— and "p" be 1 or 2.

(B) A compound represented by the formula:

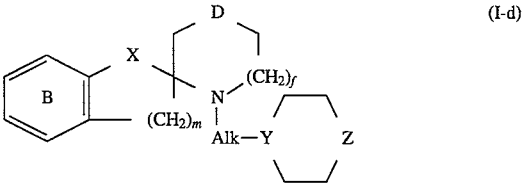

wherein ring B is an optionally substituted benzene ring; the other symbols are as defined hereinabove, or a salt thereof.

With respect to formula (I-d), ring B is an optionally substituted benzene ring. The substituents on the benzene ring include the same substituents as those that the "aromatic ring" represented by "ring A" hereinabove may have Specifically, "ring B" is preferably a benzene ring which may be substituted by 1 to 3 substituents selected from the group consisting of a halogen atom (e.g., fluorine, chlorine, bromine), a $C_{1-6}$ alkyl group (e.g., methyl, ethyl, propyl, isopropyl, butyl, isobutyl, sec-butyl, tert-butyl, pentyl, isopentyl, neopentyl, hexyl), a $C_{1-6}$ alkoxy group (e.g., methoxy, ethoxy, propoxy, isopropoxy, butoxy), a $C_{1-6}$ alkylthio group (e.g., methylthio, ethylthio, propylthio, isopropylthio), a mercapto group, a $C_{1-7}$ acylamino group (e.g., formylamino, acetylamino, propyonylamino, butyrylamino, benzoylamino), a $C_{1-3}$ acyloxy group (e.g., formyloxy, acetoxy, propionyloxy), a hydroxyl grous, a nitro group, a cyano group, a amino group, a mono- or di-$C_{1-4}$ alkylamino group (e.g., methylamino, ethylamino, propylamino, dimethylamino, diethylamino), a cyclic amino groups (e.g., pyrrolydinyl, piperidino, morpholino), a $C_{1-4}$ alkylsulfonylamino group (e.g., methylsulfonylamino, ethylsulfonylamino), a formyl group, a $C_{1-4}$ alkoxy-carbonyl group (e.g., methoxycarbonyl, ethoxycarbonyl, propoxycarbonyl), a carboxyl group, a $C_{1-6}$ alkyl-carbonyl group (e.g., acetyl, propionyl, butyryl, valeryl), a carbamoyl group, a mono- or di-$C_{1-4}$ alkylcarbamoyl group (e.g., methylcarbamoyl, ethylcarbamoyl) and a $C_{1-6}$ alkylsulfonyl group (e.g., methylsulfonyl, ethylsulfonyl, propylsulfonyl). A benzene ring which may be substituted by 1 or 2 substituents selected from the group consisting of a halogen atom (e.g., fluorine, chlorine, bromine), a $C_{1-6}$ alkoxy group (e.g., methoxy, ethoxy, propoxy, isopropoxy, butoxy), a hydroxyl group and an amino group are commonly used, with greater preference given to a benzene ring which may be substituted by 1 or 2 $C_{1-6}$ alkoxy group (e.g., methoxy, ethoxy, propoxy, isopropoxy, butoxy).

Most preferably, "ring B" is a moiety represented by the formula:

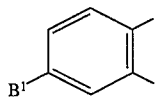

wherein $B^1$ represents a $C_{1-4}$ alkoxy group (e.g., methoxy, ethoxy, isopropoxy), or the like.

With respect to formula (I-d), "X" is preferably —$CH_2$—; "Alk" is preferably a straight $C_{1-4}$ alkylene group such as —$CH_2$—, —$(CH_2)_2$—, —$(CH_2)_3$— or —$(CH_2)_4$—; a straight $C_{2-3}$ alkylene group such as -$(CH_2)2$— and —$(CH_2)_3$— is commonly used; "m" and "f" are preferably 2 and 1, respectively. "f" is more preferably 1, "m" is more preferably 2.

With respect to formula (I-d), "Z" is preferably >CH—$(CH_2)_q$—W (q and W are of the same meanings as defined hereinabove), with preference given to a combination of 0 for "p" and a phenyl group for "W".

With respect to formula (I-d), "D" is preferably —$CH_2$—.

With respect to formula (I-d), >N—$(CH_2)_q$—W (q and W are as defined hereinabove) is also preferable for "Z". Here, it is preferable that (Z-a): "p" be 0 and "W" be a selected from the group consisting of (i) a halogen atom (e.g., fluorine, chlorine), (ii) a $C_{1-4}$ alkyl group which may be substituted by 3 halogen atoms (e.g., methyl, trifluoromethyl, ethyl, propyl, isopropyl) and (iii) a $C_{1-4}$ alkoxy group (e.g., methoxy, ethoxy, isopropoxy), or that (Z-b): "q" be 1 and "W" be a phenyl group.

With respect to formula (I-d), the combination of a nitrogen atom for "Y" and (Z-a) for "Z", the combination of a nitrogen atom for "Y" and (Z-b) for "Z", the combination of —CH< for "Y" and (Z-b) for "Z", etc. are preferred. (C) With respect to formula (I), ring A is preferably represented by the formula:

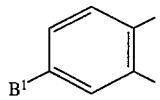

wherein the symbol $B^1$ is of the same meaning as defined hereinabove. It is preferable that "X" be —$CH_2$—, "D" be —$CH_2$—, "m" be 2, "f and e" be 1, "T" be a $C_{2-4}$ alkyl group substituted by one phenyl, phenoxy or 1-phthalimide group (e.g., 2-phenoxyethyl, 3-phenylpropyl, 4-phthalimidebutyl).

(D) A compound represented by the formula:

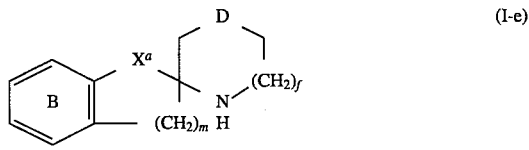

(I-e)

wherein $X^a$ represents —CO— or —CH(OH)—; the other symbols are of the same meanings as defined hereinabove.

With respect to formula (I-e), "ring B" may be optionally substituted by 1 or 2 substituents selected from the group consisting of a halogen atom (e.g., fluorine, chlorine, bromine), a $C_{1-4}$ alkoxy group (e.g., methoxy, ethoxy, isopropoxy), a hydroxyl group and an amino group; "D" be —$CH_2$—; and "m" be 2 and "f" be 1.

With respect to the above formulas, the "amino-protecting group" represented by "J" hereinabove is exemplified by the protective groups described in the "Protective Groups in Organic Synthesis", e.g., those of the acyl and carbamate types. Preferable protective groups of acyl type include a benzoyl, an optionally halogenated $C_{1-6}$ alkyl-carbonyl group (e.g., trifluoroacetyl); preferable protective groups of carbamoyl type include a $C_{1-6}$ alkoxy-carbonyl group (e.g., tert-butoxycarbonyl) and a $C_{7-10}$ aralkyl-carbonyl group (e.g., benzyloxycarbonyl, p-methoxybenzyloxycarbonyl). These protective groups can be eliminated by conventional methods such as hydrolysis and reduction, as described below.

With respect to the above formulas, the "leaving group" represented by "L" is exemplified by a halogen atom (e.g., chlorine, bromine, iodine), an optionally halogenated $C_{1-4}$ alkylsulfonyloxy group (e.g., methanesulfonyloxy, trifluoromethanesulfonyloxy) and a $C_{6-10}$ arylsulfonyloxy group (e.g., p-toluenesulfonyloxy, benzenesulfonyloxy), etc.

A preferable salt of compound (I) of the present invention is a medically acceptable acid salt. Such salts include inorganic salts such as hydrochloride, hydrobromide, hydroiodide, sulfate and phosphate, and organic acid salts such as acetate, oxalate, succinate, ascorbate, maleate, lactate, citrate, tartrate, methanesulfonate and benzoate. Furthermore, where the compounds have acidic groups such as —COOH, they may form salts with inorganic bases (e.g. alkali metals or alkaline earth metals such as sodium, potassium, calcium, magnesium, etc., ammonia, etc.), or organic bases (e.g. tri-$C_{1-3}$ alkylamines such as triethylamine etc.).

A compound in scope of this invention includes an optical isomers, and an optically active conformation resulting from resolution of such optical isomers are also covered by this invention.

Specifically, optical isomers can be resolved by using an intermediate for synthesis or optically resolving a racemate mixture of a subject matter, by conventional methods.

Methods of optical resolution include a method in which a salt formed with an optically active acid is separated by fractional recrystallization, a method in which a racemate or a salt thereof is subjected to chromatography using a column for separation of an optically active conformation (chiral column), for example, ENANTIO-OVM (produced by Tosoh Corporation), and followed by developing with water, various buffers (e.g., phosphate buffer), alcohol solvents (e.g., methanol, ethanol), nitrile solvents (e.g., acetonitrile) and organic solvents (e.g. hexane, ethyl ether), which are used singly or in combination, and a method in which a racemic mixture is condensed by a conventional method such as the acid chloride method, with an optically active organic acid such as MPTA [α-methoxy-α-(trifluoromethyl)phenylacetic acid] or menthoxyacetic acid, to yield an amide diastereomer mixture, which is separated by a conventional means of separation and purification such as fractional recrystallization or silica gel chromatography, followed by acidic or basic hydrolysis.

Spiroamine derivative (I) or a salt thereof of the present invention can be produced by various methods, including the method outlined by the reaction scheme given below.

A compound (I) or a salt thereof of the present invention can be converted into a salt by a conventional method when it is in a free form, and can be converted into a salt by a conventional method when it is in a salt. A compound (I) or salt thereof obtained by the above method can be isolated and purified by known methods, such as solvent extraction, liquid conversion, redissolution, crystallization, recrystallization and chromatography. When a compound (I) or salt thereof is an optically active conformation, it can be separated by the above-described methods of optical resolution.

The following reaction is carried out in a solvent.

Useful "ether solvents" include tetrahydrofuran, ethyl ether, dioxane, isopropyl ether and 1,2-dimethoxyethane.

Useful "halogenated hydrocarbon solvents" include dichloromethane, 1,2-dichloroethane, chloroform and carbon tetrachloride.

Useful "aromatic hydrocarbon solvents" include benzene, toluene and xylene.

Useful "alcohol solvents" include methanol, ethanol, isopropanol, tert-butanol, ethylene glycol and sec-butanol.

For example, a spiroamine skeleton represented by general formula (I) can be constructed by the following reaction scheme 1:

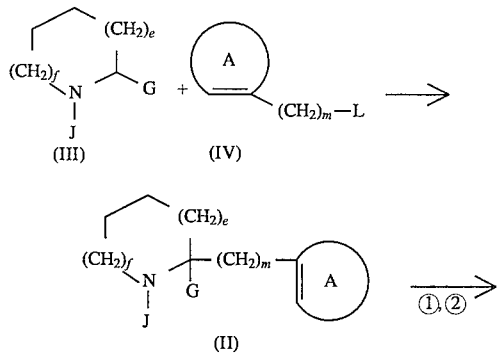

-continued
Reaction scheme 1

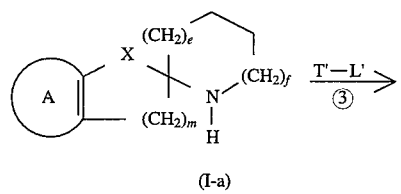

wherein G represents a cyano group, a carboxyl group, a $C_{1-6}$ alkoxy-carbonyl group (e.g., methoxycarbonyl, ethoxycarbonyl) or a benzyloxycarbonyl group; the other symbols are as defined hereinabove.

The substituent for "G" is preferably a cyano group, a carboxyl group, an ethoxycarbonyl group or a benzyloxycarbonyl group, or the like.

The amino-protecting group for "J" is preferably a benzoyl group, a benzyloxycarbonyl group, or the like.

The leaving group for "L" is preferably an iodo, a brom, a p-toluenesulfonyloxy, or the like.

Compound (III) can be produced by known methods or modifications thereof. For example, 1-benzoyl-2-piperidinecarbonitrile can be produced according to the method of G. Stork et al. [Tetrahedron Letters, No. 9, p. 771 (1979)].

Compound (IV) can be also prepared from corresponding alcohols by known methods [e.g., method described by Richard C. Larock in Comprehensive Organic Transformation, VCH Publishers Inc.] or modifications thereof.

Reaction of compounds (III) and (IV) may be carried out in an inert solvent, such as an ether solvent, N,N-dimethylformamide, dimethyl sulfoxide or hexamethylphosphoryltriamide, or a mixture thereof, in the presence of a strong base (e.g., lithium diisopropylamide, lithium dicyclohexylamide, lithium hexamethyldisilazide, potassium hexamethyldisilazide, sodium amide, potassium amide, potassium hydride, sodium hydride, potassium tert-butoxide, butyl lithium, tert-butyl lithium, sec-butyl lithium) at −78° to 100° C. for 5 minutes to 24 hours. A preferable base is lithium diisopropylamide; a preferable solvent is tetrahydrofuran (THF). It is preferable that reaction temperature be −20° to 10° C. and reaction time be 1 to 2 hours.

Cyclization î of compound (II) can be achieved by reaction with an acid (e.g., trifluoromethanesulfonic acid, trifluoroacetic acid, polyphosphoric acid, phosphorus pentachloride, trimethylsilyl trifluoromethanesulfonate, aluminum chloride, aluminum bromide, titanium tetrachloride, boron trifluoride, etherate, tin tetrachloride) in an inert solvent, such as a halogenated hydrocarbon, or without solvent, at −20° to 150° C. for 5 minutes to 24 hours. Although preferable conditions vary to some extent depending on the starting material used, preferable acids are aluminum chloride and trifluoromethanesulfonic acid. When aluminum chloride is used, dichloromethane, 1,2-dichloroethane, or the like, is used as a solvent, reaction temperature and time being 10 to 80° C. and about 1 to 4 hours, respectively. When trifluoromethanesulfonic acid is used, the reaction is carried out without solvent at 10° to 50° C. for about 1 to 12 hours.

Hydrolysis 2̂ can be achieved by acidic or alkalic conditions. This hydrolysis process goes with deprotection reaction in some cases. Alkali hydrolysis can be carried out by using 2 to 100 equivalents of an alkali (e.g., lithium hydroxide, sodium hydroxide, potassium hydroxide, barium hydroxide) at 10° to 120° C. for 5 minutes to 100 hours in a solvent, such as water, alcohol or ether, or a mixture thereof. Preferably, this reaction is carried out in a water-methanol mixed solvent with 5 to 10 equivalents of sodium hydroxide at 50° to 120° C. for 10 to 50 hours.

After cyclization, the carbonyl group for "X" can be modified by reduction using a known reducing reagent [e.g., reagent described by Richard C. Larock in Comprehensive Organic Transformation, VCH Publishers Inc.].

For example, a ketone having —CO— for "X" can easily be converted into an alcohol having —CH(OH)— for "X", by reaction with a metal hydride (e.g., aluminum lithium hydride, sodium borohydride, lithium borohydride, sodium cyanoborohydride, diborane, dibutyl aluminum hydride) or a metal (e.g., zinc, iron, sodium, potassium), in an inert solvent. Inert solvents include ether solvents (e.g., ethyl ether, tetrahydrofuran, dioxane), alcohol solvents (e.g., methanol, ethanol, tert-butanol), toluene and hexane.

The metal hydride is normally used at 1 to 20 equivalents, preferably 3 to 12 equivalents, reaction temperature being −70° to 100° C. Although preferable reaction temperature varies depending on the reducing agent used, −70° to 30° C. is preferred when a metal hydride is used.

An alcohol having —CH(OH)— for "X" can be reduced to a methylene having —CH$_2$— for "X" by catalytic reduction using a metal catalyst or by reaction using an organic silyl reagent. Metal catalysts include palladium catalyst, platinum catalyst and nickel catalyst. This reduction can be carried out under hydrogen pressure in an inert solvent (e.g., alcohol solvent, ethyl acetate), in the presence of an organic acid, such as acetic acid, or an inorganic acid, such as hydrochloric acid, at 0° to 150° C. for about 10 minutes to 48 hours. Usually the hydrogen pressure in the reaction system may be 1 atm. It is preferable in some cases to proceed under higher pressure (e.g., 2 to 10 atm).

When an organic silyl reagent (e.g., triethylsilane, phenyldimetylsilane) is used, it is added at 1 to 10 equivalents, preferably 1 to 5 equivalents, after dilution with an organic acid, such as trifluoroacetic acid, a boron trifluoride-ether complex, or an inert solvent, reaction temperature being 0° to 100° C., preferably 0° to 30° C., reaction time being 10 minutes to 24 hours.

It is also possible to replace the hydroxyl group of an alcohol having —CH(OH)— for "X" with a halogen (e.g., chloro, bromo) by a conventional method, followed by the above-described reduction reaction, to yield the desired product. Furthermore, a ketone can be reduced to methylene in a single process by a modification of a known method [e.g., method described by Richard C. Larock in Comprehensive Organic Transformation, VCH Publishers Inc.].

With respect to reaction 3̂, introduction of "T'" into the amino group of the spiro ring moiety can be achieved by a modification of a known method (e.g., method described in Yuki Gosei Kagaku, edited by Tetsuharu Kametani, Nankodo).

For example, the group for "T'" is introduced by reacting 1 to 5, preferably 1 to 3 equivalents of "T'-L'" (L' is identical to the leaving group "L") in an inert solvent, at 0° to 100° C. for 5 minutes to 100 hours. Preferable inert solvents include alcoholic solvents, etheral solvents, halogenated solvents, aromatic solvents, acetonitrile, N,N-dimethylformamide, acetone, methyl ethyl ketone and dimethyl sulfoxide, and may be used singly or in combination. Of these solvents, acetonitrile, N,N-dimethylformamide, acetone etc. are preferred. Reaction may be facilitated in the presence of 1 to 10 equivalents, preferably 1 to 3 equivalents of a base. Both inorganic and organic bases are effective. Inorganic bases include hydroxides, hydrides, carbonates, hydrogen carbonates and organic acid salts of alkali metals and alkaline earth metals, with preference given to potassium carbonate, sodium carbonate, sodium hydroxide, potassium hydroxide, sodium hydrogen carbonate and potassium hydrogen carbonate. Preferable organic bases are tertiary amines, such as triethylamine. The leaving group for "L'" is preferably a chloro, bromo, iodo, p-toluenesulfonyloxy, methanesulfonyloxy, or the like.

Acylation can also be easily carried out by a known acylation method when "T'" is an acyl group.

Acylation can be achieved by reaction in an inert solvent, such as a halogenated solvent, at 0° to 100° C., preferably 0° to 30° C., for 5 minutes to 24 hours. Reaction can be facilitated in the presence of 1 to 10 equivalents, preferably 1 to 3 equivalents of a base. Although both inorganic and organic bases are effective, triethylamine, diisopropylethylamine, 4-dimethylaminopyridine, N-methylmorpholine, 4-pyrrolidylpyridine, DBU (1,8-diazabicyclo[5.4.0]undeo-7-ene), DBN (1,5-diazabicyclo[4.3.0]-5-nene), pyridine etc. are preferred.

The substituent "T'" in compound (I-b) can also be converted into various derivatives by combining known methods of oxidation, reduction, substitution and other reactions.

When the substituent "T'" is an acyl group having a leaving group at terminal carbon atom represented by "L", as in compound (I-f), "L" can be replaced, by substitution reaction, with 1 to 5 equivalents, preferably 1 to 3 equivalents of a group represented by the formula:

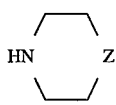

wherein Z is the same meaning as defined hereinabove.

Reaction scheme 2

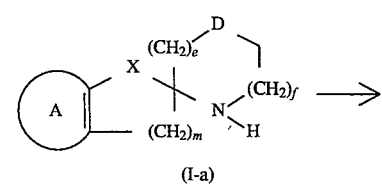

(I-a)

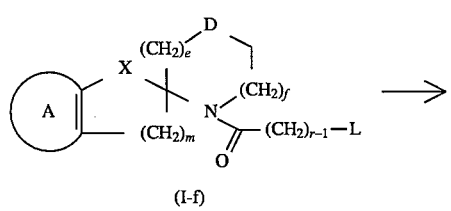

(I-f)

Reaction scheme 2 -continued

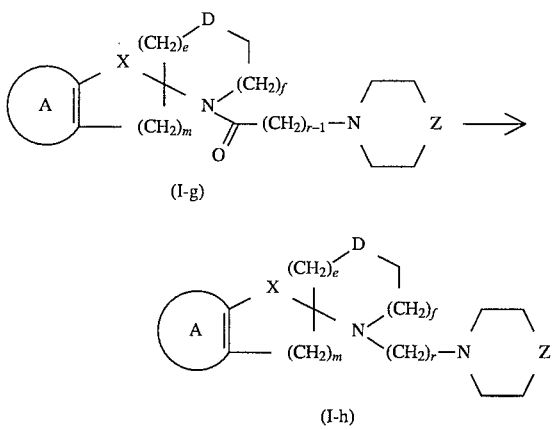

wherein r represents an integer from 1 to 10; the other symbols are of the same meanings as defined hereinabove.

In reaction scheme 2, substitution can be achieved in an inert solvent, such as an alcoholic solvent, etheral solvent, halogenated solvent, aromatic solvent, acetonitrile, N,N-dimethylformamide, acetone, methyl ethyl ketone or dimethyl sulfoxide, or a mixture thereof. Of these solvents, acetonitrile, N,N-dimethylformamide, acetone etc. are preferred. Reaction is facilitated in the presence of 1 to 10 equivalents, preferably 1 to 3 equivalents of a base. Both inorganic and organic bases are effective. Inorganic bases include hydroxides, hydrides, carbonates, hydrogen carbonates and organic acid salts of alkali metals and alkaline earth metals, with preference given to potassium carbonate, sodium carbonate, sodium hydroxide, potassium hydroxide, sodium hydrogen carbonate and potassium hydrogen carbonate. Preferable organic bases are tertiary amines, such as triethylamine. Reaction temperature is 0° to 100° C., reaction time being 5 minutes to 100 hours. It is preferable that reaction temperature is 10° to 50° C., and reaction is 1 to 5 hours.

Compound (I-g) can be converted into alkylated compound (I-h) by reduction. This reduction can be carried out by a modification of a known method [e.g., method described by Richard C. Larock in Comprehensive Organic Transformation, VCH Publishers Inc.]. For example, when a metal hydride is used, this reaction can be carried out in an inert solvent, such as an etheral solvent, With 2 to 16 equivalents, preferably 2 to 4 equivalents of the metal hydride, at −20° to 100° C., preferably 10° to 50° C. for 5 minutes to 18 hours.

Preferable metal hydrides include aluminum lithium hydride, aluminum hydride, diborane, lithium borohydride, sodium borohydride and analogs thereof.

With respect to compound (I-b), various substituents can be introduced into the aryl ring by a modification of a known method [e.g., method described by Richard C. Larock in Comprehensive Organic Transformation, VCH Publishers Inc.].

For example, a nitro group can be introduced at the aryl ring, using various nitrating agents (1 to 20 equivalents, preferably 1 to 5 equivalents). As nitrating agents, fuming nitric acid, nitric acid etc. are used singly or in combination with mineral acid. The resulting nitro compound (I-i) can be converted into an amino group by a reduction reaction, such as catalytic reduction. Catalytic reduction can easily be achieved by the above-described known methods. Preferably, catalytic reduction is carried out in the presence of palladium-carbon catalyst at a hydrogen pressure of 1 to 10 atm and a reaction temperature of 10° to 30° C. The resulting amino (I-j) can be modified by combining acylation, alkylation etc. Such substituents include cyclic amino groups, morpholyl groups, piperidyl groups and piperazinyl groups.

An example production of a pyrrolidinyl derivative is shown in reaction scheme 3.

Amino (I-j) is reacted with 1 to 5 equivalents, preferably 1 to 3 equivalents of 4-chlorobutyl chloride, or the like, in the presence of 1 to 5 equivalents, preferably 1 to 3 equivalents of an appropriate base (e.g., organic base, such as triethylamine) in an inert solvent, such as a halogenated solvent. Reaction temperature is normally −16° to 30° C., preferably 0° to 10° C., reaction time being 5 minutes to 18 hours, preferably 1 to 3 hours. Amino (I-j) is thus converted into 4-chlorobutyrylamide (I-k), which can be converted into a lactam by 1 to 5 equivalents, preferably 1 to 3 equivalents of a base (e.g., sodium hydride) in an inert solvent (e.g., N,N-dimethylformamide, acetonitrile, ether solvent, used singly or in combination) at −10° to 60° C. for 5 minutes to 18 hours. This lactam can be further converted into pyrrolidinyl (I-l) by reduction (same reaction conditions as those for production of compound (I-h)).

Reaction scheme 3

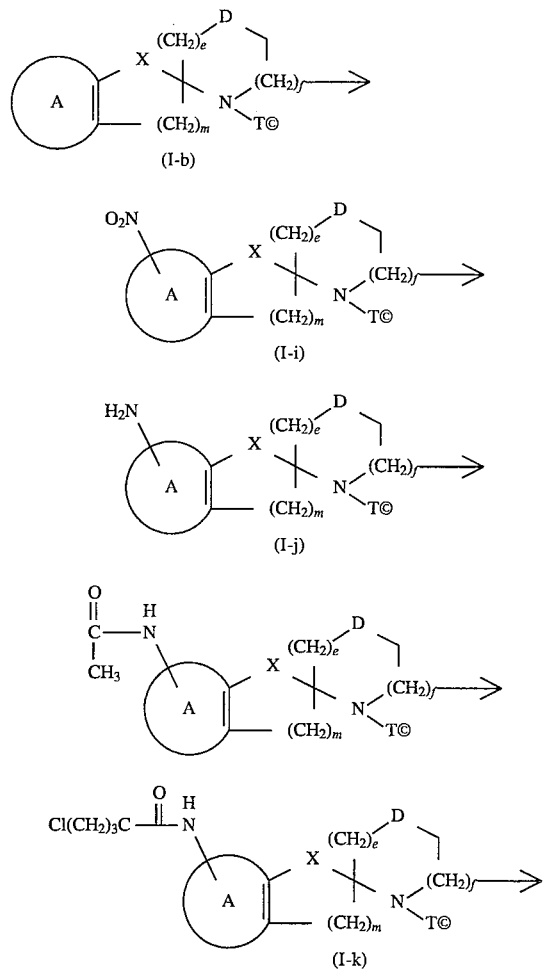

-continued
Reaction scheme 3

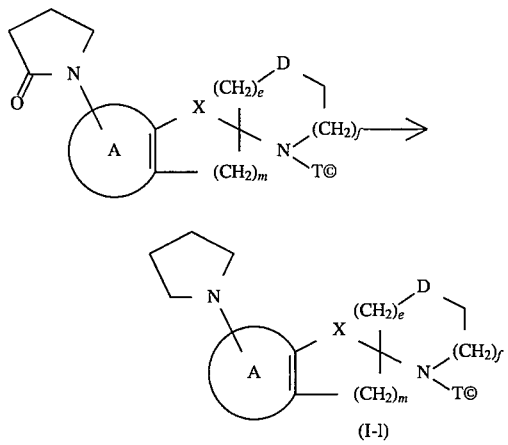

wherein all symbols are of the same meanings as defined hereinabove.

In another route of conversion (reaction scheme 4), the methoxy in the ring is easily convertible into hydroxy. Demethylating reagents include hydrobromic acid, hydroiodic acid, iodotrimethylsilane, aluminum chloride and boron tribromide; the reaction can easily be accomplished using 5 to 100 equivalents of hydrobromic acid. Reaction temperature is normally 50° to 170° C., preferably 100° to 130° C. reaction time being 30 minutes to 24 hours, preferably 1 to 5 hours.

This hydroxy can be further converted into various derivatives by alkylating with Q—(CH$_2$)$_p$—L (L represents the same leaving group as defined above).

Alkylation can be carried out in an inert solvent, such as an alcohol solvent, ether solvent, halogen solvent, aromatic solvent, acetonitrile, N,N-dimethylformamide, acetone, methyl ethyl ketone, or dimethyl sulfoxide, or a mixture thereof, in the presence of 1 to 5 equivalents, preferably 1 to 3 equivalents of a base. Of these solvents, acetonitrile, N,N-dimethylformamide, acetone etc. are preferred. Both inorganic and organic bases are effective. Inorganic bases include hydroxides, hydrides, carbonates, hydrogen carbonates and organic acid salts of alkali metals and alkaline earth metals, with preference given to potassium carbonate, sodium carbonate, sodium hydroxide, potassium hydroxide, sodium hydrogen carbonate and potassium hydrogen carbonate. Preferable organic bases are tertiary amines, such as triethylamine. Reaction temperature is 0° to 100° C. reaction time being 5 minutes to 100 hours. It is preferable that reaction time be 10 to 50° C. and reaction time be 1 to 5 hours.

Reaction scheme 4

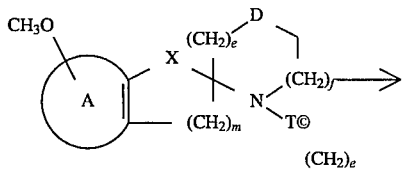

-continued
Reaction scheme 4

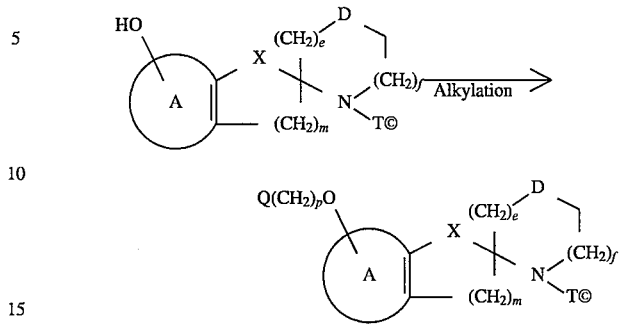

wherein all symbols are as defined hereinabove.

"Ring A" can be acylated or alkylated. For example, acylation can be achieved by reaction with an acid halide or acid anhydride, in an inert solvent, such as a halogenated hydrocarbon or aromatic solvent, or without solvent, at a reaction temperature of 0° to 200° C., preferably 0° to 150° C. for 5 minutes to 100 hours, preferably 15 minutes to 24 hours, in the presence of 1 to 10 equivalents, preferably 1 to 5 equivalents of an acid [e.g., Lewis acid (aluminum chloride etc.), sulfuric acid, polyphosphoric acid].

"Ring A" can have a halogen atom, such as bromo or chloro, introduced therein. For example, bromination can be achieved by reacting ring A in a halogen hydrocarbon solvent in the presence or absence of 1 to 10 equivalents, preferably 1 to 5 equivalents of a Louis acid, such as aluminum chloride, with 1 to 5 equivalents, preferably 1 to 3 equivalents of bromine, or the like, at 0° to 150° C., preferably 40° to 80° C. The resulting halogen-containing derivative can be converted into various substituents by known methods.

The compound of this invention having an oxygen atom for D is synthesized via, for example, reaction scheme 5 below.

Reaction scheme 5

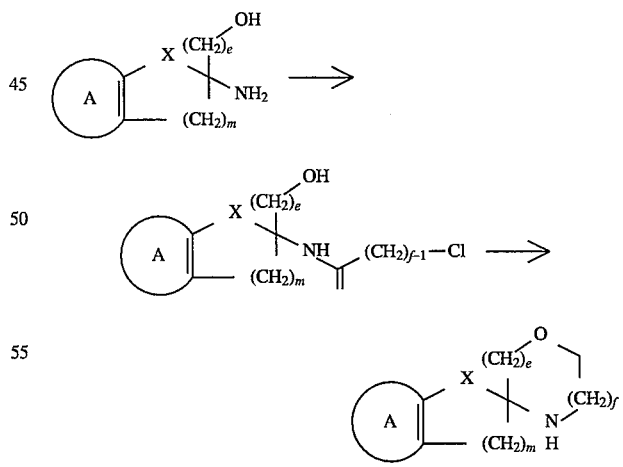

An aminocarboxylic acid that can be produced by hydrolysing an easily available hydantoin derivative [see Helvetica Chimica, Acta, Vol. 75, p. 1666 (1992)] is reduced to an amino alcohol, which is then subjected to halo-acetylation under the acylation conditions of reaction scheme 2. It is preferable that this reduction be carried out with a metal hydride (e.g., lithium aluminum hydride, diborane, used at 2 to 10 equivalents) in an inert solvent, such as an ether, at room temperature to refluxing temperature for 15 minutes to 18 hours.

Example haloacetyls include chloroacetyl, bromoacetyl and iodoacetyl. The reaction is carried out at room temperature in a solvent such as ethyl acetate in the presence of 1 to 3 equivalents of a base (e.g., inorganic base such as sodium carbonate, sodium hydrogen carbonate or sodium hydroxide, or organic base such as triethylamine) for 1 minute to 1 hour.

Cyclization is carried out in a solvent such as DMF or THF with a strong base (e.g., sodium hydride, potassium hydroxide, t-butoxypotassium, used at 1 to 10 equivalents) at room temperature to 60° C for 0.5 to 10 hours.

The final reduction is achieved under the same conditions as those for the above reduction. Preferably, the reaction is carried out at 30° C. to refluxing temperature.

The compound of claim 1 having —NR— (R is of the same meaning as defined hereinabove) for D is produced by reacting a diketopiperazine derivative that can easily be produced from an aminocarboxylic acid, with a metal hydride, particularly aluminum hydride (4 to 10 equivalents), in an ether solvent at room temperature for 5 minutes to 3 hours.

Reaction Scheme 6

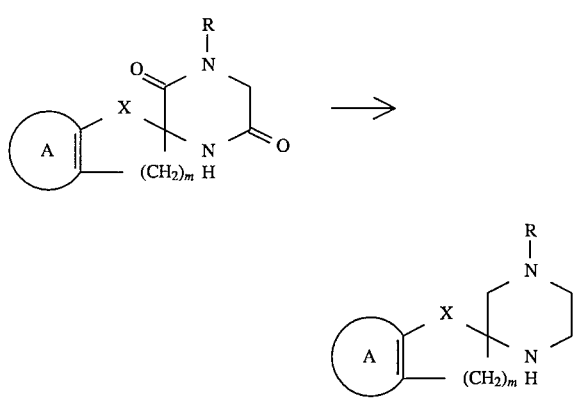

A starting compound, intermediate or salt thereof of the present invention can be isolated and purified by known methods such as solvent extraction, liquid conversion, redissolution, salting-out, crystallization, recrystallization and chromatography, but may be directly used as a starting material for the next process in the form of a reaction mixture without isolation.

With respect to the various reactions for the present invention and reactions for synthesizing a starting material compound, an amino group, carboxyl group or hydroxyl group contained as a substituent in the starting material compound may be protected by a protective group commonly used in peptide chemistry. And a subject matter can be obtained by removing the protective group as necessary after a reaction.

Examples of the protective group for such amino group include a $C_{1-6}$ alkyl-carbonyl group (e.g., formyl, acetyl, ethylcarbonyl), a $C_{1-6}$ alkyloxycarbonyl group (e.g., methoxycarbonyl, ethoxycarbonyl), a benzoyl group, a $C_{7-10}$ aralkyl-carbonyl group (e.g., benzylcarbonyl), a trityl group, a phthaloyl group and a N,N-dimethylaminomethylene group. These groups may be substituted by 1 to 3 substituents selected from a halogen atom (e.g., fluorine, chlorine, bromine, iodine), a nitro group, etc.

Examples of the protective group for such carboxyl group include a $C_{1-6}$ alkyl group (e.g., methyl, ethyl, n-propyl, isopropyl, butyl, tert-butyl), a phenyl group, a trityl group and a silyl group. These groups may be substituted by 1 to 3 substituents selected from a halogen atom (e.g., fluorine, chlorine, bromine, iodine), a $C_{1-6}$ alkyl-carbonyl group (e.g., formyl, acetyl, ethylcarbonyl, butylcarbonyl), a nitro group, etc.

Examples of the protective group for such carboxyl group include a $C_{1-6}$ alkyl group (e.g., methyl, ethyl, n-propyl, isopropyl, butyl, tert-butyl), a phenyl group, a $C_{7-10}$ aralkyl group (e.g., benzyl), a $C_{1-6}$ alkyl-carbonyl group (e.g., formyl, acetyl, ethylcarbonyl), a benzoyl group, a $C_{7-10}$ aralkyl-carbonyl group (e.g., benzylcarbonyl), a pyranyl group, a furanyl group and a silyl group. These groups may be substituted by 1 to 3 substituents selected from a halogen atom (e.g., fluorine, chlorine, bromine, iodine), a $C_{1-6}$ alkyl group (e.g., methyl, ethyl, n-propyl), a phenyl group, a $C_{7-10}$ aralkyl group (e.g., benzyl), a nitro group, etc.

These protective groups can be eliminated by known methods or modifications thereof, including those using acid, base, reduction, ultraviolet rays, hydrazine, phenylhydrazine, sodium N-methyldithiocarbamate, tetrabutylammonium fluoride, palladium acetate, etc.

The starting compound and intermediate may form a salt. Such salts include inorganic salts such as hydrochloride, hydrobromide, hydroiodide, sulfate and phosphate, and organic acid salts such as acetate, oxalate, succinate, ascorbate, maleate, lactate, citrate, tartrate, methanesulfonate and benzoate. Furthermore, where these compounds have acidic groups such as —COOH, they may form salts with inorganic bases (e.g. alkali metals or alkaline earth metals such as sodium, potassium, calcium, magnesium, etc., ammonia, etc.), or organic bases (e.g. tri-$C_{1-3}$ alkylamines such as triethylamine etc.).

A compound (I) of the present invention or a pharmaceutically acceptable salt thereof inhibits monoamine uptake in synapses, monoamine oxidase B activity and/or Ca ion uptake in nerve cells, in humans and nonhuman mammals (e.g., mice, rats, rabbits, dogs, bovines, pigs), and can be safely used to prevent and treat various diseases in humans, for examples, mental disorders such as depression, anxiety, alcohol dependence, appetite disorder, panic attack and compulsion, nerve degenerative diseases such as Parkinsonism and Alzheimer's disease, and cerebral vascular disorders such as epilepsy, spasms, cerebral stroke and cerebral infarction.

A compound (I) of the present invention or a salt thereof is effective against emotional disorders such as depression, anxiety, alcohol dependence, appetite disorder, panic attack and compulsion, because it inhibits a uptake of monoamines such as norepinephrine (NE) and serotonin (5-HT) in the synapse.

These compounds are also effective in preventing and treating nerve degenerative diseases such as Parkinsonism and Alzheimer's disease, because they possess monoamine oxidase B inhibitory activities. Furthermore, these compounds show anti-epileptic action and antispasmodic action, or show prophylactic and therapeutic effects against cerebral vascular disorders such as cerebral stroke and cerebral infarction, or dysmnesia, emotional disorder, etc. that accompany such cerebral vascular disorders, by suppressing nerve cell death, because they suppress abnormal inflow of Ca ions in nerve cells.

A compound (I) of the present invention or a salt thereof is low in toxicity and adverse reaction. The oral acute toxicity ($LD_{50}$) of the compound in rats exceeds 100 mg/kg.

A compound (I) of the present invention or a salt thereof can be safely administered orally or parenterally, as a pharmaceutical composition mixed with a pharmaceutically acceptable carrier, such as in the form of tablets (including sugar-coated tablets and film-coated tablets), powders, granules, capsules (including soft capsules), solutions, injections, suppositories and sustained-release preparations, as being prepared by a known method. Although the dose varies depending on subject and route of administration, a type of disease and other factors, it may be orally administered at a daily dose of 0.1 to 500 mg, preferably 10 to 100 mg, in one to several portions, for an adult (60 kg) for treating Parkinsonism.

Pharmaceutically acceptable carriers are various organic or inorganic carrier substances in common use as pharmaceutical materials, including excipients, lubricants, binders and disintegrating agents for solid preparations, and solvents, dissolution aids, suspending agents, isotonizing agents, buffers and soothing agents for liquid preparations. Other pharmaceutical additives, such as preservatives, antioxidants, coloring agents and sweetening agents, may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscalmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and monostearic glycerol, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include buffer solutions of phosphates, acetates, carbonates and citrates. Preferable soothing agents include benzyl alcohol. Preferable preservatives include p-oxybenzoic acid esters, chlorobutanol, benzyl alcohol, phenethyl alcohol, dehydroacetic acid and sorbic acid. Preferable antioxidants include sulfites and ascorbic acid.

The present invention is hereinafter described in more detail by means of the following reference examples, working examples and experimental examples. These examples exemplify, but do not limit, the present invention, and may be varied, as long as they remain within the scope of the invention.

In the following reference examples and working example, the term "room temperature" is generally defined as 0° to 30° C. The following abbreviations are defined as follows:

| s: Singlet |
| d: Doublet |
| t: Triplet |
| q: Quartet |
| quint: Quintet |
| m: Multiplet |
| br: Broad |
| J: Coupling constant |
| Hz: Hertz |
| CDCl$_3$: Heavy chloroform |

NMR spectra of a hydrochloride of presented compound was measured by using CDCl$_3$ solvent including the free form.

REFERENCE EXAMPLE 1-1

1-Benzoyl-2-(2-phenylethyl)-2-piperidinecarbonitrile

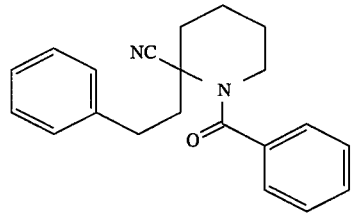

To 200 ml of a tetrahydrofuran solution of 140 mmol of lithium diisopropylamide, 15 g of solid 1-benzoyl-2-piperidinecarbonitrile was added at −78° C. After stirring for 30 minutes, 100 ml of a tetrahydrofuran solution of 33.2 g of phenethyl iodide was added drop by drop at −78° C. After completion of dropwise addition, the reaction mixture was gradually heated to 0° C. Water was added; the organic layer was separated; the water layer was further extracted with ethyl acetate. The organic layers were combined, dried over magnesium sulfate, and filtered, after which the solvent was distilled off. The residue was purified by silica gel column chromatography with ethyl acetate:hexane (1:2) as a developing solvent; the solution containing the desired product was distilled under reduced pressure; the resulting solid was recrystallized from ethyl acetate-hexane to yield 17.3 g of a colorless crystal. Melting point: 65°–67° C.

$^1$H-NMR (ppm, CDCl$_3$): 1.52–2.00 (4H, m), 2.19 (2H, t, J=6 Hz), 2.37–2.98 (4H, m), 3.29–3.57 (2H, m), 7.13–7.56 (10H, m)

Elemental analysis (for C$_{21}$H$_{22}$N$_2$O): Calculated: C, 79.21; H, 6.96; N, 8.80 Found: C, 79.13; H, 6.89; N, 8.64

The following compounds were synthesized in the same manner as in Reference Example 1-1 described hereinabove.

REFERENCE EXAMPLE 1-2

1-Benzoyl-2-[2-(3-methoxyphenyl)ethyl]-2-piperidinecarbonitrile

REFERENCE EXAMPLE 1-3

1-Benzoyl-2-[2-(3,4-dimethoxyphenyl)ethyl]-2-piperidinecarbonitrile

REFERENCE EXAMPLE 1-4

1-Benzoyl-2-[2-(2-thienyl)ethyl]-2-piperidinecarbonitrile

REFERENCE EXAMPLE 1-5

1-Benzoyl-2-[2-(3-thienyl)ethyl]-2-piperidinecarbonitrile

REFERENCE EXAMPLE 1-6

1-Benzoylhexahydro-2-(2-phenylethyl)-1H-azepine-2-carbonitrile

Table 1 and 2 show the structural formulas, physical properties and NMR spectra of these compounds.

TABLE 1

| Reference Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 1-2 | (structure: 3-methoxyphenethyl-piperidine with NC and N-benzoyl) | (1) 82–84 (2) C$_{22}$H$_{24}$N$_2$O$_2$ | ① 75.83 ② 75.58 | 6.94 6.98 | 8.04 7.92 | 1.55–1.98(4H, m), 2.19(2H, t, J=6Hz), 2.36–2.96(4H, m), 3.27–3.57(2H, m), 3.79(3H, s), 6.71–6.85(3H, m), 7.14–7.25 (1H, m), 7.36–7.56(5H, m) |
| 1-3 | (structure: 3,4-dimethoxyphenethyl-piperidine with NC and N-benzoyl) | (1) Oil (2) C$_{23}$H$_{26}$N$_2$O$_3$ | ① 72.99 ② 73.21 | 6.92 7.16 | 7.40 7.35 | 1.54–1.99(4H, m), 2.19(2H, t, J=6Hz), 2.34–2.94(4H, m), 3.27–3.56(2H, m), 3.85(3H, s), 3.87(3H, s), 6.72–6.83(3H, m), 7.37–7.58(5H, m) |
| 1-4 | (structure: 2-thienylethyl-piperidine with NC and N-benzoyl) | (1) 109–111 (2) C$_{19}$H$_{20}$N$_2$OS | ① 70.34 ② 70.25 | 6.21 6.07 | 8.63 8.43 | 1.50–1.97(4H, m), 2.17(2H, t, J=6Hz), 2.45–2.80(2H, m), 2.92–3.22(2H, m), 3.29–3.58 (2H, m), 6.83–6.87(1H, m), 6.92(1H, dd, J=5, 4Hz), 7.13 (1H, dd, J=5, 2Hz), 7.37– dd, 7.58(5H, m) |

TABLE 2

| Reference Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 1-5 | (structure: 3-thienylethyl-piperidine with NC and N-benzoyl) | (1) 90–92 (2) C$_{19}$H$_{20}$N$_2$OS | ① 70.34 ② 70.51 | 6.21 6.06 | 8.63 8.40 | 1.58–1.98(4H, m), 2.17(2H, t, J=6Hz), 2.40–3.05(4H, m), 3.30–3.60(2H, m), 6.96–7.03(2H, m), 7.23–7.28(1H, m), 7.35–7.59(5H, m) |

TABLE 2-continued

| Reference Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 1-6 | | (1) 116–118 (2) C$_{22}$H$_{24}$N$_2$O | ① 79.48 ② 79.15 | 7.28 7.53 | 8.43 8.37 | 1.25–1.76(3H, m), 1.80–3.23(10H, m), 3.51–3.67(1H, m), 7.08–7.50(10H, m) |

REFERENCE EXAMPLE 2-1

2-chloroacetylamino-2-hydroxymethyltetralin

To a suspension of 2-aminotetralincarboxylate (500 mg, 2.6 mmol) in THF (10 ml), lithium aluminum hydride (250 mg, 6.5 mmol) was added, while the suspension was stirred at room temperature, followed by further stirring at constant temperature for 2 hours. To this mixture, a 1N aqueous sodium hydroxide solution was added. After the precipitate was filtered out, the mother liquor was washed with saturated saline and dried over anhydrous sodium sulfate. The solvent was distilled off under reduced pressure to yield an almost pure aminoalcohol (420 mg, 85%) as a colorless syrup. The alcohol (420 mg, 2.2 mmol) was then dissolved in an ethyl acetate (10 ml)-saturated sodium carbonate solution (10 ml). To this solution, chloroacetyl chloride (340 mg, 3 mmol) was added drop by drop, while the solution was vigorously stirred under ice cooling conditions. Five minutes later, the organic layer was separated, washed with saturated saline and dried over anhydrous sodium sulfate. After the solvent was distilled off under reduced pressure, the residue was subjected to silica gel column chromatography for elution with hexane-ethyl acetate (1:1) to yield 400 mg (72%) of the title compound.

REFERENCE EXAMPLE 2-2

2-Chloroacetylamino-2-hydroxymethyl-6-methoxytetralin was synthesized in the same manner as in Reference Example 2-1.

REFERENCE EXAMPLE 2-3

2-Chloroacetylamino-2-hydroxymethyl-7-methoxytetralin was synthesized in the same manner as in Reference Example 2-1.

REFERENCE EXAMPLE 2-4

2-Chloroacetylamino-6,7-dimethoxy-2-hydroxymethyltetralin was synthesized in the same manner as in Reference Example 2-1.

Table 3 shows the structural formulas, physical properties and NMR spectra of these compounds.

TABLE 3

| Reference Example | Structural Formula | Melting Point (°C.) or Physical Property | $^1$H—NMR(ppm, CDCl$_3$) |
|---|---|---|---|
| 2-1 | | oil | δ: 1.97(1H, ddd, J=13.0, 8.8, 7.0Hz), 2.26(1H, ddd, J=13.0, 7.9, 5.8Hz), 2.72–3.09(4H, m), 3.81(2H, s), 3.98(2H, s,), 4.04–4.45(1H, br), 6.60(1H, br s), 7.05–7.19(4H, m) |
| 2-2 | | oil | δ: 1.95(1H, m), 2.26(1H, m), 2.70–3.00(4H, m), 3.78(3H, s), 3.80(2H, s), 3.98(2H, s), 6.60(1H, br s), 6.64–6.75(2H, m), 7.00(1H, d, J=8.4Hz) |
| 2-3 | | oil | δ: 1.92(1H, m), 2.25(1H, m), 2.65–3.08(4H, m), 3.76(3H, s), 3.79(2H, d, J=4.6Hz), 3.97(2H, s), 4.23(1H, br s), 6.60(1H, s), 6.61(1H, s), 6.73(1H, dd, J=8.4, 2.6Hz), 7.03(1H, d, J=8.4Hz) |

TABLE 3-continued

| Reference Example | Structural Formula | Melting Point (°C.) or Physical Property | $^1$H—NMR(ppm, CDCl$_3$) |
|---|---|---|---|
| 2-4 | MeO, MeO — tetralin with CH$_2$OH and NHC(O)CH$_2$Cl substituents | 210–212 | δ: 1.62(1H, m), 2.30(1H, m), 2.55–2.98(4H, m), 3.58(2H, br s), 3.70(6H, s), 3.97(2H, q, J=17.6, 12.4Hz), 4.82(1H, br t, J=6Hz), 6.60, 6.64(1H each, s), 7.59(1H, br s), (DMSO-d$^6$) |

REFERENCE EXAMPLE 3-1

Spiro[tetralin-2,3'-morpholine-5'-one]

To a suspension of sodium hydride (120 mg, 5 mmol, 60% oil, washed with hexane) in DMF (3 ml), a solution of 2-chloroacetylamino-2-hydroxymethyltetralin (400 mg, 1.6 mmol) in DMF (3 ml) was added drop by drop, while the suspension was stirred under ice cooling conditions. After cooling to room temperature, the mixture was stirred for 3 hours at constant temperature. After a large amount of water was added, the mixture was extracted with ethyl acetate. The organic layer was washed with wager several times, washed with saturated saline and dried over anhydrous sodium sulfate. After the solvent was distilled off under reduced pressure, the residue was subjected to silica gel column chromatography for elution with hexane-ethyl acetate (1:1–1:2) to yield 150 mg (43%) of the title compound as a white crystal.

REFERENCE EXAMPLE 3-2

6-Methoxyspiro[tetralin-2,3'-morpholine]-5'-one

To a solution of 2-chloroacetylamino-2-hydroxy-6-methoxytetralin (450 mg, 1.6 mmol) in THF (15 ml), 60% oily sodium hydride (200 mg, 5.0 mmol) was added, while the solution was stirred under ice cooling conditions. After cooling to room temperature, the mixture was stirred for 3 hours at constant temperature. After a saturated aqueous solution of ammonium chloride was added, the mixture was extracted with ethyl acetate. The organic layer was washed with saturated saline and dried over anhydrous sodium sulfate. The solvent was distilled off under reduced pressure to yield about 400 mg (almost 100%) of the title compound as a crude crystal, a portion of which was then recrystallized from chloroform-isopropyl ether.

REFERENCE EXAMPLE 3-3

7-Methoxyspiro[tetralin-2,3'-morpholine]-5'-one was synthesized in the same manner as in Reference Example 3-2.

REFERENCE EXAMPLE 3-4

6,7-Dimethoxyspiro[tetralin-2,3'-morpholine]-5'-one was synthesized in the same manner as in Reference Example 3-2.

Table 4 shows the structural formulas, physical properties and NMR spectra of these compounds.

TABLE 4

| Reference Example | Structural Formula | Melting Point (°C.) or Physical Property | $^1$H—NMR(ppm, CDCl$_3$) |
|---|---|---|---|
| 3-1 | spiro[tetralin-2,3'-morpholine]-5'-one | 164–166 | δ: 1.80–2.15(2H, m), 273–3.07(4H, m), 3.69(2H, s), 4.20(2H, s), 6.32(1H, br s), 7.03–7.20(4H, m) |
| 3-2 | 6-MeO-spiro[tetralin-2,3'-morpholine]-5'-one | 173–174 | δ: 1.78–2.15(2H, m), 2.65–2.95(4H, m, 3.68(2H, s), 3.78(3H, s), 4.20(2H, s), 6.10(1H, br s), 6.63–6.76(2H, m), 6.98(1H, d, J=8.4Hz) |
| 3-3 | 7-MeO-spiro[tetralin-2,3'-morpholine]-5'-one | 144–148 | δ: 1.78–2.15(2H, m), 2.69–3.01(4H, m), 3.69(2H, s), 3.78(3H, s), 4.21(2H, s), 6.00(1H, br s), 6.59(1H, d, J=2.8Hz), 6.76(1H, dd, J=8.4, 2.8Hz), 7.05(1H, d, J=8.4Hz) |

TABLE 4-continued

| Reference Example | Structural Formula | Melting Point (°C.) or Physical Property | $^1$H—NMR(ppm, CDCl$_3$) |
|---|---|---|---|
| 3-4 | MeO, MeO — tetralin — N(H) — C(=O) — O (morpholinone-type) | 202–204 | δ: 1.75–1.95(1H, m), 1.96–2.15(1H, m), 2.65–2.95(4H, m), 3.69(2H, s), 3.84, 3.86(3H, each, s), 4.21(2H, s), 6.03(1H, br s), 6.57, 6.01(1H each, s) |

REFERENCE EXAMPLE 4-1

Ethyl 2-(N-benzyloxycarbonyl-N-methylaminoacetylamino) tetralin-2-carboxylate

To a solution of ethyl 2-aminotetralin-2-carboxylate (438 mg, 2.0 mmol), N-benzyloxycarbonylsarcosine (446 mg, 2.0 mmol) and 1-ethyl-3-(3'-dimethylaminopropyl)carbodiimide hydrochloride (400 mg, 7.1 mmol) in dichloromethane (5 ml), triethylamine (212 mg, 2.1 mmol) was added, while the solution was stirred under ice cooling conditions, followed by further stirring at room temperature for 2 hours. After the reaction mixture was concentrated under reduced pressure, the resulting residue was dissolved in ethyl acetate. This solution was washed by sequential additions of 1N hydrochloric acid, saturated aqueous sodium bicarbonate and saturated saline, and dried over anhydrous sodium sulfate. After the solvent was distilled off under reduced pressure, the obtained residue was subjected to silica gel column chromatography for elution with hexane-ethyl acetate (1:1) to yield 750 mg (88%) of the title compound.

REFERENCE EXAMPLE 4-2

Ethyl 2-(N-benzyloxycarbonyl-N-methylaminoacetylamino)-6,7-dimethoxytetralin-2-carboxylate was synthesized in the same manner as in Reference Example 4-1.

Table 5 shows the structural formulas, physical properties and NMR spectra of these compounds.

TABLE 5

| Reference Example | Structural Formula | Melting Point (°C.) or Physical Property | $^1$H—NMR(ppm, CDCl$_3$) |
|---|---|---|---|
| 4-1 | tetralin-2-CO$_2$Et, 2-N(H)-CH$_2$CH$_2$-N(Me)(CBz) | oil | δ: 1.24(3H, t, J=7.0Hz), 2.05–2.20(1H, m), 2.40–3.10(7H, m), 3.30(1H, d, J=16.4Hz), 3.84(2H, s), 4.20(2H, q, J=7.4Hz), 4.99(2H, s), 6.38–6.50(1H, br), 7.00–7.20(4H, m), 7.22–7.40(5H, m) |
| 4-2 | MeO, MeO-tetralin-2-CO$_2$Et, 2-N(H)-C(=O)-CH$_2$-N(Me)(CBz) | oil | δ: 1.25(3H, t, J=7.0Hz), 2.00–2.16(1H, m, 2.39–3.00(7H, m), 3.24(1H, d, J=16.4Hz), 3.80, 3.82(3H each, s), 3.85(2H, s), 5.02(2H, s), 6.37–6.50(1H, br), 6.49, 6.57(1H each, s), 7.32(5H, br s) |

Bz: Benzyloxy carbonyl

REFERENCE EXAMPLE 5-1

Ethyl 2-(N-methylaminoacetylamino)tetralin-2-carboxylate

A solution of ethyl 2-(N-benzyloxycarbonyl-N-methylaminoacetylamino)tetralin-2-carboxylate (750 mg, 1.8 mmol) in ethanol (20 ml) was subjected to hydrogenation in the presence of 10% palladium-carbon (200 mg) for 5 hours. After the catalyst was filtered off, the mother liquid was concentrated under reduced pressure to yield 500 mg (96%) of the title compound as a crude substance.

REFERENCE EXAMPLE 5-2

Ethyl 2-(N-methylaminoacetylamino)-6,7-dimethoxytetralin-2-carboxylate was synthesized in the same manner as in

REFERENCE EXAMPLE 5-1.

Table 6 shows the structural formulas, physical properties and NMR spectra of these compounds.

TABLE 6

| Reference Example | Structural Formula | Melting Point (°C.) or Physical Property | $^1H-NMR(ppm, CDCl_3)$ |
|---|---|---|---|
| 5-1 | | oil | δ: 1.21(3H, t, J=7Hz), 2.00–2.20(1H, m), 2.30–2.50(1H, m), 2.53–2.88(4H, m), 2.92–3.20(3H, m), 3.67, 3.82(1H each, d, J=17.2Hz), 4.13(2H, q, J=7Hz), 6.85–7.20(4H, m), 8.55(1H, s) |
| 5-2 | | oil | δ: 1.22(3H, t, J=7Hz), 2.00–2.23(1H, m), 2.30–2.45(1H, m), 2.55–3.00(5H, m), 3.10, 3.32(1H each, d, J=17.2Hz), 3.60–4.00(10H, m), 6.56(2H, s), 8.48(1H, s) |

REFERENCE EXAMPLE 6-1

1'-Methylspiro[tetralin-2,3'-piperazine]-2',5'-dione

A solution of ethyl 2-(N-methylaminoacetylamino)tetralin-2-carboxylate (290 mg, 1.0 mmol) in a 1 N aqueous sodium hydroxide solution (2 ml)-tetrahydrofuran (10 ml) was stirred for 13 hours while heating at 80° C. After the reaction mixture was concentrated under reduced pressure, the residue was dissolved in ethyl acetate. This solution was washed by sequential additions of water and saturated saline, dried over anhydrous sodium sulfate, and concentrated under reduced pressure to yield 150 mg (61%) of the title compound as a crude crystal, a portion of which was then recrystallized from chloroform-isopropyl ether.

REFERENCE EXAMPLE 6-2

6,7-Dimethoxy-1'-methylspiro[tetralin-2,3'-piperazine]-2',5'-dione was synthesized in the same manner as in Reference Example 6-1.

Table 7 shows the structural formulas, physical properties and NMR spectra of these compounds.

TABLE 7

| Reference Example | Structural Formula | Melting Point (°C.) or Physical Property | $^1H-NMR(ppm, CDCl_3)$ |
|---|---|---|---|
| 6-1 | | 167–168 | δ: .1.99(1H, ddd, J=16.0, 6.0, 3.0Hz), 2.30(1H, ddd, J=16.0, 12.0, 8.0Hz), 2.78(1H, dd, J=16.6, 2.6Hz), 2.90–3.02)(2H, m) 3.05(3H, s), 3.63(1H, d, J=16.6Hz), 4.03(2H, ABq, J=17.6Hz), Δυ=29,8Hz), 6.13(1H br s), 7.02–7.20(4H, m) |
| 6-2 | | 168–169 | δ: 1.90–2.05(1H, m), 2.28(1H, ddd, J=13.2, 10.2, 8.8Hz), 2.69(1H, dd, J=16.6, 2.2Hz), 2.82–2.94(2H, m), 3.06(3H, s), 3.58(1H, d, J=16.4Hz), 3.85, 3.86(3H, each, s), 4.04(2H, ABq, J=18.0Hz, Δυ=30.4Hz), 6.11(14, br s), 6.53, 6.61(1H each, s) |

EXAMPLE 1-1

3,4-Dihydrospiro[naphthalene-2(1H),2'-piperidine]-1-one hydrochloride

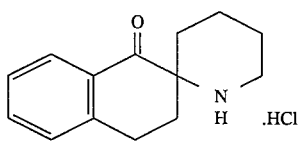

7.64 g of 1-benzoyl-2-(2-phenylethyl)-2-piperidinecarbonitrile as obtained in Reference Example 1 was dissolved in 250 ml of 1,2-dichloroethane. To this solution, 8.0 g of aluminum chloride was added, followed by thermal refluxing for 6 hours. After cooling, the reaction mixture was carefully poured over a 10% aqueous solution of sodium hydroxide and extracted with methylene chloride and water. The methylene chloride layer was dried over anhydrous magnesium sodium and filtered, after which the solvent was distilled off. To the residue, 100 ml of methanol and 100 ml of a 20% aqueous solution of sodium hydroxide were added, followed by thermal refluxing for 12 hours. After the reaction mixture was allowed to cool, the methanol was distilled off; the residue was extracted with methylene chloride and water. After the methylene chloride layer was dried over anhydrous sodium sulfate and filtered, the solvent was distilled off. The residue was purified by alumina column chromatography with ethyl acetate:hexane (1:2) as a developing solvent; the solution containing the desired product was distilled under reduced pressure; the residue was treated with 6.0 ml of 4 N-methanolic hydrochloric acid to yield a solid, which was then recrystallized from methylene chloride to yield 3.0 g of a colorless crystal.

Melting point: 222°–223° C.

¹H-NMR (ppm, CDCl₃): 1.37–1.85 (5H, m), 1.92–2.14 (3H, m), 2.44 (1H, dt, J=7 Hz, 5 Hz), 2.76–3.16 (4H, m), 7.20–7.52 (3H, m), 8.29 (1H, dd, J=8 Hz, 1 Hz)

Elemental analysis (for $C_{14}H_{18}ClNO·H_2O$): Calculated: C, 62.33; H, 7.47; N, 5.19 Found: C, 62.39; H, 7.27; N, 5.42

The following compounds were synthesized in the same manner as in Example 1-1 described hereinabove.

EXAMPLE 1-2

3,4-Dihydro-6-methoxyspiro[naphthalene-2(1H),2'-piperidine]-1-one hydrochloride

EXAMPLE 1-3

3,4-Dihydro-8-methoxyspiro[naphthalene-2(1H),2'-piperidine]-1-one hydrochloride

EXAMPLE 1-4

3,4-Dihydro-6,7-dimethoxyspiro[naphthalene-2(1H),2'-piperidine]-1-one hydrochloride

EXAMPLE 1-5

6,7-Dihydrospiro[benzo[b]thiophene-5(4H), 2'-piperidine]-4-one hydrochloride

EXAMPLE 1-6

4,5-Dihydrospiro[benzo[b]thiophene-6(7H),2'-piperidine]-7-one hydrochloride

EXAMPLE 1-7

1,3,4,5,6,7,3',4'-Octahydrospiro[2H-azepine-2,2'(1H)-naphthalene]-1'-one hydrochloride Table 8 and 9 show the structural formulas, physical properties and NMR spectra of these compounds.

TABLE 8

| Example | Structural Formula | (1) Melting Point (°C.) or Physical Property (2) Molecular Formula | (3) Elemental Analysis ① Calculated ② Found C | H | N | ¹H—NMR(ppm, CDCl₃) |
|---|---|---|---|---|---|---|
| 1-2 | (structure with CH₃O, ketone, spiro-piperidine·HCl) | (1) 249 (decomposed) (2) $C_{15}H_{20}ClNO_2$ | ① 63.94  7.15 ② 64.04  7.20 | | 4.97 5.03 | 1.31–1.88(6H, m), 1.89–2.10(1H, m), 2.16(1H, br s), 2.34–2.50(1H, m), 2.74–3.14(4H, m), 3.84(3H, s), 6.66(1H, d, J=3Hz), 6.82(1H, dd, J=9Hz, 3Hz), 7.99(1H, d, J=9Hz) |
| 1-3 | (structure with CH₃O, ketone, spiro-piperidine·HCl) | (1) 255–259 (decomposed) (2) $C_{15}H_{20}ClNO_2·1/4H_2O$ | ① 62.93  7.22 ② 63.02  7.08 | | 4.89 4.91 | 1.42–2.21(6H, m), 2.74–2.85(2H, m), 3.05–3.19(2H, m), 3.36–3.55(1H, m), 3.76–4.00(1H, m), 3.88(3H, s), 6.81(2H, t, J=8Hz), 7.42(1H, t, J=8Hz), 9.06(1H, br s) |
| 1-4 | (structure with CH₃O, CH₃O, ketone, spiro-piperidine·HCl) | (1) 255–259 (decomposed) (2) $C_{16}H_{22}ClNO_3·1/4H_2O$ | ① 60.75  7.17 ② 61.01  7.10 | | 4.43 4.51 | 1.33–1.85(5H, m), 1.93–2.10(1H, m), 2.35(1H, br s), 2.42(1H, t, J=5Hz), 2.50(1H, t, J=5Hz), 2.76–3.35 (4H, m), 3.92(3H, s), 3.93(3H, s), 6.64(1H, s), 7.50(1H, s) |

TABLE 9

| Example | Structural Formula | (1) Melting Point (°C.) or Physical Property (2) Molecular Formula | (3) Elemental Analysis ① Calculated ② Found C | H | N | ¹H—NMR(ppm, CDCl₃) |
|---|---|---|---|---|---|---|
| 1-5 | (structure with thiophene fused, ketone, spiro-piperidine·HCl) | (1) >280 (2) $C_{12}H_{16}ClNOS$ | ① 55.91  6.26 ② 55.78  6.26 | | 5.43 5.37 | 1.34–1.90(7H, m), 2.02–2.18(1H, m), 2.46–2.60(1H, m), 2.75–3.21(4H, m), 7.09(1H, d, J=5Hz), 7.37(1H, d, J=5Hz) |

TABLE 9-continued

| Example | Structural Formula | (1) Melting Point (°C.) or Physical Property (2) Molecular Formula | (3) Elemental Analysis ① Calculated ② Found | | | ¹H—NMR(ppm, CDCl₃) |
|---|---|---|---|---|---|---|
| | | | C | H | N | |
| 1-6 | [structure: benzo[b]thiophene fused cyclohexanone spiro piperidine · HCl] | (1) 275–277 (decomposed) (2) C₁₂H₁₆ClNOS | ① 55.91 ② 55.84 | 6.26 6.24 | 5.43 5.48 | 1.40–2.16(8H, m), 2.42–2.55(1H, m), 2.72–3.12(4H, m), 6.93(1H, d, J=5Hz), 7.61(1H, d, J=5Hz) |
| 1-7 | [structure: tetralone spiro azepane · HCl] | (1) 208–210 (2) C₁₆H₂₀ClNO·¼H₂O | ① 66.66 ② 66.77 | 7.65 7.50 | 5.18 5.00 | 1.20–1.84(7H, m), 1.87–2.30(4H, m), 2.55–2.71(1H, m), 2.93–3.08(3H, m), 7.21(1H, d, J=8Hz), 7.32(1H, d, J=8Hz), 7.46(1H, dt, J=8, 2Hz), 8.05(1H, dd, J=8, 2Hz) |

EXAMPLE 2-1

3,4-Dihydrospiro[naphthalene-2(1H), 2'-piperidine]-1-ol

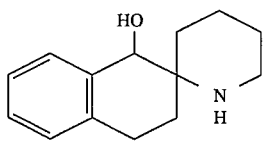

0.80 g of 3,4-dihydrospiro[naphthalene-2(1H),2'-piperidine]-1-one as obtained in Example 1 was dissolved in 20 ml of methanol. To this solution, 0.15 g of sodium borohydride was added little by little. After stirring for 30 minutes, water was added; the reaction mixture was extracted with methylene chloride. The methylene chloride layer was dried over anhydrous sodium sulfate and filtered, after which the solvent was distilled off. The resulting solid was recrystallized from methylene chloride-ether to yield 0.25 g of a white crystal.

Melting point: 125°–127° C.

¹H-NMR (ppm, CDCl₃): 1.32–1.98 (8H, m), 2.28 (1H, quint, s), 7.07–7.28 (4H, J=7 Hz), 2.74–2.94 (4H, m), 4.37 (1H, m), 7.40–7.52 (1H, m)

Elemental analysis (for C₁₄H₁₉NO): Calculated: C, 77.38; H, 8.81; N, 6.45 Found: C, 77.16; H, 8.84; N, 7.01

The following compounds were synthesized in the same manner as in Example 2-1 described hereinabove.

EXAMPLE 2-2

3,4-Dihydro-6-methoxyspiro[naphthalene-2(1H),2'-piperidine]-1-ol

EXAMPLE 2-3

3,4-Dihydro-6,7-dimethoxyspiro[naphthalene-2(1H), 2'-piperidine]-1-ol hydrochloride

EXAMPLE 2-4

6,7-Dihydrospiro[benzo[b]thiophene-5-(4H),2'-piperidine]-4-ol hydrochloride

Table 10 shows the structural formulas, physical properties and NMR spectra of these compounds.

TABLE 10

| Example | Structural Formula | (1) Melting Point (°C.) or Physical Property (2) Molecular Formula | (3) Elemental Analysis ① Calculated ② Found | | | ¹H—NMR(ppm, CDCl₃) |
|---|---|---|---|---|---|---|
| | | | C | H | N | |
| 2-2 | [structure: 6-methoxy tetrahydronaphthalenol spiro piperidine] | (1) 132–134 (2) C₁₅H₂₁NO₂ | ① 72.84 ② 72.85 | 8.56 8.62 | 5.66 5.66 | 1.33–1.87(9H, m), 2.06–2.22(1H, m), 2.74–2.89(4H, m), 3.78(3H, s), 4.31(1H, s), 6.64(1H, d, J=3Hz), 6.67(1H, dd, J=9Hz, 3Hz), 7.33(1H, d, J=9Hz) |

TABLE 10-continued

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 2-3 | CH$_3$O, CH$_3$O, HO, N-H .HCl | (1) 213–216 (decomposed) (2) C$_{16}$H$_{24}$ClNO$_3$·1/5H$_2$O | ① 60.54 ② 60.76 | 7.75 7.69 | 4.41 4.49 | 1.36–1.80(8H, m), 2.03–2.24(2H, m), 2.73(2H, t, J=7Hz), 2.80–2.90(2H, m), 3.84(3H, s), 3.86(3H, s;), 4.28(1H, s), 6.59(1H,s), 6.95(1H,s) |
| 2-4 | HO, S, N-H .HCl | (1) 215–221 (decomposed) (2) C$_{12}$H$_{18}$ClNOS | ① 55.48 ② 55.15 | 6.98 6.92 | 5.39 5.34 | 1.33–1.94(9H, m), 2.16(1H, quint, J=8Hz), 2.72–2.93(4H, m), 4.38(1H, s), 6.99(1H, d, J=5Hz), 7.13(1H, d, J=5Hz) |

EXAMPLE 3-1

3,4-Dihydrospiro[naphthalene-2(1H),2'-piperidine]hydrochloride

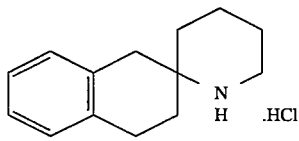

(1) To 200 ml of a methylene chloride solution of 3.36 g of 3,4-dihydrospiro[naphthalene-2(1H),2'-piperidine]-1-one as obtained in Example 1-1, 2.6 g of potassium carbonate was added, followed by dropwise addition of 50 ml of a methylene chloride solution of 3.4 ml of trifluoroacetic anhydride at 0° C. After stirring for 3 hours, water was added; the reaction mixture was extracted with methylene chloride. The methylene chloride layer was dried over anhydrous sodium sulfate and filtered, after which the solvent was distilled off. The residue was purified by silica gel column chromatography with ethyl acetate:hexane (1:2) as a developing solvent; the solution containing the desired product was distilled under reduced pressure. The resulting solid was recrystallized from ethyl acetate-hexane to yield 4.86 g of 1'-trifluoroacetyl-3,4-dihydrospiro[naphthalene-2(1H),2'-piperidine]-1-one as a colorless needle.

Melting point: 97°–100° C.

1H-NMR (ppm, CDCl$_3$): 1.60–2.25 (7H, m), 2.67–3.16 (3H, m), 3.35–3.53 (1H, m), 3.82–3.98 (1H, m), 7.16–7.52 (3H, m), 8.20 (1H, dd, J=8 Hz, 1.2 Hz)

Elemental analysis (for C$_{16}$H$_{16}$F$_3$NO$_2$) Calculated: C, 61.73; H, 5.18; N, 4.50 Found: C, 61.47; H, 5.20; N, 4.40

(2) 4.44 g of 1'-trifluoroacetyl-3,4-dihydrospiro [naphthalene-2(1H),2'-piperidine]-1-one was dissolved in 30 ml of acetic acid, followed by 6.5 hours of catalytic reduction at 4 kg/cm$^2$ and 80° C. in the presence of 0.76 g of 10% palladium-carbon catalyst. The reaction mixture was poured over water, alkalinized with a 10% aqueous solution of sodium hydroxide, and extracted with methylene chloride. The methylene chloride layer was dried over anhydrous sodium sulfate and filtered, after which the solvent was distilled off. The residue was treated with 3.6 ml of 4 N-methanolic hydrochloric acid to yield a solid, which was then recrystallized from methylene chloride-ether to yield 2.51 g of a white crystal.

Melting point: 200°–202° C.

$^1$H-NMR (ppm, CDCl$_3$): 1.43–1.80 (8H, m), 1.84–2.02 (1H, m), 2.77 (2H, s), 2.84 (4H, t, J=5 Hz), 7.10 (4H, s)

Elemental analysis (for C$_{14}$H$_{20}$ClN.¼H$_2$O): Calculated: C, 69.40; H, 8.53; N, 5.78 Found: C, 69.62; H, 8.38; N, 5.64

EXAMPLE 3-2

1,3,4,5,6,7,1',2',3',4'-Octahydrospiro[2H-azepine-2,2'(1H)naphthalene]hydrochloride This compound was synthesized in the same manner as in Example 3-1 described hereinabove.

Table 11 shows the structural formulas, physical properties and NMR spectra of this compound.

TABLE 11

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 3-2 | 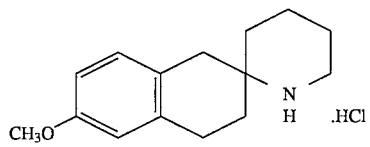 | (1) 191–194 (2) C$_{15}$H$_{22}$ClN· 1/4H$_2$O | ① 70.29 ② 70.36 | 8.85 8.68 | 5.46 5.31 | 1.08–1.92(11H, m), 2.60–2.98(6H, m), 7.01–7.13(4H, m) |

EXAMPLE 4-1

3,4-Dihydro-6-methoxyspiro[naphthalene-2(1H),2'-piperidine]hydrochloride 6.57 g of 3,4-dihydro-6-methoxyspiro[naphthalene-2(1H),2'-piperidine]-1-ol as obtained in Example 2-2 was dissolved in 30 ml of trifluoroacetic acid. TO this solution, 8.5 ml of triethylsilane was added, followed by stirring for 1 hour. The reaction mixture was poured over water little by little; 1N hydrochloric acid was added; the mixture was washed with hexane. The water layer was alkalinized by the addition of a 1N aqueous solution of sodium hydroxide and extracted with methylene chloride. The methylene chloride layer was dried over anhydrous sodium sulfate and filtered, after which the solvent was distilled off. The residue was treated with 7.0 ml of 4 N-methanolic hydrochloric acid to yield a solid, which was then recrystallized from methanol-ether to yield 5.09 g of a white crystal.

Melting point: 201°–203° C.

$^1$H-NMR (ppm, CDCl$_3$): 1.31–2.00 (9H, m), 2.71 (2H, s), 2.74–2.88 (4H, m), 3.77 (3H, m), 6.62–6.73 (2H, m), 6.98 (1H, m)

Elemental analysis (for C$_{15}$H$_{22}$ClNO.+e,fra /5+ee H$_2$O): Calculated: C, 66.38; H, 8.32; N, 5.16 Found: C, 66.65; H, 8.46; N, 5.03

The following compounds were synthesized in the same manner as in Example 4-1 described hereinabove.

EXAMPLE 4-2

3,4-Dihydro-6,7-dimethoxyspiro[naphthalene-2(1H),2'-piperidine]hydrochloride

EXAMPLE 4-3

3,4-Dihydro-8-methoxyspiro[naphthalene-2(1H),2'-piperidine]hydrochloride

EXAMPLE 4-4

6,7-Dihydrospiro[benzo[b]thiophene-5(4H),2'-piperidine]hydrochloride

EXAMPLE 4-5

4,5-Dihydrospiro[benzo[b]thiophene-6(7H),2'-piperidine] hydrochloride

Table 12 shows the structural formulas, physical properties and NMR spectra of these compounds.

TABLE 12

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 4-2 | | (1) 205–208 (2) C$_{16}$H$_{24}$ClNO$_2$ | ① 64.53 ② 64.20 | 8.12 8.13 | 4.70 4.66 | 1.39–2.00(9H, m), 2.63–2.28(6H, m), 3.83(6H, s), 6.55(1H, s), 6.59(1H, s) |
| 4-3 | | (1) 239–241 (2) C$_{15}$H$_{22}$ClNO | ① 67.28 ② 67.28 | 8.28 8.15 | 5.23 5.16 | 1.40–1.74(8H, m), 1.81–1.98(1H, m), 2.53–2.96(6H, m), 3.81(3H, s), 6.66(1H, d, J=8Hz,), 6.73(1H, d, J=8Hz), 7.09(1H, d, J=8Hz) |

TABLE 12-continued

| Example | Structural Formula | (1) Melting Point (°C.) or Physical Property (2) Molecular Formula | (3) Elemental Analysis ① Calculated ② Found | | | $^1$H−NMR(ppm, CDCl$_3$) |
|---|---|---|---|---|---|---|
| | | | C | H | N | |
| 4-4 | | (1) 212–220 (2) C$_{12}$H$_{18}$ClNS | ① 59.12 ② 58.96 | 7.44 7.09 | 5.75 5.38 | 1.43–2.07(9H, m), 2.65(2H, d, J=89Hz), 2.72–2.90(4H, m), 6.73(1H, d, J=5Hz), 7.08(1H, d, J=5Hz) |
| 4-5 | | (1) 197–203 (2) C$_{12}$H$_{18}$ClNS | ① 59.12 ② 58.90 | 7.44 7.39 | 5.75 5.69 | 1.44–2.02(9H, m), 2.61–2.94(6H, m), 6.76(1H, d, J=5Hz), 7.07(1H, d, J=5Hz) |

EXAMPLE 5-1

3,4-Dihydro-1'-propylspiro[naphthalene-2(1H),2'-piperidine]hydrochloride

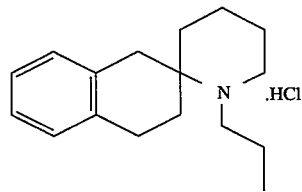

0.41 g of 3,4-dihydrospiro[naphthalene-2(1H),2'-piperidine]as obtained in Example 3-1 was dissolved in 5 ml of N,N-dimethylformamide. To this solution, 0.35 g of, potassium carbonate and 0.22 ml of n-propyl iodide were added, followed by stirring at room temperature for 12 hours. Water was added; the reaction mixture was extracted with ethyl acetate and washed with water and saturated saline. The extract was dried over anhydrous sodium sulfate and filtered, after which the solvent was distilled off. The residue was purified by alumina column chromatography; the solution containing the desired product was distilled under reduced pressure. The residue was treated with 0.6 ml of 4 N-methanolic hydrochloric acid to yield a solid, which was then recrystallized from methylene chloride-ether to yield 0.48 g of a white crystal.

Melting point: 171°–176° C.

$^1$H-NMR (ppm, CDCl$_3$): 0.86 (3H, t, J=7 Hz), 1.34–2.01 (10H, m), 2.21–2.48 (2H, m), 2.65 (2H, t, J=7 Hz), 2.70–2.96 (4H, m), 7.08 (4H, s)

Elemental analysis (for C$_{17}$H$_{26}$ClN.½H$_2$O): Calculated: C, 70.69; H, 9.42; N, 4.85 Found: C, 70.64; H, 9.22; N, 5.05

The following compounds were synthesized in the same manner as in Example 5-1 described hereinabove.

EXAMPLE 5-2

3,4-Dihydro-1'-methylspiro[naphthalene-2(1H),2'-piperidine]hydrochloride

EXAMPLE 5-3

1'-Ethyl-3,4-dihydrospiro[naphthalene-2(1H),2'-piperidine]hydrochloride

EXAMPLE 5-4

3,4-Dihydro-1'-(4-phthalimidebutyl)spiro[naphthalene(1H),2'-piperidine] hydrochloride

EXAMPLE 5-5

3,4-Dihydro-6-methoxy-1-propylspiro[naphthalene-2(1H),2'-piperidine]hydrochloride

EXAMPLE 5-6

3,4-Dihydro-6-methoxy-1-methylspiro[naphthalene-2(1H),2'-piperidine]hydrochloride

EXAMPLE 5-7

3,4-Dihydro-6-methoxy-1'-phenylmethylspiro[naphthalene-2(1H), 2'-piperidine]hydrochloride

EXAMPLE 5-8

3,4-Dihydro-6-methoxy-1'-(2-phenylethyl)spiro[naphthalene-(1H),2'-piperidine] hydrochloride

EXAMPLE 5-9

3,4-Dihydro-6-methoxy-1'-(3-phenylpropyl)spiro[naphthalene-(1H),2'-piperidine] hydrochloride

EXAMPLE 5-10

3,4-Dihydro-6-methoxy-1'-(2-phenoxyethyl)spiro[naphthalene-(1H),2'-piperidine] hydrochloride

EXAMPLE 5-11

3,4-Dihydro-6-methoxy-1'-(4-phthalimidebutyl)spiro[naphthalene-2(1H),2'-piperidine]hydrochloride

EXAMPLE 5-12

3,4-Dihydro-6-methoxy-1'-(3-phthalimidepropyl)spiro[naphthalene-2(1H),2'-piperidine]hydrochloride

EXAMPLE 5-13

{3,4-Dihydro-6-methoxyspiro[naphthalene-2(1H),2'-piperidine]}-1'-ylacetamide hydrochloride

EXAMPLE 5-14

3,4-Dihydro-6-methoxy-1'-[3-(1-phenylmethylpiperidin-4yl)propyl]spiro[naphthalene-2(1H),2'-piperidine] dihydrochloride

EXAMPLE 5-15

3,4-Dihydro-8-methoxy-1'-(3-phenylpropyl)spiro[naphthalene-(1H),2'-piperidine] hydrochloride

EXAMPLE 5-16

3,4-Dihydro-6,7-dimethoxy-1'-propylspiro[naphthalene-(1H),2'-piperidine] hydrochloride

EXAMPLE 5-17

6,7-Dihydro-1'-propylspiro[benzo[b]thiophene-5(4H),2'-piperidine] hydrochloride

EXAMPLE 5-18

6,7-Dihydro-1'-propylspiro[benzo[b]thiophene-6(7H),2'-piperidine] hydrochloride

EXAMPLE 5-19

1,3,4,5,6,7,3',4'-Octahydro-1-propylspiro[2H-azepine-2', 2(1H)-naphthalene] hydrochloride

EXAMPLE 5-20

3,4-Dihydro-6,7-dimethoxy-1'-(3,3diphenylpropyl)spiro[naphthalene-2(1H),2'-piperidine] hydrochloride

EXAMPLE 5-21

3,4-Dihydro-6-methoxy-1'-(3,3diphenylpropyl)spiro[naphthalene-2(1H),2'-piperidine] hydrochloride

EXAMPLE 5-22

3,4-Dihydro-6-methoxy-1'-(4,4-diphenylbutyl)spiro[naphthalene-2(1H),2'-piperidine] hydrochloride

EXAMPLE 5-23

3,4-Dihydro-6-dimethoxy-1'-(4,4-diphenylbutyl)spiro[naphthalene-2(1H),2'-piperidine] hydrochloride

EXAMPLE 5-24

3,4-Dihydro-1'-(3,3-diphenylpropyl)spiro[naphthalene-2(1H),2'-piperidine] hydrochloride

EXAMPLE 5-25

3,4-Dihydro-1'-(4,4-diphenylbutyl)spiro[naphthalene-2(1H), 2'-piperidine] hydrochloride

EXAMPLE 5-26

4,5-Dihydro-1'-(3,3-diphenylpropyl)spiro[benzo[b]thiophene-6(7H),2'-piperidine] hydrochloride

EXAMPLE 5-27

4,5-Dihydro-1'-(4,4-diphenylbutyl)spiro[benzo[b]thiophene-6(7H),2'-piperidine] hydrochloride

EXAMPLE 5-28

3,4-Dihydro-6,7-dimethoxy-1'-phenylmethylspiro[naphthalene-2(1H), 2'-piperidine]

Tables 13 to 19 show the structural formulas, physical properties and NMR spectra of these compounds.

TABLE 13

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 5-2 | [structure] | (1) Noncrystalline powder (2) C$_{15}$H$_{22}$ClNO·1/2H$_2$O | ① 69.08 ② 69.32 | 8.89 8.88 | 5.37 5.21 | 1.39–1.78(7H, m), 1.88–2.06(1H, m), 2.32(3H, s), 2.58–2.72(3H, m), 2.75–2.87(2H, m), 2.97 (1H, d, J=16Hz), 7.09(4H, S) |
| 5-3 | [structure] | (1) 191–196 (2) C$_{16}$H$_{24}$ClNO·1/4H$_2$O | ① 71.09 ② 70.93 | 9.14 8.93 | 5.18 5.27 | 1.06(3H, t, J=7Hz), 1.43–2.00(8H, m), 2.32–2.97(8H, m), 7.09 (4H, s) |
| 5-4 | [structure] | (1) Noncrystalline powder (2) C$_{26}$H$_{31}$ClN$_2$O$_2$·H$_2$O | ① 68.33 ② 68.27 | 7.28 7.37 | 6.13 5.83 | 1.21–1.97(12H, m), 2.28–2.54(2H, m), 2.54–2.92(6H, m), 3.69(2H, t, J=7Hz), 7.07(4H, s), 7.65–7.75(2H, m), 7.78–7.87 (2H, m) |

TABLE 13-continued

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 5-5 | [structure: 6-methoxy-tetrahydronaphthalene spiro-piperidine with N-propyl, ·HCl] | (1) 145–148 (2) C$_{18}$H$_{28}$ClNO | ① 69.77 ② 69.75 | 9.11 9.21 | 4.52 4.45 | 0.86(3H, t, J=7Hz), 1.32–1.97 (10H, m), 2.22–2.46(2H, m), 2.54–2.88(6H, m), 3.77 (3H, s), 6.63–6.75 (2H, m) 6.99(1H, d, J=8Hz) |
| 5-6 | [structure: 6-methoxy-tetrahydronaphthalene spiro-piperidine with N-CH$_3$, ·HCl] | (1) 202–205 (2) C$_{16}$H$_{24}$ClNO· 1/4H$_2$O | ① 67.11 ② 66.84 | 8.63 8.60 | 4.89 5.35 | 1.35–1.77(7H, m), 1.86–2.06(1H, m), 2.32(3H, s), 2.53–2.96(6H, m), 3.77 (3H, s), 6.64(1H, s) 6.68(1H, dd, J=8Hz, 2Hz), 6.99(1H, d, J=8Hz) |

TABLE 14

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 5-7 | [structure: 6-methoxy-tetrahydronaphthalene spiro-piperidine with N-benzyl, ·HCl] | (1) 148–151 (2) C$_{22}$H$_{28}$ClNO· H$_2$O | ① 70.29 ② 70.48 | 8.04 7.95 | 3.73 | 1.37–2.10(8H, 4.18 m), 2.48–2.98 (6H, m), 3.40–3.82(2H, m), 3.77(3H, s), 6.66(1H, s), 6.70(1H. d. J=3Hz). 6.99 (1H. d. J=8Hz). 7.13–7.14 (5H. m) |
| 5-8 | [structure: 6-methoxy-tetrahydronaphthalene spiro-piperidine with N-CH$_2$-benzyl, ·HCl] | (1) 142–144 (2) C$_{23}$H$_{30}$ClNO· 1/4H$_2$O | ① 73.38 ② 73.33 | 8.17 8.11 | 3.72 | 1.38–1.95(8H, 3.75 m), 2.52–2.82 (10H, m), 3.76 (3H, s), 6.59–6.71(2H, m), 6.95(1H. d. J=8Hz), 7.12–7.32(5H, m) |
| 5-9 | [structure: 6-methoxy-tetrahydronaphthalene spiro-piperidine with N-(CH$_2$)$_2$-phenyl, ·HCl] | (1) 156–157 (2) C$_{24}$H$_{32}$ClNO· 1/4H$_2$O | ① 73.82 ② 74.10 | 8.39 8.30 | 3.59 | 1.42–1.94 3.65 (10H, m), 2.30–2.83 (10H, m), 3.76(3H, s), 6.69–6.71(2H, m), 6.95(1H, d, J=8Hz), 7.10–7.31(5H, m) |

TABLE 14-continued

| Example | Structural Formula | (1) Melting Point (°C.) or Physical Property (2) Molecular Formula | (3) Elemental Analysis ① Calculated ② Found C / H / N | $^1$H—NMR (ppm, CDCl$_3$) |
|---|---|---|---|---|
| 5-10 | (6-methoxy-tetrahydronaphthalene-spiro-piperidine)-N-CH$_2$CH$_2$-O-phenyl · HCl | (1) 181–184<br>(2) C$_{23}$H$_{30}$ClNO$_2$·1/4H$_2$O | ① 70.39  7.83  3.57<br>② 70.39  7.77 | 1.42–1.98(8H, m), 2.61–2.98 (8H, m), 3.76 (3H, s), 3.98 (2H, t, J=6Hz), 6.61–6.72(2H, m), 6.84–7.00 (4H, m), 7.20–7.31(2H, m) |
| 5-11 | (6-methoxy-tetrahydronaphthalene-spiro-piperidine)-N-(CH$_2$)$_4$-phthalimide · HCl | (1) Noncrystalline powder<br>(2) C$_{27}$H$_{33}$ClN$_2$O$_3$·2H$_2$O | ① 64.21  7.38  5.55<br>② 63.77  7.10  5.46 | 1.34–1.98 (12H, m), 2.30–2.87(8H, m), 3.69(2H, t, J=7Hz), 3.76(3H, s), 6.61–6.73(2H, m), 6.99(1H, d, J=8Hz), 7.68–7.76(2H, m), 7.79–7.89 (2H, m) |

TABLE 15

| Example | Structural Formula | (1) Melting Point (°C.) or Physical Property (2) Molecular Formula | (3) Elemental Analysis ① Calculated ② Found C / H / N | $^1$H—NMR(ppm, CDCl$_3$) |
|---|---|---|---|---|
| 5-12 | (6-methoxy-tetrahydronaphthalene-spiro-piperidine)-N-(CH$_2$)$_2$-phthalimide · HCl | (1) Noncrystalline powder<br>(2) C$_{26}$H$_{31}$ClN$_2$O$_3$·H$_2$O | ① 66.02  7.03  5.92<br>② 65.87  6.83  6.02 | 1.34–1.96(10H, m), 2.34–2.82(8H, m), 3.62–3.78(2H, m), 3.76(3H, s), 6.58–6.68(2H, m), 6.95(1H, d, J=8Hz), 7.63–7.74(2H, m), 7.77–7.86(2H, m) |
| 5-13 | (6-methoxy-tetrahydronaphthalene-spiro-piperidine)-N-CH$_2$-CONH$_2$ · HCl | (1) 191–194<br>(2) C$_{17}$H$_{25}$ClNO$_2$O$_2$·2/5H$_2$O | ① 61.49  7.83  8.44<br>② 61.63  7.81  8.12 | 1.37–1.97(8H, m), 2.63–2.82(6H, m), 3.02(1H, d, J=17Hz), 3.17(1H, d, J=17Hz), 3.76(3H, s), 6.34(1H, br d, J=4Hz), 6.60–6.75(2H, m), 6.96(1H, d, J=8Hz), 7.36(1H, br d, J=4Hz) |

TABLE 15-continued

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 5-14 | [structure: 6-methoxy-tetrahydronaphthalene spiro piperidine with ethyl-piperidinyl-N-benzyl substituent, ·2HCl] | (1) 241–245 (2) C$_{30}$H$_{44}$Cl$_2$N$_2$O·H$_2$O | ① 67.02 ② 67.14 | 8.62 8.47 | 5.21 5.16 | 1.09–1.98(17H, m), 2.17–2.94(12H, m), 3.48(2H, s), 3.77(3H, s), 6.61–6.72(2H, m), 6.98(1H, d, J=8Hz), 7.25–7.37(5H, m) |
| 5-15 | [structure: 8-methoxy-tetrahydronaphthalene spiro piperidine with phenethyl group, ·HCl] | (1) Noncrystalline powder (2) C$_{24}$H$_{32}$ClNO·1/2H$_2$O | ① 72.98 ② 72.87 | 8.42 8.34 | 3.55 3.37 | 1.34–1.97(10H, m), 2.36–2.92(10H, m), 3.81(3H, s), 6.65(1H, d, J=8Hz), 6.70(1H, d, J=8Hz), 7.02–7.31(6H, m) |
| 5-16 | [structure: 6,7-dimethoxy-tetrahydronaphthalene spiro piperidine with propyl group, ·HCl] | (1) 212–214 (2) C$_{19}$H$_{30}$ClNO$_2$ | ① 67.14 ② 66.77 | 8.90 8.87 | 4.12 4.08 | 0.86(3H, t, J=7Hz), 1.22–2.06(10H, m), 2.20–2.51(2H, m), 2.54–2.92(6H, m), 3.84(6H, s), 6.58(2H, s) |

TABLE 16

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 5-17 | [structure: thiophene-fused cyclohexane spiro piperidine with propyl group, ·HCl] | (1) 218–223 (2) C$_{15}$H$_{24}$ClNS | ① 63.02 ② 62.73 | 8.46 8.35 | 4.90 4.85 | 0.86(3H, t, J=7Hz), 1.34–1.67(8H, m), 1.70–1.84(1H, m), 1.90–2.10(1H, m), 2.20–2.55(2H, m), 2.55–2.96(6H, m), 6.72(1H, d, J=5Hz), 7.06(1H, d, J=5Hz) |
| 5-18 | [structure: isomeric thiophene-fused cyclohexane spiro piperidine with propyl group, ·HCl] | (1) 192–195 (2) C$_{15}$H$_{24}$ClNS | ① 63.02 ② 62.77 | 8.46 8.66 | 4.90 4.92 | 0.87(3H, t, J=7Hz), 1.35–1.83(9H, m), 1.88–2.11(1H, m), 2.16–2.34(1H, m), 2.44–2.89(7H, m), 6.72(1H, d, J=5Hz), 7.04(1H, d, J=5Hz) |

TABLE 16-continued

| Example | Structural Formula | (1) Melting Point (°C.) or Physical Property (2) Molecular Formula | (3) Elemental Analysis ① Calculated ② Found | | | ¹H—NMR (ppm, CDCl₃) |
|---|---|---|---|---|---|---|
| | | | C | H | N | |
| 5-19 | (structure) ·HCl | (1) Noncrystalline Powder (2) C₁₈H₂₈ClN· 1/2H₂O | ① 71.88 ② 71.55 | 9.65 10.01 | 4.62 4.69 | 0.86(3H, t, J=7Hz), 1.30–1.91(12H, m), 2.24–2.62(4H, m), 2.71–2.97(4H, m), 7.08(4H, s) |
| 5-20 | (structure) ·HCl | (1) Noncrystalline Powder (2) C₃₁H₃₈ClNO₂· 3/2H₂O | ① 71.72 ② 71.81 | 7.96 7.77 | 2.70 2.62 | 1.40–1.67(8H, m), 2.13–2.71(10H, m), 3.81(6H, s), 3.96(1H, t, J=7Hz), 6.45(1H, s), 6.53(1H, s), 6.98–7.31(10H, m) |

TABLE 17

| Example | Structural Formula | (1) Melting Point (°C.) or Physical Property (2) Molecular Formula | (3) Elemental Analysis ① Calculated ② Found | | | ¹H—NMR (ppm, CDCl₃) |
|---|---|---|---|---|---|---|
| | | | C | H | N | |
| 5-21 | (structure) ·HCl | (1) Noncrystalline Powder (2) C₃₀H₃₆ClNO· 5/4H₂O | ① 74.36 ② 74.27 | 8.01 7.94 | 2.89 2.78 | 1.34–1.76(8H, m), 212–246(4H, m), 2.52–2.73(6H, m), 3.75(3H, s), 3.96(1H, t, J=7Hz), 6.56–6.67 (2H, m), 6.83(1H, d, J=8Hz), 7.10–7.34 (10H, m) |
| 5-22 | (structure) ·HCl | (1) Noncrystalline Powder (2) C₃₁H₃₈ClNO· 5/4H₂O | ① 74.67 ② 74.67 | 8.19 8.08 | 2.81 2.76 | 1.30–1.62(9H, m), 1.76–2.10(3H, m), 2.26–2.83(8H, m), 3.77(3H, s), 3.88(1H, t, J=7Hz), 6.61–6.74 (2H, m), 6.96(1H, d, J=8Hz), 7.10–7.34 (10H, m) |

TABLE 17-continued

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 5-23 | MeO, MeO-substituted spiro tetrahydronaphthalene-piperidine with N-(4,4-diphenylbutyl)·HCl | (1) 229–231 (dec.) (2) C$_{32}$H$_{40}$ClNO$_2$·1/2H$_2$O | ① 74.61 ② 74.70 | 8.02 7.78 | 2.72 2.62 | 1.31–1.72(7H, m), 1.76–2.10(3H, m), 2.30–2.85(10H, m), 3.83(3H, s), 3.84(3H, s), 3.89(1H, t, J=8Hz), 6.55(1H, s), 6.58(1H, s), 7.10–7.32(10H, m) |

TABLE 18

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 5-24 | spiro tetrahydronaphthalene-piperidine with N-(4,4-diphenylbutyl)·HCl | (1) Noncrystalline Powder (2) C$_{29}$H$_{34}$ClN·3/4H$_2$O | ① 78.18 ② 74.48 | 8.03 8.07 | 3.14 2.99 | 1.37–1.80(8H, m), 2.13–2.46(4H, m), 2.57–2.75(6H, m), 3.96(1H, t, J=7Hz), 6.87–7.37(14H, m) |
| 5-25 | spiro tetrahydronaphthalene-piperidine with N-(5,5-diphenylpentyl)·HCl | (1) Noncrystalline Powder (2) C$_{30}$H$_{36}$ClN·H$_2$O | ① 77.64 ② 77.89 | 8.25 7.97 | 3.02 2.88 | 1.30–2.09(14H, m), 2.25–2.90 (6H, m), 3.89(1H, t, J=7Hz), 7.03–7.35(14H, m) |

TABLE 18-continued

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 5-26 | (thiophene-fused spiro piperidine with N-CH$_2$CH$_2$CH(Ph)$_2$ ·HCl) | (1) 165–167<br>(2) C$_{27}$H$_{32}$ClNS·1/2H$_2$O | ① 72.54<br>② 72.91 | 7.44<br>7.21 | 3.13<br>3.24 | 1.35–1.83(8H, m), 2.14–2.83 (10H, m), 3.96(1H,t, J=7Hz), 6.68(1H, d, J=5Hz), 7.01(1H, d, J=5Hz), 7.09–7.32(10H, m) |

TABLE 19

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 5-27 | (thiophene-fused spiro piperidine with N-(CH$_2$)$_3$CH(Ph)$_2$ ·HCl) | (1) Noncrystalline Powder<br>(2) C$_{28}$H$_{34}$ClNS·1/4H$_2$O | ① 73.65<br>② 73.27 | 7.62<br>7.59 | 3.07<br>2.93 | 1.30–1.71(10H, m), 1.85–2.83(10H, m), 3.90(1H, t, J=8Hz), 6.71(1H, d, J=5Hz), 7.04(1H, d, J=5Hz), 7.09–7.32(10H, m) |
| 5-28 | (6,7-dimethoxy-3,4-dihydronaphthalene-2-spiro-2'-piperidine, N-benzyl) | Oil | | | | 1.53(6H, br), 1.70–2.08(2H, m), 2.52–2.98(6H, m), 3.50–3.76(2H, m), 3.83(6H, s), 6.57(1H, s), 6.60(1H, s), 6.60(1H, s), 7.19–7.38(5H, m) |

EXAMPLE 6-1

3,4-Dihydro-6-methoxy-1'-[4-(3-methoxyphenyl)piperazine-1-yl]acetylspiro[naphthalene-2(1H),2'-piperidine]hydrochloride

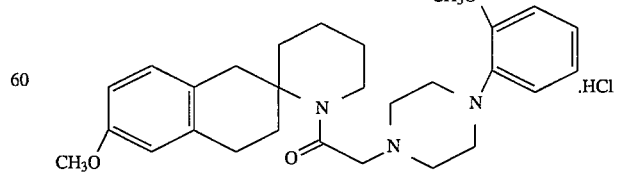

0.20 g of 3,4-dihydro-6-methoxyspiro[naphthalene-(1H), 2'-piperidine] as obtained in Example 4-1 was dissolved in 10 ml of methylene chloride. To this solution, a solution of 0.16 ml of triethylamine and 0.06 ml of chloroacetyl chloride in 5 ml of methylene chloride was added drop by drop at 0° C., followed by stirring at room temperature for 2 hours. Water was added; the reaction mixture was extracted with methylene chloride. The extract was dried over anhydrous sodium sulfate and filtered, after which the solvent was distilled off. The residue was dissolved in 5 ml of N,N-dimethylformamide. To this solution, 0.16 g of potassium carbonate and 0.18 g of 3-methoxyphenylpiperazine hydrochloride were added, followed by stirring at room temperature for 12 hours. Water was added; the reaction mixture was extracted with ethyl acetate and washed with water and saturated saline. The extract was dried over anhydrous sodium sulfate and filtered, after which the solvent was distilled off. The residue was purified by alumina column chromatography with ethyl acetate:hexane (1:2) as a developing solvent; the solution containing the desired product was distilled under reduced pressure. The residue was treated with 0.2 ml of 4 N-methanolic hydrochloric acid to yield a solid, which was then recrystallized from methylene chloride-ethyl acetate to yield 0.16 g of a white crystal.

Melting point: 171°–173° C.

$^1$H-NMR (ppm, CDCl$_3$): 1.51–1.83 (6H, m), 2.52–3.21 ( 15H, m), 3.52–3.63 (2H, m), 3.75 (3H, s), 3.85 (3H, s), 3.96 (1H, d, J=15 Hz), 6.61–6.70 (2H, m), 6.82–7.04 ( 5H, m)

Elemental analysis (for $C_{28}H_{38}ClN_3O_3 \cdot \frac{1}{4}H_2O$): Calculated: C, 66.65; H, 7.69; N, 8.33 Found: C, 66.67; H, 7.70; N, 8.56

The following compound was synthesized in the same manner as in Example 6-1 described hereinabove.

EXAMPLE 6-2

3,4-Dihydro-6-methoxy-1'-piperidinoacetylspiro[naphthalene-2(1H),2'-piperidine] hydrochloride Table 20 shows the structural formula, physical properties and NMR spectrum of this compound.

TABLE 20

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 6-2 | (structure with CH$_3$O-naphthalene-spiro-piperidine-N-C(O)-CH$_2$-N-piperidine · HCl) | (1) 207–210 (decomposed) (2) $C_{22}H_{33}ClN_2O_2 \cdot H_2O$ | ① 64.29 ② 64.42 | 8.58 8.66 | 6.82 6.72 | 1.30–1.78(14H, m), 2.26–2.40 (4H, m), 2.48–3.14(5H, m), 3.48–3.62(2H, m), 3.76(3H, s), 3.95(1H, d, J=15Hz), 6.57–6.69(2H, m), 6.95(1H, d, J=8Hz) |

EXAMPLE 7-1

3,4-Dihydro-6-methoxy-1'-[2-(4-(3-methoxyphenyl)piperazine-1-yl)ethyl]spiro[naphthalene-2(1H),2'-piperidine] dihydrochloride

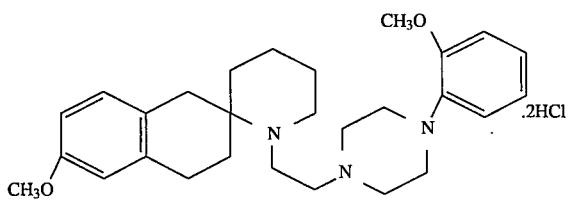

0.11 g of 3,4-dihydro-6-methoxy-1'-[4-(3-methoxyphenyl)piperazine-1-yl]acetylspiro[naphthalene-2(1H),2'-piperidine] as obtained in Example 6-1 was dissolved in 5 ml of tetrahydrofuran. To this solution, 0.026 g of lithium aluminum hydride was added, followed by stirring at room temperature for 2 hours. Water was added to hydrolyze excess lithium aluminum hydride; the reaction mixture was dried over anhydrous sodium sulfate and filtered, after which the solvent was distilled off. The residue was treated with 0.1 ml of 4N-methanolic hydrochloric acid to yield 0.088 g of a noncrystalline powder.

$^1$H-NMR (ppm, CDCl$_3$): 1.40–2.00 (6H, m), 2.46–2.87 (16H, m), 3.08 (4H, t, J=4 Hz), 3.77 (3H, s), 3.86 (3H, s), 6.60–6.71 (2H, m), 6.81–7.04 ( 5H, m)

Elemental analysis (for $C_{28}H_{41}Cl_2N_3O_2 \cdot 2H_2O$): Calculated: C, 60.21; H, 8.12; N, 7.52 Found: C, 60.16; H, 8.43; N, 7.08

The following compounds were synthesized in the same manner as in EXAMPLE 7-1 describved hereinabove.

EXAMPLE 7-2

3,4-Dihydro-6-methoxy-1'-[2-(4-phenylpiperazine-1-yl)ethyl]spiro[naphthalene-2(1H), 2'-piperidine] dihydrochloride

EXAMPLE 7-3

1'-[2-(4-(2-Chlorophenyl)piperazine-1-yl)ethyl]-3,4-dihydro-6-methoxyspiro[naphthalene-2(1H),2'-piperidine] dihydrochloride

EXAMPLE 7-4

1'-[2-(4-(4-Chlorophenyl)piperazine-1-yl)ethyl]-3,4-dihydro-6-methoxyspiro[naphthalene-2(1H),2'-piperidine] dihydrochloride

EXAMPLE 7-5

1'-[2-(4-(4-Fluorophenyl)piperazine-1-yl)ethyl]-3,4-dihydro-6-methoxyspiro[naphthalene-2(1H),2'-piperidine]dihydrochloride

EXAMPLE 7-6

1'-[2-(4-(3-Trifluoromethylphenyl)piperazine-1-yl)ethyl]-3,4-dihydro-6-methoxyspiro[naphthalene-2(1H),2'-piperidine] dihydrochloride

EXAMPLE 7-7

3,4-Dihydro-6-methoxy-1'-[2-(4-phenylmethylpiperazine-1-yl)ethyl]spiro[naphthalene-2(1H),2'-piperidine]trihydrochloride

EXAMPLE 7-8

1'-[2-(4-(4-Fluorophenyl)piperazine-1-yl)ethyl]-3,4-dihydro-6,7-dimethoxyspiro[naphthalene-2(1H),2'-piperidine] dihydrochloride

EXAMPLE 7-9

3,4-Dihydro-6-methoxy-1'-[2-(4-phenylpiperidine-1-yl)ethyl]spiro[naphthalene-2(1H),2'-piperidine] dihydrochloride

EXAMPLE 7-10

3,4-Dihydro-6-methoxy-1'-(2-morpholinoethyl)spiro[naphthalene-2(1H),2'-piperidine] dihydrochloride

EXAMPLE 7-11

3,4-Dihydro-1'-[2-(2,3,4,5-tetrahydro-(1H)-3-benzoazepin-3-yl)ethylspiro[naphthalene-2(1H),2'-piperidine] dihydrochloride

EXAMPLE 7-12

1'-[2-(4-(4-Fluorophenyl)piperazine-1-yl)ethyl]-3,4-dihydrospiro[naphthalene-2(1H),2'-piperidine] 2 hydrochloride

EXAMPLE 7-13

1'-[2-(4-(3-Trifluoromethylphenyl)piperazine-1-yl)ethyl]-3,4-dihydrospiro[naphthalene-2(1H),2'-piperidine] 2 hydrochloride

EXAMPLE 7-14

1'-[2-(4-(4-Fluorophenyl)piperazine-1-yl)ethyl]-1,3,4,5,6,7,3',4'-octahydrospiro[2H-azepine-2,2'-naphthalene] 2 hydrochloride

EXAMPLE 7-15

1'-[3-(4-(4-Fluorophenyl)piperazine-1-yl)propyl]-3,4-dihydro-6-methoxyspiro[naphthalene-2(1H),2'-piperidine]hydrochloride

EXAMPLE 7-16

1'-[2-(4-(4-Fluorophenyl)piperazine-1-yl)ethyl]-4,5-dihydrospiro[benzo[b]thiophene-6(7H),2'-piperidine] hydrochloride

EXAMPLE 7-17

1'-[2-(4-(3-Trifluoromethylphenyl)piperazine-1-yl)ethyl]-4,5-dihydrospiro[benzo[b]thiophene-6(7H),2'-piperidine] 2 hydrochloride Tables 21 to 24 show the structural formulas, physical properties and NMR spectra of these compounds.

TABLE 21

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 7-2 | [structure] .2HCl | (1) Noncrystalline powder (2) C$_{27}$H$_{39}$Cl$_2$N$_3$O·H$_2$O | ① 63.52 ② 63.47 | 8.09 8.08 | 8.23 8.40 | 1.37–1.98(8H, m), 2.43–2.88(14H, m), 3.19(4H, t, J=5Hz), 3.77(3H, s), 6.62–6.73(2H, m), 6.80–7.03(4H, m), 7.19(2H, t, J=8Hz) |
| 7-3 | [structure] .2HCl | (1) Noncrystalline powder (2) C$_{27}$H$_{38}$Cl$_3$N$_3$O·H$_2$O | ① 59.50 ② 59.79 | 7.40 7.56 | 7.71 7.66 | 1.35–1.98(6H, m), 2.43–2.87(16H, m), 3.07(4H, t, J=5Hz), 3.77(3H, s), 6.61–6.73(2H, m), 6.91–7.09(3H, m), 7.16–7.26(1H, m), 7.35(1H, dd, J=8Hz, 4Hz) |

TABLE 21-continued

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 7-4 | [structure: 6-methoxy-tetrahydronaphthalene-spiro-piperidine linked via piperazine to 4-Cl-phenyl] .2HCl | (1) Noncrystalline powder (2) C$_{27}$H$_{38}$Cl$_3$N$_3$O· 5/4H$_2$O | ① 59.02 ② 58.92 | 7.43 7.80 | 7.64 7.74 | 1.35–1.98(6H, m), 2.44–2.88(16H, m), 2.98–3.24(4H, m), 3.77(3H, s), 6.62–6.73(2H, m), 6.80–7.02(3H, m), 7.19(2H, d, J=8Hz) |
| 7-5 | [structure: 6-methoxy-tetrahydronaphthalene-spiro-piperidine linked via piperazine to 4-F-phenyl] .2HCl | (1) Noncrystalline powder (2) C$_{27}$H$_{38}$Cl$_2$FN$_3$O· 3/2H$_2$O | ① 60.33 ② 60.35 | 7.69 8.04 | 7.82 7.62 | 1.34–1.98(6H, m), 2.44–2.88(16H, m), 3.04–3.23(4H, m), 3.77(3H, s), 6.62–6.72(2H, m), 6.82–7.02(5H, m) |
| 7-6 | [structure: 6-methoxy-tetrahydronaphthalene-spiro-piperidine linked via piperazine to 3-CF$_3$-phenyl] .2HCl | (1) Noncrystalline powder (2) C$_{28}$H$_{38}$Cl$_2$F$_3$N$_3$O·H$_2$O | ① 58.13 ② 58.03 | 6.97 7.19 | 7.26 7.23 | 1.34–1.98(6H, m), 2.44–2.86(16H, m), 3.22(4H, t, J=5Hz), 3.77(3H,s), 6.62–6.74(2H, m), 6.96–7.14(4H, m), 7.34(1H, t, J=8Hz) |

TABLE 22

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 7-7 | [structure: 6-methoxy-tetrahydronaphthalene-spiro-piperidine linked via piperazine to benzyl] .3HCl | (1) Noncrystalline powder (2) C$_{28}$H$_{42}$Cl$_3$N$_3$O· H$_2$O | ① 59.94 ② 59.95 | 7.90 8.26 | 7.49 7.21 | 1.37–1.97(8H, m), 2.38–2.84(18H, m), 3.50(2H, s), 3.76(3H, s), 6.61–6.72(2H, m), 6.97(1H, d, J=8Hz), 7.24–7.35(5H, m) |
| 7-8 | [structure: 6,7-dimethoxy-tetrahydronaphthalene-spiro-piperidine linked via piperazine to 4-F-phenyl] .2HCl | (1) Noncrystalline powder (2) C$_{28}$H$_{40}$Cl$_2$N$_3$O$_2$F·5/2H$_2$O | ① 57.43 ② 57.20 | 7.75 7.59 | 7.18 6.86 | 1.35–1.99(8H, m), 2.42–2.92(14H, m), 3.04–3.24(4H, m), 3.84(3H, s), 3.85(3H, s), 6.59(2H, s), 6.80–7.04(4H, m) |

TABLE 22-continued

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 7-9 | [structure: 6-methoxy-tetrahydronaphthalene spiro-piperidine with N-CH$_2$CH$_2$-piperidinyl-4-phenyl, .2HCl] | (1) Noncrystalline powder (2) C$_{28}$H$_{40}$Cl$_2$N$_2$O· 5/4H$_2$O | ① 65.42 ② 65.61 | 8.33 8.41 | 5.45 5.40 | 1.35–2.19(12H, m), 2.40–2.88(13H, m), 3.04(2H d, J=12Hz), 3.77(3H, s), 6.62–6.74(2H, m), 6.99(1H, d, J=8Hz), 7.14–7.38(5H, m) |

TABLE 23

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 7-10 | [structure: 6-methoxy-tetrahydronaphthalene spiro-piperidine with N-CH$_2$CH$_2$-morpholine, .2HCl] | (1) Noncrystalline powder (2) C$_{21}$H$_{34}$Cl$_2$N$_2$O$_2$· 3/2H$_2$O | ① 56.75 ② 56.96 | 8.39 8.37 | 6.30 6.26 | 1.33–1.96(8H, m), 2.31–2.88(14H, m), 3.64–3.84(4H, m), 3.77(3H, s), 6.61–6.76(2H, m), 6.97(1H, d, J=8Hz) |
| 7-11 | [structure: 6-methoxy-tetrahydronaphthalene spiro-piperidine with N-CH$_2$CH$_2$-benzazepine, .2HCl] | (1) Noncrystalline powder (2) C$_{27}$H$_{34}$Cl$_2$N$_2$O$_2$· 3/2H$_2$O | ① 64.28 ② 64.00 | 8.19 8.06 | 5.55 5.46 | 1.37–1.96(8H, m), 2.49–2.95 (18H, m), 3.77(3H, s), 6.62–6.72(2H, m), 6.98(1H, d, J=8Hz), 7.04–7.15(4H, m) |
| 7-12 | [structure: tetrahydronaphthalene spiro-piperidine with N-CH$_2$CH$_2$-piperazinyl-4-fluorophenyl, .2HCl] | (1) Noncrystalline powder (2) C$_{26}$H$_{36}$Cl$_3$N$_3$Cl$_2$F· 3/2H$_2$O | ① 61.53 ② 61.35 | 7.75 8.00 | 8.28 8.20 | 1.33–2.00(8H, m), 2.44–2.95(14H, m), 3.06–3.15(4H, m), 6.82–7.02(4H, m), 7.10(4H, s) |
| 7-13 | [structure: tetrahydronaphthalene spiro-piperidine with N-CH$_2$CH$_2$-piperazinyl-3-trifluoromethylphenyl, .2HCl] | (1) Noncrystalline powder (2) C$_{27}$H$_{36}$Cl$_2$N$_3$F$_3$· H$_2$O | ① 59.12 ② 59.28 | 6.98 7.24 | 7.66 7.66 | 1.43–2.00(8H, m), 2.44–2.94(14H, m), 3.17–3.29(4H, m), 7.00–7.14(3H, m), 7.09(4H, s), 7.33(1H, t, J=8Hz) |

TABLE 23-continued

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 7-14 | (structure: tetrahydronaphthalene-spiro-azepane with N-CH$_2$CH$_2$-piperazine-(4-F-phenyl), ·2HCl) | (1) Noncrystalline powder (2) C$_{27}$H$_{35}$Cl$_2$N$_3$F· 2H$_2$O | ① 61.12 ② 61.15 | 7.98 8.18 | 7.92 7.83 | 1.33–1.93(10H, m), 2.14–2.96(14H, m), 3.10(4H, t, J=5Hz), 6.81–7.01(4H, m), 7.08(4H, s) |

TABLE 24

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 7-15 | (6-MeO-tetrahydronaphthalene-spiro-piperidine with N-(CH$_2$)$_3$-piperazine-(4-F-phenyl), ·2HCl) | (1) 209–211 (decomposed) (2) C$_{28}$H$_{40}$Cl$_2$N$_3$OF· 5/2H$_2$O | ① 59.04 ② 59.01 | 7.96 7.83 | 7.38 7.40 | 1.41–1.99 (10H, m), 2.31–2.88 (14H, m), 3.07–3.16(4H, m), 3.77(3H, s), 6.62–6.72 (2H, m), 6.84–7.02(3H, m), 7.15–7.32 (2H, m) |
| 7-16 | (thiophene-fused cyclohexane-spiro-piperidine with N-CH$_2$CH$_2$-piperazine-(4-F-phenyl), ·3HCl) | (1) 163–167 (2) C$_{24}$H$_{35}$Cl$_3$N$_3$SF· 7/4H$_2$O | ① 51.99 ② 51.89 | 6.99 7.33 | 7.58 7.50 | 1.38–1.77(7H, m), 1.88–2.11 (1H, m), 2.42– 2.95(14H, m), 3.04–3.23(4H, m), 6.73(1H, d, J=5Hz), 6.80–7.01(4H, m), 7.05(1H, d, J=5Hz) |
| 7-17 | (thiophene-fused cyclohexane-spiro-piperidine with N-CH$_2$CH$_2$-piperazine-(3-CF$_3$-phenyl), ·2HCl) | (1) 197–202 (decomposed) (2) C$_{25}$H$_{31}$Cl$_2$N$_3$SF$_3$· 5/4H$_2$O | ① 53.71 ② 53.69 | 6.58 6.48 | 7.52 7.59 | 1.35–1.78(7H, m), 1.90–2.08 (1H, m), 2.37–2.90 (14H, m), 3.14–3.28(4H, m), 6.72(1H, d, J=5Hz), 6.99–7.12(3H, m), 7.04(1H, d, J=5Hz), 7.32(1H, t, J=8Hz) |

EXAMPLE 8-1

3,4-Dihydro-6-hydroxy-1'-propylspiro[naphthalene-2(1H),2'-piperidine] hydrochloride

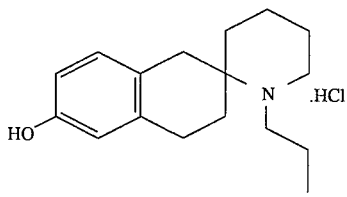

To 1.33 g of 3,4-dihydro-6-methoxy-1'-propylspiro[naphthalene -2(1H),2'-piperidine] as obtained Example 4-1, 20 ml of 4 8% hydrobromic acid was added, followed by thermal refluxing for 2 hours. After the reaction mixture was neutralized by the addition of 10% sodium hydroxide, a dilute aqueous solution of potassium carbonate was added; the reaction mixture was extracted with methylene chloride. The extract was dried over anhydrous sodium sulfate and filtered, after which the solvent was distilled off. The residue was treated with 1.5 ml of 4 N-methanolic hydrochloric acid to yield a solid, which was then recrystallized from methanol-ethyl acetate to yield 1.11 g of a white crystal.

Melting point: 246°–249° C.

$^1$H-NMR (ppm, CDCl$_3$): 0.86 (3H, t, J=7 Hz), 1.36–1.98 (10H, m), 2.26–2.54 (2H, m), 2.58–2.91 (6H, m), 4.27 (1H, br s), 6.52–6.66 (2H, m), 6.91 (1H, d, J=8 Hz)

Elemental analysis (for C$_{17}$H$_{26}$ClNO.¼H$_2$O): Calculated: C, 67.98; H, 8.89; N, 4.66 Found C, 68.00; H, 8.86; N, 4.64

The following compounds were synthesized in the same manner as in Example 8-1 described hereinabove.

EXAMPLE 8-2

3,4-Dihydro-6-hydroxyspiro[naphthalene-2(1H),2'-piperidine] hydrochloride

EXAMPLE 8-3

3,4-Dihydro-6,7-dihydroxy-1'-propylspiro[naphthalene-(1H),2'-piperidine] hydrochloride

EXAMPLE 8-4

3,4-Dihydro-6,7-dihydroxy-1'-phenylmethylspiro[naphthalene-(1H),2'-piperidine]

Table 25 shows the structural formulas, physical properties and NMR spectra of these compounds.

TABLE 25

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 8-2 | | (1) 253–255 (decomposed) (2) C$_{14}$H$_{20}$ClNO·¼H$_2$O | ① 65.10  ② 65.15 | 8.00  8.08 | 5.42  5.67 | 1.40–2.06(8H, m), 2.58–2.92(6H, m), 4.42(2H, br s), 6.48–6.60(2H, m), 6.85(1H, d, J=8Hz) |
| 8-3 | | (1) 221–225 (decomposed) (2) C$_{17}$H$_{26}$ClNO$_2$·½H$_2$O | ① 64.54  ② 64.75 | 8.44  8.46 | 4.43  4.49 | 0.86(3H, t, J=7Hz), 1.31–1.72 (8H, m), 1.72–1.93(2H, m), 2.34–2.93(8H, m), 3.70(2H, br s), 6.54(1H, s), 6.55(1H, s) |
| 8-4 | | (1) 122–124 (2) C$_{21}$H$_{25}$NO$_2$ | ① 77.99  ② 77.72 | 7.79  7.79 | 4.33  4.15 | 1.44(6H, br), 1.61–1.72(1H, m), 1.82–1.99(1H, m), 2.38–2.80(6H, m), 3.45–3.66(2H, m), 6.44(1H, s), 6.45 (1H, s), 7.12–7.29(5H, m); (DMSO-d$_6$) |

EXAMPLE 9-1

3,4-Dihydro-6-phenylmethoxy-1'-propylspiro[naphthalene-2(1H),2'-piperidine] hydrochloride

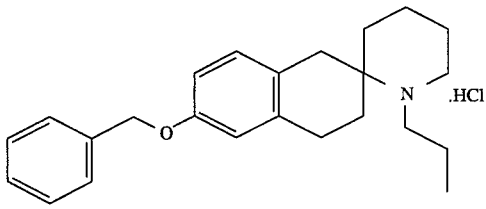

0.21 g of 3,4-dihydro-6-hydroxy-1'-propylspiro[naphthalene-2(1H),2'-piperidine] as obtained in Example 8-1 was dissolved in 3 ml of N,N-dimethylformamide. To this solution, 0.062 g of 60% sodium hydride and 0.14 g of benzyl bromide were added, followed by stirring at room temperature for 1 hour. Water was added; the reaction mixture was extracted with ethyl acetate and washed with water and saturated saline. The extract was dried over anhydrous sodium sulfate and filtered, after which the solvent was distilled off. The residue was purified by alumina column chromatography with ethyl acetate:hexane (1:4) as a developing solvent; the solution containing the desired product was distilled under reduced pressure. The residue was treated with 0.16 ml of 4 N-methanolic hydrochloric acid to yield 0.16 g of a noncrystalline powder.

$^1$H-NMR (ppm, CDCl$_3$): 0.85 (3H, t, J=7 Hz), 1.32–1.98 (10H, m), 2.22–2.50 (2H, m), 2.56–2.90 (6H, m), 5.02 (2H, s), 6.68–6.89 (2H, m), 6.98 (1H, d, J=8 Hz), 7.22–7.48 (5H, m)

Elemental analysis (for C$_{24}$H$_{32}$ClNO.H$_2$O): Calculated: C, 71.35; H, 8.48; N, 3.47 Found: C, 71.47; H, 8.51; N, 3.51

The following compounds were synthesized in the same manner as in Example 9-1 described hereinabove.

EXAMPLE 9-2

6,7-Ethylenedioxy-3,4-dihydro-1'-propylspiro[naphthalene-2(1H),2'-piperidine] hydrochloride

EXAMPLE 9-3

3,4-Dihydro-6,7-methylenedioxy-1'-propylspiro[naphthalene-2(1H),2'-piperidine] hydrochloride

EXAMPLE 9-4

3,4-Dihydro-6,7-bis(phenylmethoxy)-1'-propylspiro[naphthalene-2(1H),2'-piperidine] hydrochloride

EXAMPLE 9-5

6-Cyclopentyloxy-3,4-dihydro-1'-propylspiro[naphthalene-2(1H),2'-piperidine] hydrochloride

EXAMPLE 9-6

6-(2-Chlorophenylmethoxy)-3,4-dihydro-1'-propylspiro[naphthalene-2(1H),2'-piperidine] hydrochloride

EXAMPLE 9-7

6-(3-Chlorophenylmethoxy)-3,4-dihydro-1'-propylspiro[naphthalene-2(1H),2'-piperidine] hydrochloride

EXAMPLE 9-8

6-(4-Chlorophenylmethoxy)-3,4-dihydro-1'-propylspiro[naphthalene-2(1H),2'-piperidine] hydrochloride

EXAMPLE 9-9

6-(3-Cyanophenylmethoxy)-3,4'-dihydro-1'-propylspiro[naphthalene-2(1H),2'-piperidine ] hydrochloride

EXAMPLE 9-10

3,4-Dihydro-6-diphenylmethoxy-1'-propylspiro[naphthalene-2(1H),2'-piperidine]hydrochloride

EXAMPLE 9-11

3,4-Dihydro-6-(4-phenylphenylmethoxy)-1'-propylspiro[naphthalene-2(1H),2'-piperidine] hydrochloride

EXAMPLE 9-12

3,4-Dihydro-6-(2-morpholinoethoxy)-1'-propylspiro[naphthalene-2(1H),2'-piperidine] dihydrochloride

EXAMPLE 9-13

3,4-Dihydro-6-(3-morpholinopropyloxy)-1'-propylspiro[naphthalene-2(1H),2'-piperidine] dihydrochloride

EXAMPLE 9-14

3,4-Dihydro-6-[3-(1-imidazolyl)propyloxy]-1'-propylspiro[naphthalene-2(1H),2'-piperidine] dihydrochloride

EXAMPLE 9-15

3,4-Dihydro-6-[(2-methylthiazol-4-yl)methoxy]-1'-propylspiro[naphthalene-2(1H),2'-piperidine] dihydrochloride

EXAMPLE 9-16

3,4-Dihydro-6-(2-phenylethoxy)-1'-propylspiro[naphthalene-2(1H),2'-piperidine] dihydrochloride

EXAMPLE 9-17

6-(3-Chloropropyloxy)-3,4-dihydro-1'-propylspiro[naphthalene-2(1H),2'-piperidine] hydrochloride

EXAMPLE 9-18

3,4-Dihydro-6-(2-methylphenylmethoxy)-1'-propylspiro[naphthalene-2(1H),2'-piperidine] hydrochloride

EXAMPLE 9-19

6-(2-Fluorophenylmethoxy)-3,4-dihydro-1'-propylspiro[naphthalene-2(1H),2'-piperidine] hydrochloride

EXAMPLE 9-20

6-(2-Cyanophenylmethoxy)-3,4-dihydro-1'-propylspiro[naphthalene-2(1H),2'-piperidine] hydrochloride

EXAMPLE 9-21

6-(4-Fluorophenylmethoxy)-3,4-dihydro-1'-propylspiro[naphthalene-2(1H),2'-piperidine] hydrochloride

EXAMPLE 9-22

6-(2,4-Dichlorophenylmethoxy)-3,4-dihydro-1'-propylspiro[naphthalene-2(1H),2'-piperidine] hydrochloride

EXAMPLE 9-23

3,4-Dihydro-6-(2-methoxyphenylmethoxy)-1'-propylspiro[naphthalene-2(1H),2'-piperidine] hydrochloride

EXAMPLE 9-24

6-(2-Trifluoromethylphenylmethoxy)-3,4-dihydro-1'-propylspiro[naphthalene-2(1H),2'-piperidine] hydrochloride

EXAMPLE 9-25

6-(2-Chlorophenylmethoxy)-3,4-dihydrospiro[naphthalene-2(1H),2'-piperidine] hydrochloride

EXAMPLE 9-26

6-(2-Chlorophenylmethoxy)-1'-ethyl-3,4-dihydrospiro[naphthalene-2(1H),2'-piperidine] hydrochloride

EXAMPLE 9-27

6-(2-Chlorophenylmethoxy)-3,4-dihydro-1'-(3-phenylpropyl)spiro[naphthalene-2(1H),2'-piperidine] hydrochloride

EXAMPLE 9-28

6-(4-Fluorophenylmethoxy)-3,4-dihydrospiro[naphthalene-2(1H),2'-piperidine] hydrochloride

EXAMPLE 9-29

6-(4-Fluorophenylmethoxy)-3,4-dihydro-1'-pentylspiro[naphthalene-2(1H),2'-piperidine] hydrochloride

EXAMPLE 9-30

6-(4-Fluorophenylmethoxy)-1'-heptyl-3,4-dihydrospiro[naphthalene-2(1H),2'-piperidine] hydrochloride

EXAMPLE 9-31

6-(4-Fluorophenylmethoxy)-3,4-dihydro-1'-(2,2-dimethyl-1-propyl)]spiro[naphthalene-2(1H),2'-piperidine] hydrochloride

EXAMPLE 9-32

{6-(4-Fluorophenylmethoxy)-3,4-dihydrospiro[naphthalene-2(1H),2'-piperidine]}-1'-yl acetamido hydrochloride

EXAMPLE 9-33

{6-(4-Fluorophenylmethoxy)-3,4-dihydrospiro[naphthalene-2(1H),2'-piperidine]}-1'-yl acetonitrile hydrochloride

EXAMPLE 9-34

1'-(2,2,2-Trifluoroethyl)-6-(4-fluorophenylmethoxy)-3,4-dihydrospiro[naphthalene-2(1H),2'-piperidine] hydrochloride

EXAMPLE 9-35

6-(4-Fluorophenylmethoxy)-3,4-dihydro-1'-(2-propargyl)spiro[naphthalene-2(1H),2'-piperidine] hydrochloride

EXAMPLE 9-36

6-(4-Fluorophenylmethoxy)-3,4-dihydro-1'-propylspiro[naphthalene-2(1H),2'-piperidine]-1-one hydrochloride

EXAMPLE 9-37

6-(2-Chlorophenylmethoxy)-3,4-dihydro-1'-propylspiro[naphthalene-2(1H),2'-piperidine]-1-one hydrochloride

EXAMPLE 9-38

{6-(4-Fluorophenylmethoxy)-3,4-dihydrospiro[naphthalene-2(1H),2'-piperidine]}-1'-yl propionenitrile hydrochloride

EXAMPLE 9-39

6-(4-Fluorophenylmethoxy)-3,4-dihydro-1'-(2-hydroxyethyl)spiro[naphthalene-2(1H),2'-piperidine] hydrochloride

EXAMPLE 9-40

6-(4-Fluorophenylmethoxy)-1'-[2-(4-(4-fluorophenyl piperazine-1-yl)ethyl]-3,4-dihydrospiro[naphthalene-2(1H),2'-piperidine]

EXAMPLE 9-41

6-(4-Fluorophenylmethoxy)-3,4-dihydro-1'-[2-(1imidazolyl)ethyl]spiro[naphthalene-2(1H),2'-piperidine] hydrochloride

EXAMPLE 9-42

1'-Butyl-6-(4-fluorophenylmethoxy)-3,4-dihydrospiro[naphthalene-2(1H),2'-piperidine] hydrochloride

EXAMPLE 9-43

6-(1-Phenylethoxy)-3,4-dihydro-1'-propylspiro[naphthalene-2(1H),2'-piperidine] hydrochloride

EXAMPLE 9-44

3,4-Dihydro-1'-propyl-6-(2-pyridylmethoxy)spiro[naphthalene-2(1H),2'-piperidine]2-hydrochloride

EXAMPLE 9-45

3,4-Dihydro-1'-propyl-6-(3-thienylmethoxy)spiro[naphthalene-2(1H),2'-piperidine] hydrochloride

EXAMPLE 9-46

3,4-Dihydro-6-(2-naphthylmethoxy)-1'-propylspiro[naphthalene-2(1H),2'-piperidine] hydrochloride

EXAMPLE 9-47

3,4-Dihydro-6-(2-naphthylmethoxy)spiro[naphthalene-2(1H),2'-piperidine] hydrochloride

EXAMPLE 9-48

1'-[3-(4-Fluorophenoxy)-2-hydroxypropyl]-3,4-dihydro-6-(2-naphthylmethoxy)spiro[naphthalene-2(1H),2'-piperidine] hydrochloride

EXAMPLE 9-49

3,4-Dihydro-6-[(2,5-dimethylisooxazoline-4-yl)methoxy]-1'-propylspiro[naphthalene-2(1H),2'-piperidine] hydrochloride

EXAMPLE 9-50

6-Ethoxy-3,4-dihydrospiro[naphthalene-2(1H),2'-piperidine] hydrochloride

EXAMPLE 9-51

6,7-Diethoxy-3,4-dihydro-1'-phenylmethylspiro[naphthalene-2(1H),2'-piperidine]

EXAMPLE 9-52

6,7-Diethoxy-3,4-dihydrospiro[naphthalene-2(1H),2'-piperidine] hydrochloride

Tables 26 to 37 show the structural formulas, physical properties and NMR spectra of these compounds.

TABLE 26

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 9-2 | | (1) 204–207 (2) C$_{19}$H$_{28}$ClNO$_2$·1/2H$_2$O | ① 65.79 ② 65.73 | 8.43 8.34 | 4.04 4.18 | 0.85(3H, t, J=7Hz), 1.13–1.95(10H, m), 2.19–2.44(2H, m), 2.51–2.84 .(6H, m), 4.21(4H, s), 6.58(2H, s) |
| 9-3 | | (1) 187–190 (2) C$_{18}$H$_{26}$ClNO$_2$·3/4H$_2$O | ① 64.08 ② 64.02 | 8.22 8.07 | 4.15 4.22 | 0.86(3H, t, J=7Hz), 1.35–1.78(9H, m), 1.78–1.98(1H, m), 2.19–2.50 (2H, m), 2.53–2.87(6H, m), 5.87(2H, s), 6.55(2H, s) |
| 9-4 | | (1) Noncrystalline powder (2) C$_{31}$H$_{38}$ClNO$_2$·5/4H$_2$O | ① 72.35 ② 72.26 | 7.93 7.73 | 2.72 2.69 | 0.85(3H, t, J=7Hz), 1.32–1.96(10H, m), 2.20–2.88(8H, m), 5.10(4H, s), 6.68(2H, s), 7.27–7.49 (10H, m) |
| 9-5 | | (1) 219–221 (2) C$_{22}$H$_{34}$ClNO·1/4H$_2$O | ① 71.71 ② 71.93 | 9.44 9.36 | 3.80 3.88 | 0.85(3H, t, J=7Hz), 1.20–1.97(18H, m), 2.21–2.48(2H, m), 2.55–2.87 (6H, m), 4.65–4.75(1H, m), 6.57–6.67(2H, m), 6.95(1H, d, J=8Hz) |

TABLE 27

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 9-6 | 2-Cl-benzyloxy tetrahydronaphthalene spiropiperidine N-propyl ·HCl | (1) 167–169 (2) C$_{24}$H$_{31}$Cl$_2$NO | ① 68.57 ② 68.23 | 7.43 7.44 | 3.33 3.34 | 0.85(3H, t, J=7Hz), 1.33–2.00(10H, m), 2.25–2.45(2H, m), 2.56–2.89 (6H, m), 5.12(2H, s), 6.71–6.80(2H, m), 6.99 (1H, d, J=8Hz), 7.22–7.42(3H, m), 7.52–7.60(1H, m) |
| 9-7 | 3-Cl-benzyloxy analog ·HCl | (1) Noncrystalline powder (2) C$_{24}$H$_{31}$Cl$_2$NO·H$_2$O | ① 65.75 ② 65.91 | 7.59 7.59 | 3.19 3.21 | 0.85(3H, t, J=7Hz), 1.34–1.97(10H, m), 2.20–2.47(2H, m), 2.56–2.88 (6H, m), 4.99(2H, s), 6.67–6.77(2H, m), 6.98 (1H, d, J=8Hz), 7.29(1H, s), 7.30(2H, s), 7.43(1H, s) |
| 9-8 | 4-Cl-benzyloxy analog ·HCl | (1) Noncrystalline powder (2) C$_{24}$H$_{31}$Cl$_2$NO·1/4H$_2$O | ① 67.84 ② 68.09 | 7.47 7.65 | 3.30 3.33 | 0.85(3H, t, J=7Hz), 1.33–1.98(10H, m), 2.22–2.49(2H, m), 2.56–2.89 (6H, m), 4.99(2H, s), 6.66–6.76(2H, m), 6.98 (1H, d, J=8Hz), 7.29(1H, s), 7.30(2H, s), |
| 9-9 | 3-CN-benzyloxy analog ·HCl | (1) 179–181 (2) C$_{25}$H$_{31}$ClN$_2$O·1/2H$_2$O | ① 71.50 ② 71.45 | 7.68 7.85 | 6.67 6.62 | 0.85(3H, t, J=7Hz), 1.35–1.99(10H, m), 2.25–2.45(2H, m), 2.57–2.89 (6H, m), 5.05(2H, s), 6.64–6.76(2H, m), 6.99(1H, d, J=8Hz), 7.43–7.76(4H, m) |
| 9-10 | diphenylmethyloxy analog ·HCl | (1) Noncrystalline powder (2) C$_{30}$H$_{36}$ClNO·H$_2$O | ① 75.05 ② 75.32 | 7.98 8.01 | 2.92 2.91 | 0.83(3H, t, J=7Hz), 1.24–1.92(10H, m), 2.18–2.45(2H, m), 2.51–2.82 (6H, m), 6.14(1H, s), 6.64–6.74(2H, m), 6.88 (1H, d, J=8Hz), 7.19–7.46(10H, m) |

TABLE 28

| Example | Structural Formula | (1) Melting Point (°C.) or Physical Property (2) Molecular Formula | (3) Elemental Analysis ① Calculated ② Found | | | ¹H—NMR (ppm, CDCl₃) |
|---|---|---|---|---|---|---|
| | | | C | H | N | |
| 9-11 | [biphenyl-CH₂-O-naphthalene-spiro-piperidine-N-propyl] .HCl | (1) 178–182 (2) $C_{30}H_{36}ClNO \cdot 3/4H_2O$ | ① 75.77 ② 75.62 | 7.95 7.83 | 2.95 3.12 | 0.86(3H, t, J=7Hz), 1.45–1.99 (10H, m), 2.22–2.50(2H, m), 2.56–2.89 (6H, m), 5.06 (2H, s), 6.71–6.82(2H, m), 6.99(1H, d, J=8Hz), 7.29–7.65(9H, m) |
| 9-12 | [morpholine-N-CH₂CH₂-O-naphthalene-spiro-piperidine-N-propyl] .2HCl | (1) 236–237 (decomposed) (2) $C_{23}H_{38}Cl_2N_2-O_2 \cdot 1/2H_2O$ | ① 60.78 ② 60.73 | 8.65 8.47 | 6.16 6.30 | 0.85(3H, t, J=7Hz), 1.34–1.98 (10H, m), 2.24–2.44(2H, m), 2.53–2.88 (12H, m), 3.73(4H, t, J=5Hz), 4.07 (2H, t, J=6Hz), 6.61–6.72(2H, m), 6.97(1H, d, J=8Hz) |
| 9-13 | [morpholine-N-CH₂CH₂CH₂-O-naphthalene-spiro-piperidine-N-propyl] .2HCl | (1) Noncrystalline powder (2) $C_{24}H_{40}Cl_2N_2-O_2 \cdot 5/4H_2O$ | ① 59.80 ② 59.78 | 8.89 8.79 | 5.81 5.71 | 0.85(3H, t, J=7Hz), 1.34–2.03 (12H, m), 2.21–2.88 (14H, m), 3.72(4H, t, J=5Hz), 3.98 (2H, t, J=6Hz), 6.60–6.71(2H, m), 6.79(1H, d, J=8Hz) |
| 9-14 | [imidazole-N-CH₂CH₂CH₂-O-naphthalene-spiro-piperidine-N-propyl] .2HCl | (1) Noncrystalline powder (2) $C_{23}H_{35}Cl_2N_3-O \cdot H_2O$ | ① 60.25 ② 60.51 | 8.13 7.96 | 9.17 9.11 | 0.85(3H, t, J=7Hz), 1.34–2.03 (10H, m), 2.12–2.48 (4H, m), 2.56–2.87(6H, m), 3.87(2H, t, J=6Hz), 4.17(2H, t, J=7Hz), 6.57–6.69(2H, m), 6.91(1H, s), 6.97(1H, d, J=8Hz), 7.05 (1H, s), 7.47 (1H, s) |

TABLE 28-continued

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 9-15 | (structure with methylthiazole-CH$_2$-O-tetrahydronaphthalene-spiropiperidine-propyl) .2HCl | (1) Noncrystalline powder (2) C$_{22}$H$_{32}$Cl$_2$N$_2$—OS·1/2H$_2$O | ① 58.40 ② 58.45 | 7.35 7.63 | 6.19 5.93 | 0.85(3H, t, J=7Hz), 1.32–1.97 (10H, m), 2.21–2.46 (2H, m), 2.54–2.88 (6H, m), 2.73(3H, s), 5.11(2H, s), 6.68–6.79 (2H, m), 6.98(1H, d, J=8Hz), 7.13(1H, s) |

TABLE 29

| Example | Structural Formula | (1) Melting Point (°C.) or Physical Property (2) Molecular Formula | (3) Elemental Analysis ① Calculated ② Found | | | $^1$H—NMR(ppm, CDCl$_3$) |
|---|---|---|---|---|---|---|
| | | | C | H | N | |
| 9-16 | (phenylethyl-O-tetrahydronaphthalene-spiropiperidine-propyl) .HCl | (1) 129–133 (2) C$_{25}$H$_{34}$ClNO·H$_2$O | ① 71.83 ② 71.64 | 8.68 8.11 | 3.35 3.34 | 0.85(3H, t, J=7Hz), 1.34–1.96(10H, m), 2.23–2.44(2H, m), 2.54–2.86(6H, m), 3.07(2H, t, J=7Hz), 4.13(2H, t, J=7Hz), 6.58–6.71(2H, m), 6.96(1H, d, J=8Hz), 7.16–7.38(5H, m) |
| 9-17 | (Cl-propyl-O-tetrahydronaphthalene-spiropiperidine-propyl) .HCl | (1) 156–158 (2) C$_{20}$H$_{31}$Cl$_2$NO | ① 64.51 ② 64.56 | 8.39 8.39 | 3.76 3.86 | 0.86(3H, t, J=7Hz), 1.32–1.97(10H, m), 2.14–2.48(4H, m), 2.57–2.88 (6H, m), 3.74(2H, t, J=7Hz), 4.07(2H, t, J=7Hz), 6.62–6.73(2H, m), 6.98(1H, d, J=8Hz) |
| 9-18 | (o-methylbenzyl-O-tetrahydronaphthalene-spiropiperidine-propyl) .HCl | (1) 168–173 (2) C$_{25}$H$_{34}$ClNO | ① 75.07 ② 75.14 | 8.57 8.62 | 3.50 3.55 | 0.86(3H, t, J=7Hz), 1.34–1.98(10H, m), 2.20–2.48(2H, m), 2.37(3H, s), 2.54–2.89(6H, m), 4.98 (2H, s) 6.71–6.80(2H, m), 6.99(1H, d, J=8Hz), 7.15–7.30(3H, m), 7.37–7.44(1H, m) |
| 9-19 | (o-fluorobenzyl-O-tetrahydronaphthalene-spiropiperidine-propyl) .HCl | (1) 152–154 (2) C$_{24}$H$_{31}$ClNOF | ① 71.36 ② 71.30 | 7.73 7.79 | 3.47 3.46 | 0.86(3H, t, J=7Hz), 1.18–1.98(10H, m), 2.20–2.49(2H, m), 2.54–2.89 (6H, m), 5.09(2H, s), 6.70–6.81(2H, m), 6.94–7.30(4H, m), 7.51(1H, d, t, J=8Hz, 2Hz) |

TABLE 29-continued

| Example | Structural Formula | (1) Melting Point (°C.) or Physical Property (2) Molecular Formula | (3) Elemental Analysis ① Calculated ② Found | | | $^1$H−NMR(ppm, CDCl$_3$) |
|---|---|---|---|---|---|---|
| | | | C | H | N | |
| 9-20 | 2-cyanobenzyloxy-tetrahydronaphthalene-spiro-piperidine N-propyl · HCl | (1) Noncrystalline powder (2) C$_{25}$H$_{31}$ClN$_2$O · 1/2H$_2$O | ① 71.50 ② 71.43 | 7.68 7.59 | 6.67 6.55 | 0.85(3H, t, J=7Hz), 1.33–1.98(10H, m), 2.20–2.49(2H, m), 2.56–2.80(6H, m), 5.09(2H, s), 6.67–6.77(2H, m) 7.00 (1H, d, J=8Hz), 7.54 (2H, d, J=8Hz), 7.68 (2H, d, J=8Hz) |

TABLE 30

| Example | Structural Formula | (1) Melting Point (°C.) or Physical Property (2) Molecular Formula | (3) Elemental Analysis ① Calculated ② Found | | | $^1$H−NMR(ppm, CDCl$_3$) |
|---|---|---|---|---|---|---|
| | | | C | H | N | |
| 9-21 | 4-fluorobenzyloxy derivative · HCl | (1) 176–181 (2) C$_{24}$H$_{31}$ClNOF · 1/4H$_2$O | ① 70.57 ② 70.45 | 7.77 7.64 | 3.43 3.45 | 0.86(3H, t, J=7Hz), 1.35–1.98(10H, m), 2.23–2.48(2H, m), 2.58–2.90(6H, m), 4.97 (2H, s, 6.67–6.77(2H, m), 6.98(1H, d, J=8Hz), 7.39(2H, dd, J=8Hz, 5Hz) |
| 9-22 | 2,4-dichlorobenzyloxy derivative · HCl | (1) 191–194 (2) C$_{20}$H$_{30}$Cl$_3$NO | ① 63.37 ② 63.03 | 6.65 6.66 | 3.08 3.15 | 0.86(3H, t, J=7Hz), 1.20–1.98(10H, m), 2.20–2.52(2H, m), 2.54–2.90(6H, m), 5.08(2H, s), 6.68–6.78(2H, m), 7.00(1H, d, J=8Hz), 7.29(1H, dd J=8Hz, 2Hz), 7.42(1H, d, J=2Hz), 7.50(1H, d, J=8Hz) |
| 9-23 | 2-methoxybenzyloxy derivative · HCl | (1) Noncrystalline powder (2) C$_{25}$H$_{34}$ClNO$_2$ · 1/2H$_2$O | ① 70.65 ② 70.97 | 8.30 8.33 | 3.30 3.24 | 0.85(3H, t, J=7Hz), 1.34–1.97(10H, m), 2.20–2.49(2H, m), 2.55–2.87(6H, m), 3.81(3H, s), 4.99(2H, s), 6.69–6.79(2H, m), 6.81–6.891(1H, m), 6.94–7.04(3H, m)), 7.19(1H, t, J=7Hz) |
| 9-24 | 2-trifluoromethylbenzyloxy derivative · HCl | (1) 174–178 (2) C$_{24}$H$_{31}$ClNO—F$_3$·1/4H$_2$O | ① 65.49 ② 65.74 | 6.93 6.83 | 3.06 3.21 | 0.85(3H, t, J=7Hz), 1.32–1.98(10H, m), 2.20–2.47(2H, m), 2.53–2.90(6H, m), 5.23(2H, s), 6.69–6.78(2H, m) 6.99(1H, d, J=8Hz), 7.41(1H, t, J=8Hz), 7.57(1H, t, J=8Hz), 7.69(1H, d, J=8Hz), 7.76(1H, d, J=8Hz) |

TABLE 31

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 9-25 | 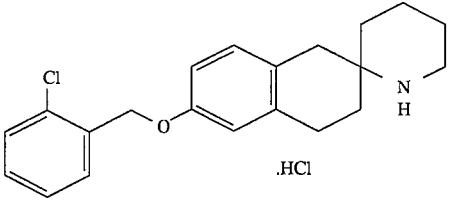 .HCl | (1) 217–222 (2) C$_{21}$H$_{25}$Cl$_2$NO· 1/4H$_2$O | ① 65.88 ② 66.03 | 6.71 6.74 | 3.66 3.58 | 1.42–1.99(9H, m), 2.65–2.97 (6H, m), 5.12 (2H, s), 6.72–6.81(2H, m), 6.99(1H, d, J=8Hz), 7.23–7.43(3H, m), 7.53–7.60 (1H, m) |
| 9-26 | 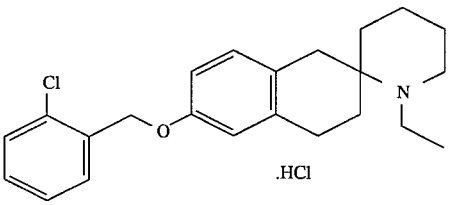 .HCl | (1) 181–185 (2) C$_{23}$H$_{29}$Cl$_2$NO· 1/2H$_2$O | ① 66.50 ② 66.87 | 7.28 7.12 | 3.37 3.35 | 1.07(3H, t, J=7Hz), 1.34–2.00(8H, m), 2.43–2.93 (8H, m), 5.13 (2H, s), 6.71–6.80(2H, m), 7.00(1H, d, J=8Hz), 7.15–7.43(3H, m), 7.53–7.60 (1H, m) |
| 9-27 | 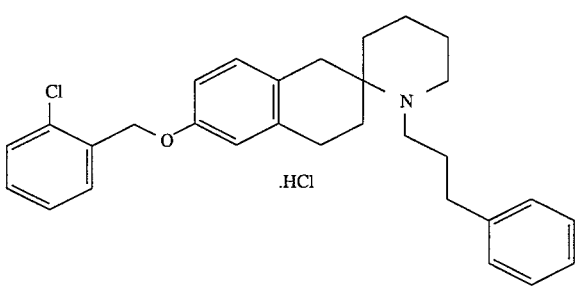 .HCl | (1) Noncrystalline powder (2) C$_{30}$H$_{35}$Cl$_2$NO· 3/4H$_2$O | ① 70.65 ② 70.41 | 7.25 7.18 | 2.72 2.61 | 1.34–1.94 (10H, m), 2.30–2.85 (10H, m), 5.11(2H, s), 6.68–6.78(2H, m), 6.95(1H, d, J=8Hz), 7.10–7.42(8H, m), 7.51–7.58 (1H, m) |
| 9-28 | 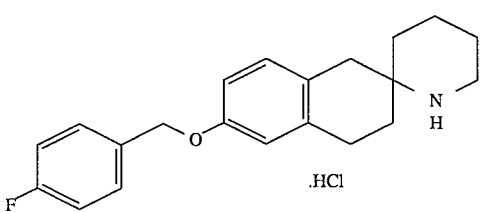 .HCl | (1) 191–194 (2) C$_{21}$H$_{25}$ClNOF· 1/4H$_2$O | ① 68.84 ② 68.52 | 7.02 6.96 | 3.82 3.66 | 1.43–2.00(9H, m), 2.71(2H, s), 2.74–2.91 (4H, m), 4.98 (2H, s), 6.69–6.78(2H, m), 6.94–7.13 (3H, m), 7.40 (2H, dd, J=8, 5Hz) |

TABLE 32

| Example | Structural Formula | (1) Melting Point (°C.) or Physical Property<br>(2) Molecular Formula | (3) Elemental Analysis<br>① Calculated<br>② Found | | | ¹H—NMR(ppm, CDCl₃) |
|---|---|---|---|---|---|---|
| | | | C | H | N | |
| 9-29 | 4-F-C₆H₄-CH₂-O-[tetrahydronaphthalene-spiro-piperidine]-N-pentyl · HCl | (1) 125–128<br>(2) $C_{26}H_{35}ClNOF \cdot \frac{1}{4}H_2O$ | ① 71.54<br>② 71.80 | 8.20<br>8.11 | 3.21<br>3.05 | 0.88(3H, t, J=7Hz), 1.10–1.98(14H, m), 2.23–2.51(2H, m), 2.51–2.89(6H, m), 4.98(2H, s), 6.67–6.78(2H, m), 6.94–7.14(3H, m), 7.40(2H, dd, J=9, 5Hz) |
| 9-30 | 4-F-C₆H₄-CH₂-O-[tetrahydronaphthalene-spiro-piperidine]-N-heptyl · HCl | (1) 122–124<br>(2) $C_{28}H_{39}ClNOF \cdot \frac{1}{4}H_2O$ | ① 72.39<br>② 72.43 | 8.57<br>8.46 | 3.01<br>2.93 | 0.87(3H, t, –J=7Hz), 1.17–1.98(18H, m), 2.26–2.50(2H, m), 2.56–2.90(6H, m), 4.97(2H, s), 6.67–6.77(2H, m), 6.93–7.12(3H, m), 7.39(2H, dd, J=9, 5Hz) |
| 9-31 | 4-F-C₆H₄-CH₂-O-[tetrahydronaphthalene-spiro-piperidine]-N-CH₂-C(=CH₂)-CH₃ · HCl | (1) Noncrystalline powder<br>(2) $C_{26}H_{35}ClNOF \cdot H_2O$ | ① 69.39<br>② 69.47 | 8.29<br>8.14 | 3.11<br>2.88 | 0.87(9H, s), 1.39–1.61(6H, m), 1.75(2H, t, J,=7Hz), 2.12(1H, J=14Hz), 2.14(1H, d, J=14Hz), 2.59–2.80(6H, m), 4.97(2H, s), 6.66–6.77(2H, m), 6.94–7.12(3H, m), 7.33–7.47(2H, m) |
| 9-32 | 4-F-C₆H₄-CH₂-O-[tetrahydronaphthalene-spiro-piperidine]-N-CH₂-C(=O)NH₂ · HCl | (1) 189–192<br>(2) $C_{23}H_{28}ClN_2O_2F \cdot \frac{3}{4}H_2O$ | ① 63.88<br>② 64.12 | 6.88<br>6.72 | 6.48<br>6.12 | 1.37–1.96(8H, m), 2.64–2.84(6H, m), 3.05(1H, d, J=17Hz), 3.17(1H, d, J=17Hz), 4.98(2H, s), 5.39(1H, br s), 6.68–6.78(2H, m), 6.94–7.13(3H, m), 7.30–7.47(1H, m), 7.35–7.44(2H, m) |
| 9-33 | 4-F-C₆H₄-CH₂-O-[tetrahydronaphthalene-spiro-piperidine]-N-CH₂-CN · HCl | (1) 169–175<br>(2) $C_{23}H_{26}ClN_2OF$ | ① 68.90<br>② 68.84 | 6.54<br>6.25 | 6.99<br>6.68 | 1.37–2.06(8H, m), 2.65–2.97(6H, m), 3.59(2H, s), 4.98(2H, s), 6.69–6.79(2H, m), 6.96–7.14(3H, m), 7.40(2H, dd, J=8, 5Hz) |

TABLE 33

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 9-34 | 4-F-C$_6$H$_4$-CH$_2$-O-tetralin-spiro-piperidine-N-CH$_2$CF$_3$ · HCl | (1) Noncrystalline powder (2) C$_{23}$H$_{26}$ClNOF$_4$· 1/4H$_2$O | ① 61.61 ② 61.84 | 5.96 5.77 | 3.12 3.30 | 1.37–1.92(8H, m), 2.55–3.08(8H, m), 4.98(2H, s), 6.68–6.78(2H, m), 6.87 (1H, d, J=8Hz), 7.06(2H, t, J=9Hz), 7.38(1H, d, J=9Hz), 7.41(1H, d, J=9Hz) |
| 9-35 | 4-F-C$_6$H$_4$-CH$_2$-O-tetralin-spiro-piperidine-N-CH$_2$C≡CH · HCl | (1) 182–185 (2) C$_{24}$H$_2$Cl$_7$NOF· 1/4H$_2$O | ① 71.27 ② 71.02 | 6.85 6.68 | 3.46 3.37 | 1.38–2.05(8H, m, 2.18(1H, t, J=3Hz), 2.63–3.02(6H, m), 3.41(2H, d, J=3Hz), 4.98(2H, s), 6.68–6.78(2H, m), 6.99(1H, d, J=9Hz, 7.08(1H, d, J=8Hz, 7.38(1H, d, J=9Hz), 7.41(1H, d, J=9Hz) |
| 9-36 | 4-F-C$_6$H$_4$-CH$_2$-O-(1-oxo-tetralin)-spiro-piperidine-N-propyl · HCl | (1) 138–142 (2) C$_{24}$H$_{29}$ClNO$_2$F· H$_2$O | ① 66.12 ② 66.33 | 7.17 7.15 | 3.21 2.97 | 0.80(3H, t, J=7Hz), 1.36–1.79(8H, m), 2.07–2.45(4H, m), 2.52–2.67(1H, m), 2.81–3.19(3H, m), 5.06(2H, s), 6.72(1H, d, J=3Hz), 6.88(1H, dd, J=9Hz), 7.38 (1H, d, J=9Hz), 7.41(1H, d, J=9Hz), 8.04(1H, d, J=9Hz) |
| 9-37 | 2-Cl-C$_6$H$_4$-CH$_2$-O-(1-oxo-tetralin)-spiro-piperidine-N-propyl · HCl | (1) 124–126 (2) C$_{24}$H$_{29}$Cl$_2$NO$_2$· H$_2$O | ① 63.72 ② 63.54 | 6.91 6.85 | 3.10 3.21 | 0.80(3H, t, J=7Hz), 1.34–1.84(8H, m, 2.08–2.45(4H, m), 2.51–2.67(1H, m), 2.81–3.18(2H, m), 5.20(2H, s), 6.75(1H, d, J=3Hz), 6.91(1H, dd, J=9, 3Hz), 7.17–7.46(3H, m), 7.49–7.56(1H, m), 8.05(1H, d, J=9Hz) |

TABLE 34

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 9-38 | 4-F-C$_6$H$_4$-CH$_2$-O-tetralin-spiro-piperidine-N-CH$_2$CH$_2$CN · HCl | (1) 194–200 (2) C$_{24}$H$_{28}$ClN$_2$OF· 1/4H$_2$O | ① 68.72 ② 68.58 | 6.85 6.93 | 6.68 6.48 | 1.35–1.93(8H, m), 2.37(2H, t, J=7Hz), 2.56–2.88(8H, m), 4.98(2H, s), 6.68–6.79(2H, m), 6.95–7.13(3H, m), 7.39(2H, dd, J=9, 6Hz) |

TABLE 34-continued

| Example | Structural Formula | (1) Melting Point (°C.) or Physical Property (2) Molecular Formula | (3) Elemental Analysis ① Calculated ② Found | | | ¹H—NMR (ppm, CDCl₃) |
|---|---|---|---|---|---|---|
| | | | C | H | N | |
| 9-39 | 4-fluorobenzyloxy-tetrahydronaphthalene spiro-piperidine N-(2-hydroxyethyl) · HCl | (1) 187–191 (decomposed) (2) $C_{23}H_{29}ClNO_2F \cdot 1/4H_2O$ | ① 67.31 ② 67.44 | 7.24 7.21 | 3.41 3.44 | 1.24–1.98(9H, m), 2.48–2.86(8H, m), 3.49(2H, t, J=7Hz), 4.97(2H, s), 6.68–6.78(2H, m), 6.98(1H, d, J=8Hz), 7.04(1H, d, J=9Hz), 7.08(1H, d, J=9Hz), 7.38(1H, d, J=9Hz), 7.40(1H, d, J=9Hz) |
| 9-40 | 4-fluorobenzyloxy-tetrahydronaphthalene spiro-piperidine N-[2-(4-(4-fluorophenyl)piperazin-1-yl)ethyl] | (1) 103–107 (2) $C_{33}H_{39}N_3OF_2$ | ① 74.55 ② 74.52 | 7.39 7.34 | 7.90 8.12 | 1.40–1.99(8H, m), 2.45–2.88(14H, m), 3.05–3.15(4H, m), 4.98(2H, s), 6.69–6.78(2H, m), 6.82–7.14(7H, m), 7.39(1H, d, J=9Hz), 7.42(1H, d, J=9Hz) |
| 9-41 | 4-fluorobenzyloxy-tetrahydronaphthalene spiro-piperidine N-[2-(imidazol-1-yl)ethyl] · 2HCl | (1) 225–228 (decomposed) (2) $C_{26}H_{32}Cl_2N_3OF \cdot H_2O$ | ① 61.18 ② 61.35 | 6.71 6.57 | 8.23 8.29 | 1.18–1.84(8H, m), 2.35–3.18(8H, m), 3.85(2H, t, J=6Hz), 4.96(2H, s), 6.62–6.79(2H, m), 6.84–6.93(2H, m), 7.02(1H, d, J=8Hz), 7.06(1H, d, J=8Hz), 7.20–7.44(3H, m), 7.55(1H, s) |

TABLE 35

| Example | Structural Formula | (1) Melting Point (°C.) or Physical Property (2) Molecular Formula | (3) Elemental Analysis ① Calculated ② Found | | | ¹H—NMR (ppm, CDCl₃) |
|---|---|---|---|---|---|---|
| | | | C | H | N | |
| 9-42 | 4-fluorobenzyloxy-tetrahydronaphthalene spiro-piperidine N-butyl · HCl | (1) 135–137 (2) $C_{25}H_{33}ClNOF \cdot 1/4H_2O$ | ① 71.07 ② 71.28 | 7.99 7.87 | 3.32 3.36 | 0.89(3H, t, J=7Hz), 1.17–1.98(12H, m), 2.24–2.50(2H, m), 2.56–2.88(6H, m), 4.98(2H, s), 6.67–6.78(2H, m), 6.98(1H, d, J=8Hz), 6.99–7.13(2H, m), 7.35–7.44(2H, m) |

TABLE 35-continued

| Example | Structural Formula | (1) Melting Point (°C.) or Physical Property (2) Molecular Formula | (3) Elemental Analysis ① Calculated ② Found | | | $^1$H—NMR (ppm, CDCl$_3$) |
|---|---|---|---|---|---|---|
| | | | C | H | N | |
| 9-43 | 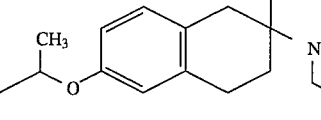 | (1) 166–171 (2) C$_{25}$H$_{34}$ClNO· 1/4H$_2$O | ① 74.23 ② 73.96 | 8.60 8.51 | 3.46 3.38 | 0.83(3H, t, J=7Hz), 1.24–1.94(10H, m), 1.60(3H, d, J=6Hz), 2.16–2.45(2H, m), 2.50–2.82(6H, m), 5.25(1H, q), 6.57–6.69(2H, m), 6.88(1H, d, J=9Hz), 7.13–7.42(5H, m) |
| 9-44 | 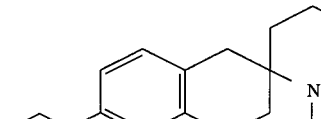 | (1) Noncrystalline powder (2) C$_{23}$H$_{32}$Cl$_2$N$_2$O· 3/2H$_2$O | ① 61.33 ② 61.35 | 7.83 8.12 | 6.22 5.94 | 0.85(3H, t, J=7Hz), 1.34–1.96(10H, m), 2.20–2.47(2H, m), 2.56–2.87(6H, m), 5.17(2H, s), 6.70–6.80(2H, m), 6.98(1H, d, J=8Hz), 7.14–7.31(1H, m), 7.52(1H, d, J=8Hz), 7.14–7.31(1H, m), 7.52(1H, d, J=8Hz), 7.71(1H, dt, J=8, 2Hz), 8.57–8.63(1H, m) |
| 9-45 |  | (1) 180–182 C$_{22}$H$_{30}$ClNOS· (2) 1/4H$_2$O | ① 66.64 ② 66.78 | 7.75 7.62 | 3.53 3.42 | 0.85(3H, t, J=7Hz), 1.35–1.98(10H, m), 2.21–2.48(2H, m), 2.56–2.88(6H, m), 5.02(2H, s), 6.68–6.78(2H, m), 6.98(1H, d, J=8Hz), 7.14(1H, dd, J=5, 2Hz), 7.29–7.36(2H, m) |
| 9-46 | 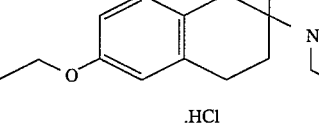 | (1) 153–158 (2) C$_{28}$H$_{34}$ClNO· 1/2H$_2$O | ① 75.57 ② 75.44 | 7.93 8.29 | 3.15 3.05 | 0.85(3H, t, J=7Hz), 1.34–1.99(10H, m), 2.20–2.48(2H, m), 2.58–2.88(6H, m), 5.19(2H, s), 6.74–6.84(2H, m), 6.99(1H, d, J=8Hz), 7.45–7.58(3H, m), 7.81–7.91(4H, m) |

TABLE 36

| Example | Structural Formula | (1) Melting Point (°C.) or Physical Property (2) Molecular Formula | (3) Elemental Analysis ① Calculated ② Found | | | ¹H—NMR(ppm, CDCl₃) |
|---|---|---|---|---|---|---|
| | | | C | H | N | |
| 9-47 | [naphthyl-CH₂-O-tetrahydronaphthalene-spiro-piperidine·HCl] | (1) 284–287(dec.) (2) C₂₅H₂₈ClNO· 1/4H₂O | ① 75.36 ② 75.40 | 7.21 7.21 | 3.52 3.47 | 1.40–1.76(8H, m), 1.82–1.97(1H, m), 2.69(2H, s), 2.74–2.88(4H, m), 5.18(2H, s), 6.74–6.84(2H, m), 6.98(1H, d, J=8Hz), 7.42–7.57(3H, m), 7.78–7.90(4H, m) |
| 9-48 | [naphthyl-CH₂-O-tetrahydronaphthalene-spiro-piperidine-N-CH₂CH(OH)CH₂-O-C₆H₄-F·HCl] | (1) Noncrystalline powder (2) C₃₅H₃₇ClNO₃F· H₂O | ① 70.99 ② 71.22 | 6.64 6.84 | 2.37 2.58 | 1.20–1.78(6H, m), 1.87–2.15(3H, m), 2.38–3.04(8H, m), 3.86–4.02(2H, m), 3.91(1H, d, J=8Hz), 5.18(2H, s), 6.74–7.02(7H, m), 7.43–7.56(3H, m), 7.78–7.90(4H, m) |
| 9-49 | [3,5-dimethylisoxazole-CH₂-O-tetrahydronaphthalene-spiro-piperidine-N-propyl·HCl] | (1) 149–151 (2) C₂₃H₃₃ClN₂O₂ | ① 68.21 ② 67.73 | 8.21 8.14 | 6.92 6.77 | 0.86(3H, t, J=7Hz), 1.35–1.99(10H, m), 2.21–2.48(2H, m), 2.28(3H, s), 2.39(3H, s), 2.58–2.88(6H, m), 4.74(2H, 2), 6.66–6.76(2H, m), 7.00(1H, d, J=8Hz) |
| 9-50 | [EtO-tetrahydronaphthalene-spiro-piperidine·HCl] | (1) Noncrystalline powder (2) C₁₆H₂₄ClNO· 1/4H₂O | ① 67.12 ② 67.37 | 8.62 8.47 | 4.89 4.82 | 1.39(3H, t, J=7Hz), 1.45–1.96(8H, m), 2.69(2H, s), 2.72–2.90(4H, m), 3.99(2H, q, J=7Hz), 6.64–6.70(2H, m), 6.96(1H, d, J=8Hz) |

TABLE 37

| Example | Structural Formula | (1) Melting Point (°C.) or Physical Property (2) Molecular Formula | (3) Elemental Analysis ① Calculated ② Found | | | ¹H—NMR (ppm, CDCl₃) |
|---|---|---|---|---|---|---|
| | | | C | H | N | |
| 9-51 | EtO-[structure]-N-CH₂-Ph .HCl | (1) Oil (2) $C_{25}H_{33}NO_2Cl$ | | | | 1.38–1.53(12H, m), 1.70–2.07(2H, m), 2.54–2.95(6H, m), 3.49–3.75(2H, m), 4.05(4H, q, J=8Hz), 6.59(1H, s), 6.61(1H, s), 7.20–7.38(5H, m) |
| 9-52 | EtO-[structure]-NH .HCl | (1) Noncrystalline powder (2) $C_{18}H_{28}ClNO_2$ | ① 66.34 ② 66.22 | 8.66 9.15 | 4.30 4.03 | |

EXAMPLE 10

7-Amino-3,4-dihydrospiro[naphthalene-2(1H),2'-piperidine]-1-one dihydrochloride

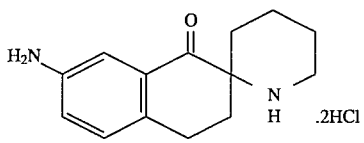

(1) To a solution of 4.0 g of 1'-trifluoroacetyl-3,4-dihydrospiro[naphthalene-2(1H),2'-piperidin]-1-one as obtained in Example 3-(1) in 10 ml of sulfuric acid, 6 ml of a 3:3 mixture of sulfuric acid and nitric acid was added drop by drop at 0° C., followed by stirring for 1.5 hours. Water was added; the reaction mixture was extracted with ethyl acetate. The ethyl acetate layer was dried over anhydrous magnesium sulfate and filtered, after which the solvent was distilled off. The resulting solid was recrystallized from ethyl acetate-hexane to yield 3.16 g of 1'-trifluoroacetyl-3,4-dihydro-7-nitrospiro[naphthalene-2(1H),2'-piperidine]-1-one as a colorless needle.

(2) To a solution of 3.0 g of 1'-trifluoroacetyl-3,4-dihydro-7-nitrospiro[naphthalene-2(1H),2'-piperidine]-1-one in 50 ml of ethanol, 0.30 g of 10% palladium-carbon catalyst and 2 ml of concentrate hydrochloric acid were added, followed by 3 hours of catalytic reduction at normal pressure and temperature. After the catalyst was filtered off, the filtrate was distilled to remove the solvent. The residue was dissolved in methylene chloride and washed with water. The methylene chloride layer was dried over anhydrous magnesium sulfate and filtered, after which the solvent was distilled off. The residue was treated with 2.2 ml of 4 N-methanolic hydrochloric acid to yield a solid, which was then recrystallized from ethanol-ether to yield 2.37 g of 7-amino-1'-trifluoroacetyl-3,4-dihydrospiro[naphthalene-2(1H),2'-piperidine]-1-one hydrochloride as a white crystal.

(3) 0.6 g of 7-amino-1'-trifluoroacetyl-3,4-dihydrospiro[naphthalene-2(1H),2'-piperidine]-1-one was dissolved in 10 ml of methanol. To this solution, 10 ml of a 1N solution of sodium hydroxide was added, followed by stirring at room temperature for 2 hours. Water was added; the reaction mixture was extracted with methylene chloride. The extract was dried over anhydrous sodium sulfate and filtered, after which the solvent was distilled off. The residue was treated with 0.5 ml of 4 N-methanolic hydrochloric acid to yield a solid, which was then recrystallized from methylene chloride-ethyl acetate to yield 0.42 g of the title compound as a white crystal. Melting point: 202°–204° C. (decomposed)

¹H-NMR (ppm, CDCl₃): 1.32–1.87 (7H, m), 1.87–2.10 (1H, m), 2.39 (1H, dt, J=14 Hz, 5 Hz), 2.76–2.94 (3H, m), 3.07 (1H, dt, J=14 Hz, 5 Hz), 3.69 (2H, br s), 6.83 (1H, dd, J=8 Hz, 2 Hz), 7.02 (1H, d, J=3 Hz), 7.29 (1H, d, J=3 Hz)

Elemental analysis (for $C_{14}H_{20}Cl_2N_2O$): Calculated: C, 55.45; H, 6.65; N, 9.24 Found: C, 55.13; H, 6.66; N, 9.18

EXAMPLE 11

3,4-Dihydro-7-(1-pyrrolidinyl)spiro[naphthalene-2(1H),2'-piperidine]-1-one dihydrochloride

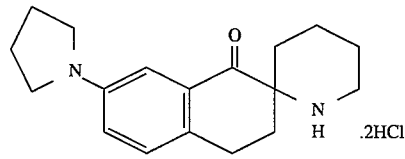

0.5 g of 7-amino-1'-trifluoroacetyl-3,4-dihydrospiro[naphthalene-2(1H),2'-piperidine]-1-one as obtained in Example 10-(2) was dissolved in 10 ml of N,N-dimethylformamide. To this solution, 0.76 g of potassium carbonate and 0.18 ml of 1,4-dibromobutane were added, followed by stirring at 70° C. for 24 hours. Water was added; the reaction mixture was extracted with ethyl acetate and washed with water and saturated saline. The extract was dried over anhydrous sodium sulfate and filtered, after which the solvent was distilled off. The residue was purified by silica gel column chromatography with ethyl acetate:hexane (1:1) as a developing solvent; the solution containing the desired product was distilled under reduced pressure. The residue was dissolved in 10 ml of methanol; 10 ml of a 1 N aqueous solution of sodium hydroxide was added, followed by stirring at room temperature for 12 hours. Water was added; the reaction mixture was extracted with methylene chloride. The extract was dried over anhydrous sodium sulfate and filtered, after which the solvent was distilled off. The residue was treated with 0.5 ml of 4N-methanolic hydrochloric acid to yield a solid, which was then recrystallized from ethanol-ethyl acetate to yield 0.24 g of a white crystal. Melting point: 170°–175° C.

$^1$H-NMR (ppm, CDCl$_3$): 1.39–2.08 (12H, m), 2.42 (1H, dt, J=14 Hz, 6 Hz), 2.78–2.97 (3H, m), 3.07 (1H, dt, J=14 Hz, 5 Hz), 3.24–3.37 (4H, m), 6.75 (1H, dd, J=8 Hz, 3 Hz), 7.07 (1H, d, J=8 Hz), 7.15 (1H, d, J=3 Hz)

Elemental analysis (for C$_{18}$H$_{26}$Cl$_2$N$_2$O.½H$_2$O): Calculated: C, 59.02; H, 7.43; N, 7.65 Found: C, 58.90; H, 6.94; N, 7.43

EXAMPLE 12

7-Acetylamino-3,4-dihydrospiro[naphthalene-2(1H),2'-piperidine] hydrochloride

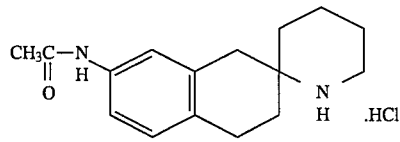

0.5 g of 7-amino-1'-trifluoroacetyl-3,4-dihydrospiro[naphthalene-2(1H),2'-piperidine]-1-one as obtained in Example 10-(2) was dissolved in 10 ml of methylene chloride. To this solution, 0.31 g of triethylamine was added; a solution of 0.19 ml of acetyl chloride in 5 ml of methylene chloride was added drop by drop at 0° C, followed by stirring at room temperature for 2 hours. Water was added; the reaction mixture was extracted with methylene chloride. The extract was dried over anhydrous sodium sulfate and filtered, after which the solvent was distilled off. The residue was treated in the same manner as in Example 3 to yield 0.09 g of the title compound as a white crystal.

Melting point: 158°–164° C.

$^1$H-NMR (ppm, CDCl$_3$): 1.40–2.05 (9H, m), 2.15 (3H, s), 2.69–2.82 (4H, m), 2.73 (2H, s), 7.03 (1H, d, J=8 Hz), 7.14–7.25 (3H, m)

Elemental analysis (for C$_{16}$H$_{23}$ClN$_2$O): Calculated: C, 65.18; H, 7.86; N, 9.50 Found: C, 64.96; H, 7.94; N, 9.61

EXAMPLE 13

7-Acetylamino-3,4-dihydro-1'-propylspiro[naphthalene-2(1H),2'-piperidine] hydrochloride

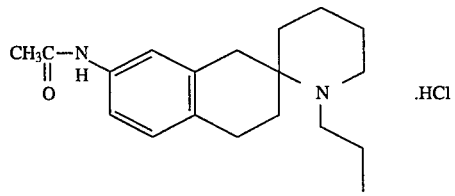

1.40 g of 7-acetylamino-3,4-dihydrospiro[naphthalene-2(1H),2'-piperidine] as obtained in Example 12 was treated in the same manner as in Example 5 to yield 1.45 g of the title compound as a white crystal.

Melting point: 253°–257° C. (decomposed)

$^1$H-NMR (ppm, CDCl$_3$): 0.85 (3H, t, J=7 Hz), 1.32–1.97 (10H, m), 2.15 (3H, s), 2.20–2.47 (2H, m), 2.59–2.97 (6H, m), 7.00 (1H, d, J=4 Hz), 7.10–7.28 (3H, m)

Elemental analysis (for C$_{19}$H$_{29}$ClN$_2$O.½H$_2$O): Calculated: C, 65.97; H, 8.74; N, 8.10 Found: C, 65.94; H, 8.65; N, 8.04

EXAMPLE 14

7-Amino-3,4-dihydro-1'-propylspiro[naphthalene-2(1H), 2'-piperidine] dihydrochloride

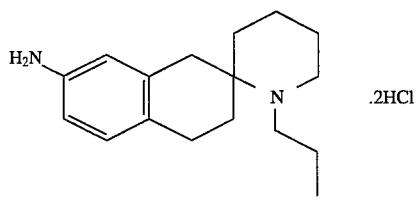

0.78 g of 7-acetylamino-3,4-dihydro-1'-propylspiro[naphthalene-2(1H),2'-piperidine] as obtained in Example 13 was dissolved in 15 ml of methanol. To this solution, 5 ml of a 10% aqueous solution of sodium hydroxide was added, followed by thermal refluxing for 24 hours. After the reaction mixture was allowed to cool, water was added; the reaction mixture was extracted with methylene chloride. The extract was dried over anhydrous sodium sulfate and filtered, after which the solvent was distilled off. The residue was treated with 0.6 ml of 4N-methanolic hydrochloric acid to yield a solid, which was then recrystallized from methanol-ethyl acetate to yield 0.59 g of a white crystal.

Melting point: 234°–238° C. (decomposed)

$^1$H-NMR (ppm, CDCl$_3$): 0.86 (3H, t, J=7 Hz), 1.36–1.94 (10H, m), 2.20–2.47 (2H, m), 2.52–2.87 (6H, m), 3.49 (2H, br s), 6.41–6.51 (2H, m), 8.87 (1H, d, J=8 Hz) Elemental analysis (for C$_{17}$H$_{28}$Cl$_2$N$_2$.½H$_2$O): Calculated: C, 60.00; H, 8.59; N, 8.23 Found: C, 60.17; H, 8.73; N, 8.05

EXAMPLE 15

7-Benzoylamino-3,4-dihydro-1'-propylspiro[naphthalene-2(1H), 2'-piperidine]

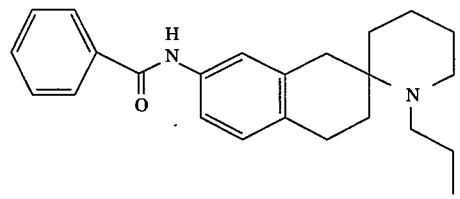

0.38 g of 7-amino-3,4-dihydro-1'-propylspiro[naphthalene-2(1H),2'-piperidine] as obtained in Example 14 was dissolved in 20 ml of methylene chloride. To this solution, 0.6 ml of triethylamine was added; a solution of 0.14 ml of benzoyl chloride in 10 ml of methylene chloride was added drop by drop at 0° C., followed by stirring at room temperature for 1 hour. Water was added; the reaction mixture was extracted with methylene chloride. The extract was dried over anhydrous sodium sulfate and filtered, after which the solvent was distilled off. The residue was purified by alumina column chromatography with ethyl acetate:hexane (1:4) as a developing solvent; the solution containing the desired product was distilled under reduced pressure. The residue was recrystallized from ethyl acetate-hexane to yield 0.30 g of a white crystal.

Melting point: 149°–151° C.

$^1$H-NMR (ppm, CDCl$_3$): 0.87 (3H, t, J=6 Hz), 1.33–2.01 (10H, m), 2.23–2.51 (2H, m), 2.58–2.97 (6H, m), 7.08 (1H, d, J=8 Hz), 7.24–7.37 (2H, m), 7.40–7.61 (3H, m), 7.72 (1H, br s), 7.87 (1H, d, J=8 Hz)

Elemental analysis (for C$_{24}$H$_{30}$N$_2$O.¼H$_2$O): Calculated: C, 78.54; H, 8.38; N, 7.63 Found: C, 78.76; H, 8.32; N, 7.72

EXAMPLE 16

3,4-Dihydro-7-phenylmethylaminospiro[naphthalene-2(1H),2'-piperidine] dihydrochloride

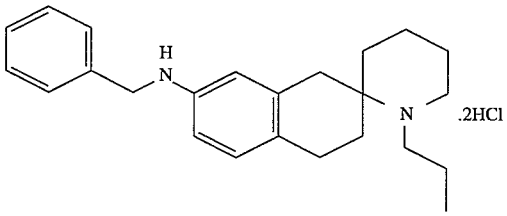

0.20 g of 7-benzoylamino-3,4-dihydro-1'-propylspiro[naphthalene-2(1H),2'-piperidine] as obtained in Example 15 was treated in the same manner as in Example 7 to yield 0.12 g of the title compound as a noncrystalline powder.

$^1$H-NMR (ppm, CDCl$_3$): 0.85 (3H, t, J=7 Hz), 1.32–1.95 (10H, m), 2.20–2.48 (3H, m), 2.53–2.89 (6H, m), 4.30 (2H, s), 6.37–6.48 (2H, m), 6.89 (1H, d, J=8 Hz), 7.14–7.44 (5H, m) Elemental analysis (for C$_{24}$H$_{34}$Cl$_2$N$_2$.½H$_2$O): Calculated: C, 66.97; H, 8.20; N, 6.51 Found: C, 67.24; H, 8.42; N, 6.51

EXAMPLE 17

3,4-Dihydro-1'-propyl-7-(2-pyrrolidon-1-yl)spiro[naphthalene-2(1H),2'-piperidine] hydrochloride

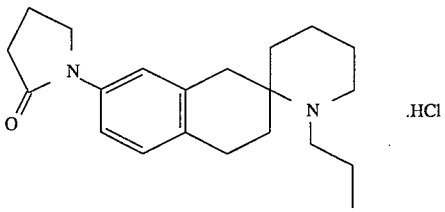

0.44 g of 7-amino-3,4-dihydro-1'-propylspiro[naphthalene-2(1H),2'-piperidine] as obtained in Example 14 was dissolved in 20 ml of methylene chloride. To this solution, 0.48 ml of triethylamine was added; a solution of 0.20 ml of 4-chlorobutyryl chloride in 10 ml of methylene chloride was added drop by drop at 0° C., followed by stirring at room temperature for 1 hour. Water was added; the reaction mixture was extracted with methylene chloride. The extract was dried over anhydrous sodium sulfate and filtered, after which the solvent was distilled off. The residue was dissolved in 10 ml of N,N-dimethylformamide; to this solution, 0.16 g of 60% sodium hydride was added, followed by stirring at room temperature for 4 hours. Water was added; the reaction mixture was extracted with ethyl acetate and washed with water and saturated saline. The extract was dried over anhydrous sodium sulfate and filtered, after which the solvent was distilled off. The residue was purified by alumina column chromatography with ethyl acetate:hexane (1:2) as a developing solvent; the solution containing the desired product was distilled under reduced pressure. The residue was treated with 0.5 ml of 4 N-methanolic hydrochloric acid to yield a solid, which was then recrystallized from ethanol-ethyl acetate to yield 0.21 g of a noncrystalline powder.

$^1$H-NMR (ppm, CDCl$_3$): 0.86 (3H, t, J=7 Hz), 1.34–1.98 (10H, m), 2.03–2.23 (2H, m), 2.24–2.48 (2H, m), 2.52–2.96 (8H, m), 3.74–3.93 (2H, m), 7.06 (1H, d, J=8 Hz), 7.23–7.35 (2H, m)

Elemental analysis (for C$_{21}$H$_{31}$ClN$_2$O.H$_2$O): Calculated: C, 66.21; H, 8.73; N, 7.35 Found: C, 66.54; H, 8.75; N, 7.41

EXAMPLE 18

3,4-Dihydro-7-(1-pyrrolidinyl)spiro[naphthalene-2(1H),2'-piperidine] dihydrochloride

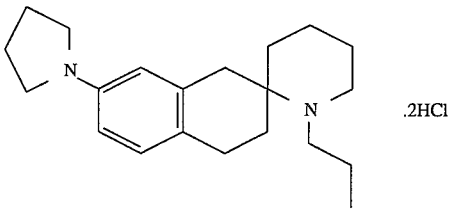

0.20 g of 3,4-dihydro-1'-propyl-7-(2-pyrrolidon-1-yl)spiro[naphthalene-2(1H),2'-piperidine] as obtained in Example 15 was treated in the same manner as in Example 7 to yield 0.07 g of the title compound as a noncrystalline powder.

$^1$H-NMR (ppm, CDCl$_3$): 0.86 (3H, t, J=7 Hz), 1.34–1.75 (9H, m), 1.78–2.04 (5H, m), 2.22–2.52 (2H, m), 2.60–2.94 (6H, m), 3.19–3.31 (4H, m), 6.30 (1H, br s), 6.39 (1H, dd, J=8 Hz, 2 Hz), 6.94 (1H, d, J=8 Hz)

Elemental analysis (for C$_{21}$H$_{34}$Cl$_2$N$_2$.¼C$_4$H$_8$O$_2$): Calculated: C, 64.85; H, 8.91; N, 6.88 Found: C, 64.99; H, 9.23; N, 6.79

EXAMPLE 19

5-Bromo-3,4-dihydrospiro[naphthalene-2(1H),2'-piperidine] hydrochloride

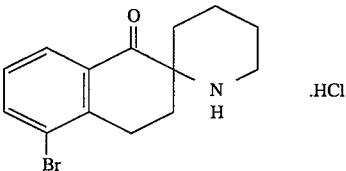

(1) 1.04 g of 1'-trifluoroacetyl-3,4-dihydrospiro[[naphthalene-2(1H),2'-piperidine]-1-one as obtained in Example 3-(1) was dissolved in 50 ml of 1,2-dichloroethane. To this solution, 0.18 ml of bromine and 1.44 g of aluminum chloride were added, followed by stirring at 60° C. for 3 hours. Water was added; the reaction mixture was extracted with methylene chloride. The extract was washed with a saturated aqueous solution of sodium hydrogen carbonate and an aqueous solution of sodium thiosulfate, dried over anhydrous sodium sulfate, and filtered, after which the solvent was distilled off. The residue was purified by silica gel column chromatography with ethyl acetate:hexane (1:2) as a developing solvent to yield 0.37 g of 5-bromo-1'-trifluoroacetyl-3,4-dihydrospiro[naphthalene-2(1H),2'-piperidine]-1-one and 0.72 g of 7-bromo-1'-trifluoroacetyl-3,4-dihydrospiro[naphthalene-2(1H),2'-piperidine]-1-one.

(2) 0.23 g of 5-bromo-1'-trifluoroacetyl-3,4-dihydrospiro[naphthalene-2(1H),2'-piperidine]-1-one as obtained in term (1) above was dissolved in 15 ml of methanol. To this solution, 3 ml of a 10% aqueous solution of sodium hydroxide was added, followed by stirring at room temperature for 2 hours. After the methanol was distilled off, water was added; the reaction mixture was extracted with ethyl acetate. The extract was dried over anhydrous sodium sulfate and filtered, after which the solvent was distilled off. The solution containing the desired product was distilled. The residue was treated with 0.2 ml of 4N-methanolic hydrochloric acid to yield a solid, which was then recrystallized from methanol-ethyl acetate to yield 0.17 g of a white crystal.

Melting point: 314°–316° C. (decomposed)

$^1$H-NMR (ppm, CDCl$_3$): 1.37–1.88, (7H, m), 1.94–2.11 (1H, m), 2.36–2.51 (1H, m), 2.77–3.18 (4H, m), 7.20 (1H, t, J=8 Hz), 7.73 (1H, dd, J=8 Hz, 1 Hz), 7.99 (1H, dd, J=8 Hz, 1 Hz)

Elemental analysis (for $C_{14}H_{17}BrClNO \cdot \frac{1}{4}H_2O$): Calculated: C, 50.17; H, 5.26; N, 4.18 Found: C, 50.18; H, 5.11; N, 4.19

EXAMPLE 20

7-Bromo-3,4-dihydrospiro[naphthalene-2(1H),2'-piperidine]-1-one hydrochloride

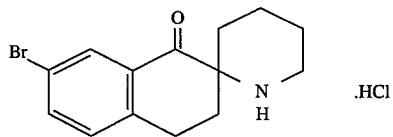

0.37 g of 7-bromo-1'-trifluoroacetyl-3,4-dihydrospiro[naphthalene-2(1H),2'-piperidine]-1-one as obtained in Example 19-(1) was treated in the same manner as in Example 17-(2) to yield 0.19 g of the title compound as a white crystal.

Melting point: 242°–245° C. (decomposed)

$^1$H-NMR (ppm, CDCl$_3$): 1.37–2.13 (8H, m), 2.34–2.48 (1H, m), 2.78–3.15 (4H, m), 7.11 (1H, d, J=8 Hz), 7.57 (1H, dd, J=8 Hz, 2 Hz), 8.35 (1H, d, J=2 Hz)

Elemental analysis (for $C_{14}H_{17}BrClNO$): Calculated: C, 51.86; H, 5.18; N, 4.24 Found: C, 52.14; H, 5.38; N, 4.24

EXAMPLE 21

1'-allyl-6-(4-fluoromethoxy)-3,4-dihydrospiro[naphthalene-2(1H),2'-piperidine] hydrochloride

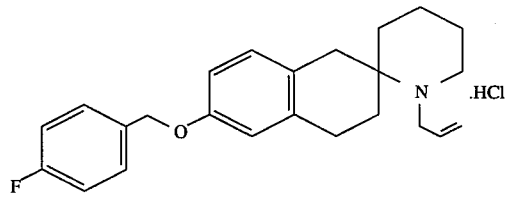

2.249 g of 3,4-dihydrospiro[naphthalene-2(1H),2'-piperidine] as obtained in Example 3-1 was dissolved in 30 ml of N,N-dimethylformamide. To this solution, 2.9 g of potassium carbonate and 0.88 ml of allyl bromide were added, followed by stirring at room temperature for 4 hours. Water was added; the reaction mixture was extracted with ethyl acetate and washed with water and saturated saline. The extract was dried over anhydrous sodium sulfate and filtered, after which the solvent was distilled off. The residue was purified by alumina column chromatography with ethyl acetate:hexane (1:4) as a developing solvent; the solution containing the desired product was distilled under reduced pressure. To the residue, 40 ml of 48% hydrobromic acid was added, followed by thermal refluxing for 2 hours. After the reaction mixture was neutralized by the addition of 10% sodium hydroxide, a dilute aqueous solution of potassium carbonate was added; the reaction mixture was extracted with methylene chloride. The extract was dried over anhydrous sodium sulfate and filtered, after which the solvent was distilled off. The residue was dissolved in 20 ml of N,N-dimethylformamide. To this solution, 0.50 g of 60% sodium hydride and 1.3 ml of p-fluorobenzyl bromide were added, followed by stirring at room temperature for 1 hour. Water was added; the reaction mixture was extracted with ethyl acetate and washed with water and saturated saline. The extract was dried over anhydrous sodium sulfate and filtered, after which the solvent was distilled off. The residue was purified by alumina column chromatography; the solution containing the desired product was distilled under reduced pressure; the residue was treated with 2.5 ml of 4 N-methanolic hydrochloric acid to yield 2.866 g of a white crystal.

Melting point: 167°–170° C. (decomposed)

$^1$H-NMR (ppm, CDCl$_3$): 1.42–2.00 (8H, m), 2.58–2.90 (6H, m), 2.96–3.22 (2H, s), 4.97 (2H, s), 5.01–5.21 (2H,m), 5.72–5.94 (1H, m), 6.68–6.78 (2H, m), 6.94–7.13 (3H, m), 7.34–7.45 (2H, m)

Elemental analysis (for $C_{24}H_{29}ClNOF \cdot \frac{1}{2}H_2O$): Calculated: C, 70.14; H, 7.36; N, 3.41 Found: C, 70.38; H, 7.26; N, 3.35

EXAMPLE 22

3,4-Dihydro-6-methoxy-7-nitrospiro[naphthalene-2(1H),2'-piperidine] hydrochloride

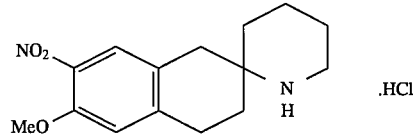

(1) After conversion into a free base, 5.0 g of 3,4-dihydro-6-methoxy-spiro[naphthalene-2(1H),2'-piperidine] hydrochloride as obtained in Example 4-1 was dissolved in 100 ml of methylene chloride. To this solution, 4.5 ml of pyridine and 5.2 ml of trifluoroacetic anhydride were added, followed by stirring at 0° C. for 1 hour and at room temperature for 2 hours. After water was added, the reaction mixture was extracted with methylene chloride; the methylene chloride layer was washed with dilute hydrochloric acid and dried over anhydrous sodium sulfate. After dry product filtration, the solvent was distilled off. The obtained residue was recrystallized from hexane to yield 5.2 g of 1'-trifluoroacetyl-3,4-dihydro-6-methoxyspiro[naphthalene-2(1H),2'-piperidine] as a white crystal.

Melting point: 75°–76° C.

$^1$H-NMR (δCDCl$_3$, free base): 1.63–1.81 (6H, m), 2.62–3.01 (5H, m), 3.56 (2H, t, J=5 Hz), 3.77 (3H, s), 3.84 (1H, d, J=15 Hz), 6.65–6.72 (2H, m), 6.98 (1H, d, J=8 Hz)

(2) 6.0 g of 1'-trifluoroacetyl-3,4-dihydro-6-methoxyspiro[naphthalene-2(1H),2'-piperidine] was dissolved in 150 ml of chloroform. After 1.5 g of ammonium nitrate was suspended in this solution, 9 ml of trifluoroacetic anhydride was added, followed by overnight stirring at room temperature. After water was added, the reaction mixture was extracted with methylene chloride. The extract was dried over anhydrous sodium sulfate and filtered, after which the solvent was distilled off. The residue was purified by silica gel column chromatography to yield 1.4 g of 1'-trifluoroacetyl-3,4-dihydro-6-methoxy-7-nitrospiro[naphthalene-2(1H),2'-piperidine] and 0.457 g of 1'-trifluoroacetyl-3,4-dihydro-6-methoxy-5-nitrospiro[naphthalene-2(1H),2'-piperidine].

1'-trifluoroacetyl-3,4-dihydro-6-methoxy-7-nitrospiro[naphthalene-2(1H),2'-piperidine]

Melting point: 105°–107° C.

$^1$H-NMR (δ, CDCl$_3$): 1.63–1.89 (7H, m), 2.65–3.15 (4H, m), 3.52–3.60 (2H, m), 3.83 (1H, d, J=15 Hz), 3.93 (3H, s), 6.83 (1H, s), 7.64 (1H, s)

Elemental analysis (for C$_{17}$H$_{19}$F$_3$N$_2$O$_4$) Calculated: C, 54.84; H, 5.14; N, 7.52 Found: C, 54.90; H, 5.15; N, 7.58

1'-trifluoroacetyl-3,4-dihydro-6-methoxy-5-nitrospiro[naphthalene-2(1H),2'-piperidine]

Melting point: 128°–130° C.

$^1$H-NMR (δ, CDCl$_3$): 1.57–1.81 (7H, m), 2.66–2.86 (4H, m), 3.50–3.64 (2H, m), 3.86 (3H, s), 3.96 (1H, d, J=16 Hz), 6.84 (1H, d, J=8 Hz), 7.13 (1H, d, J=8 Hz)

Elemental analysis (for C$_{17}$H$_{19}$F$_3$N$_2$O$_4$) Calculated: C, 54.84; H, 5.14; N, 7.52 Found: C, 54.71; H, 5.09; N, 7.55

(3) 0.5 g of 1'-trifluoroacetyl-3,4-dihydro-6-methoxy-7-nitrospiro[naphthalene-2(1H),2'-piperidine] as obtained in term (2) above was dissolved in 50 ml of methanol. To this solution, 0.221 g of potassium carbonate and 5 ml of water were added, followed by stirring at room temperature for 15 hours. After reaction mixture extraction with ethyl acetate, the extract was dried over anhydrous sodium sulfate and filtered, after which the solvent was distilled off. The residue was treated with a 4N hydrochloric acid-ethyl acetate solution to yield 3,4-dihydro-6-methoxy-7-nitrospiro[naphthalene-2(1H),2'-piperidine] hydrochloride as a noncrystalline powder.

$^1$H-NMR (δ, CDCl$_3$): 1.45–2.00 (8H, m), 2.73 (2H, s), 2.80–2.95 (4H, m), 3.91 (3H, s), 6.81 (1H, s), 7.63 (1H, s)

Elemental analysis (for C$_{15}$H$_{21}$ClN$_2$O$_3$H$_2$O) Calculated: C, 54.46; H, 7.01; N, 8.47 Found: C, 54.48; H, 6.58; N, 7.77

EXAMPLE 23

3,4-Dihydro-6-methoxy-5-nitrospiro[naphthalene-2(1H),2'-piperidine] hydrochloride

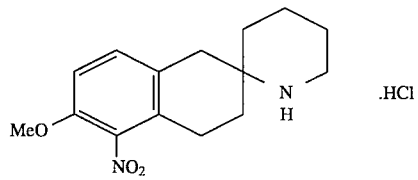

1'-trifluoroacetyl-3,4-dihydro-6-methoxy-5-nitrospiro[naphthalene-2(1H),2'-piperidine] as obtained in Example 22-(2) was treated in the same manner as in Example 22-(3) to yield the title compound as a noncrystalline powder.

$^1$H-NMR (δ, CDCl$_3$, free base): 1.44–1.75 (7H, m), 1.89–1.96 (1H, m), 2.71–2.84 (6H, m), 3.85 (3H, s), 6.83 (1H, d, J=9 Hz), 7.13 (1H, d, J=9 Hz)

Elemental analysis (for C$_{15}$H$_{21}$ClN$_2$O$_3$·¼H$_2$O) Calculated: C, 56.78; H, 6.83; N, 8.83 Found: C, 56.70; H, 6.74; N, 8.73

EXAMPLE 24

7-Acetyl-3,4-dihydro-6-methoxyspiro[naphthalene-2(1H),2'-piperidine]

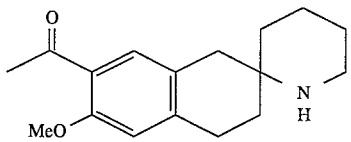

(1) 2.94 g of 1'-trifluoroacetyl-3,4-dihydro-6-methoxyspiro[naphthalene-2(1H),2'-piperidine] as obtained in Example 22-(1) was dissolved in 30 ml of carbon disulfide. To this solution, 0.85 ml of acetic anhydride was added under ice cooling conditions. After 2.4 g of aluminum chloride was added, the mixture was stirred at room temperature overnight. The reaction mixture was then added to ice water and extracted with ethyl acetate. The extracted was dried over anhydrous sodium sulfate and filtered, after which the solvent was distilled off. The residue was purified by silica gel column chromatography to yield a crude crystal, which was then recrystallized from ethyl acetate-hexane to yield 0.21 g of 7-acetyl-1'-trifluoroacetyl-3,4-dihydro-6-methoxyspiro[naphthalene-2(1H),2'-piperidine].

Melting point: 156°–157° C.

$^1$H-NMR (δ, CDCl$_3$): 1.63–1.85 (6H, m), 2.59 (3H, s), 2.65–3.10 (5H, m), 3.56 (2H, t, J=6 Hz), 3.76 (1H, d, J=13 Hz), 3.88 (3H, s), 6.71 (1H, s), 7.48 (1H, s)

Elemental analysis (for C$_{19}$H$_{22}$F$_3$NO$_3$) Calculated: C, 61.78; H, 6.00; N, 3.79 Found C, 61.64; H, 6.01; N, 3.95

(2) 0.15 g of 7-acetyl-1'-trifluoroacetyl-3,4-dihydro-6-methoxyspiro[naphthalene-2(1H),2'-piperidine] as obtained in Example 24-(1) was treated in the same manner as in Example 22-(3) to yield 0.096 g of the title compound as an oily substance.

$^1$H-NMR (δ, CDCl$_3$): 1.43–1.98 (8H, m), 2.59 (3H, s), 2.72 (2H, s), 2.80–2.95 (4H, m), 3.87 (3H, s), 6.70 (1H, s), 7.48 (1H, s)

EXAMPLE 25

(R)-(+)-3,4-Dihydro-6-methoxyspiro[naphthalene-2(1H),2'-piperidine] hydrochloride

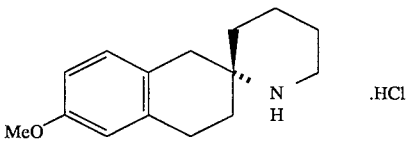

After conversion into a free base, 1 g of 3,4-dihydro-6-methoxy-spiro[naphthalene-2(1H),2'-piperidine] hydrochloride as obtained in Example 4-1 was dissolved in methanol. To this solution, a methanol solution of 0.867 g of (S)-(+)-10-camphorsulfonic acid was added, followed by concentration under reduced pressure. After the residue was dissolved in 10 ml of methanol, 20 ml of isopropyl ether was added; the mixture was kept standing at room temperature for 5 hours. The resulting crystal was collected by filtration and twice recrystallized from methanol-isopropyl ether to yield 0.2 g of a crystal. After conversion into a free base, this crystal was treated with a 4 N-hydrochloric acid-ethyl acetate solution to yield 0.1 g of (R)-(+)-3,4-dihydro-6-methoxyspiro[naphthalene-2(1H),2'-piperidine] hydrochloride as a white crystal. Optical purity was determined by high performance liquid chromatography using an optical isomer separation column (CHIRALCEL OB-H, produced by Daicel Chemical Industries, Ltd.).

Optical purity: Over 99.7% ee
Melting point: 152°–155° C.
Optical rotation: $[\alpha]_D^{27}=+3.44$

EXAMPLE 26

(S)-(−)-3,4-Dihydro-6-methoxyspiro[naphthalene-2(1H), 2'-piperidine] hydrochloride

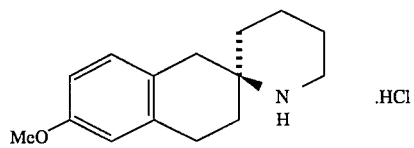

The mother liquors for recrystallization of the (+)-configuration in Example 25 were combined together and concentrated under reduced pressure. After conversion into a free base, the residue was dissolved in methanol. To this solution, a methanol solution of 0.7 g of (R)-(−)-10-camphorsulfonic acid was added, followed by concentration under reduced pressure. The residue was treated in the same manner as in Example 25 to yield 0.09 g of (S)-(−)-3,4-dihydro-6-methoxyspiro[naphthalene-2(1H),2'-piperidine] hydrochloride as a white crystal.

Optical purity: 97.1% ee
Melting point: 155°–160° C.

EXAMPLE 27

(+)-3,4-Dihydro-6,7-dimethoxyspiro[naphthalene-2(1H), 2'-piperidine]-1-one hydrochloride

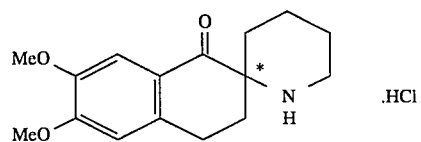

After conversion into a free base, 10 g of 3,4-dihydro-6, 7-dimethoxyspiro[naphthalene-2(1H),2'-piperidine]-1-one hydrochloride as obtained in Example 1-4 was dissolved in 700 ml of methanol. To this solution, 12.07 g of (2S,3S)-(+)-O,O'-dibenzoyltartaric acid monohydride was added. After the mixture was kept standing at room temperature for 3 days, the resulting crystal was collected by filtration. After conversion into a free base, this crystal was treated with a 4 N-hydrochloric acid-ethyl acetate solution to yield 1.84 g of (+)-3,4-dihydro-6,7-dimethoxyspiro[naphthalene-2(1H),2'-piperidine]-1-one hydrochloride as a white crystal.

Optical purity: Over 99.9% ee
Melting point: 251°–254° C.
Optical rotation: $[\alpha]_D^{26}=+41.22$

EXAMPLE 28

(−)-3,4-Dihydro-6,7-dimethoxyspiro[naphthalene-2(1H), 2'-piperidine]-1-one hydrochloride The mother liquors for recrystallization of the (+)-configuration in Example 27 were combined together and concentrated under reduced pressure. After conversion into a free base, the residue was dissolved in methanol. Using (2R,3R)-(−)-O,O'-dibenzoyltartaric acid monohydride, the solution was treated in the same manner as in Example 27 to yield 2.04 g of (−)-3,4-dihydro-6,7-dimethoxyspiro[naphthalene-2(1H),2'-piperidine]-1-one hydrochloride as a white crystal.

Optical purity: Over 99.9% ee
Melting point: 250°–252° C.
Optical rotation: $[\alpha]_D^{26}=-41.41$

EXAMPLE 29-1

(−)-3,4-Dihydro-6,7-dimethoxyspiro[naphthalene-2(1H), 2'-piperidine] hydrochloride (+)-3,4-dihydro-6,7-dimethoxyspiro[naphthalene-2(1H), 2'-piperidine]-1-one hydrochloride as obtained in Example 27 was treated in the same manner as in Examples 2

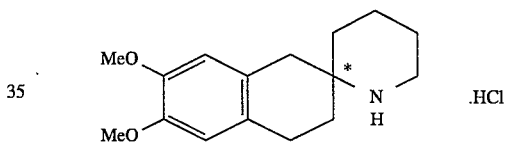

and 4 to yield (−)-3,4-dihydro-6,7-dimethoxyspiro[naphthalene-2 (1H), 2'-piperidine] hydrochloride.

Melting point: 165°–167° C.
Optical rotation: $[\alpha]_D^{26}=-1.92$

EXAMPLE 29-2

(+)-3,4-Dihydro-6,7-dimethoxyspiro[naphthalene-2(1H), 2'-piperidine] hydrochloride Melting point: 165°–167° C.
Optical rotation: $[\alpha]_D^{26}=+1.80$

EXAMPLE 30-1

(R)-(+)-1'-[2-4-(3-Trifluoromethylphenyl)piperazine-1-yl)ethyl]-3,4-dihydro-6-methoxyspiro[naphthalene-2(1H), 2'-piperidine] dihydrochloride

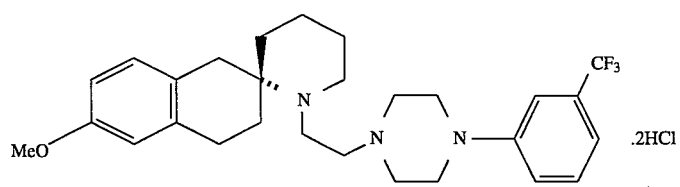

(−)-3,4-dihydro-6,7-dimethoxyspiro[naphthalene-2(1H), 2'-piperidine] hydrochloride as obtained in Example 29-1 was treated in the same manner as in Example 7 to yield (R)-(+)-1'-[2-4-(3-trifluoromethylphenyl)piperazine-1-yl)ethyl]-3,4-dihydro-6-methoxyspiro[naphthalene-2(1H),2'-piperidine] dihydrochloride.

Melting point: 195°–205° C. (decomposed)

Optical rotation: $[\alpha]_D^{26}=+7.49$

Elemental analysis (for $C_{28}H_{38}N_3OCl_2F_3 \cdot \frac{3}{4}H_2O$): Calculated: C, 58.59; H, 6.94; N, 7.32 Found: C, 58.62; H, 6.91; N, 7.17

EXAMPLE 30-2

(S)-(−)-1'-[2-4-(3-Trifluoromethylphenyl)piperazine-1-yl)ethyl]-3,4-dihydro-6-methoxyspiro[naphthalene-2(1H),2'-piperidine] dihydrochloride

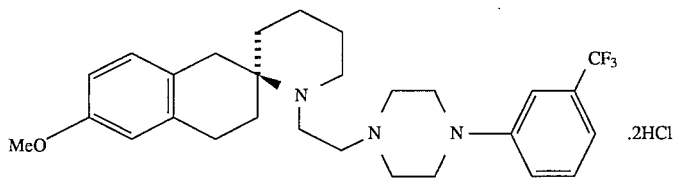

Melting point: 195°–205° C. (decomposed)

Optical rotation: $[\alpha]_D^{26}=-8.86$

Elemental analysis (for $C_{28}H_{38}N_3OCl_2F_3 \cdot \frac{3}{4}H_2O$): Calculated: C, 58.59; H, 6.94; N, 7.32 Found: C, 58.77; H, 6.76; N, 7.32

EXAMPLE 31-1

Spiro[tetralin-2,3'-morpholine] hydrochloride

To a solution of spiro[tetralin-2,3'-morpholine]-5'-one (22 mg, 0.1 mmol) in THF (2 ml), lithium aluminum hydride (12 mg, 0.3 mmol) was added, while the solution was stirred under ice cooling conditions. After cooling to room temperature, the mixture was stirred for 1 hour at constant temperature. After further stirring at 60° C. for 3 hours, a 1N aqueous sodium hydroxide solution was added; the precipitate was filtered out. The mother liquor was washed with saturated saline and dried over anhydrous sodium sulfate. The solvent was distilled off under reduced pressure. The obtained residue was subjected to silica gel column chromatography for elution with ethyl acetate-methanol (1:0–9:1). After concentration, the organic layer was dissolved in water-chloroform; the chloroform layer was dried and concentrated under reduced pressure. The obtained residue was dissolved in ethyl acetate. To this solution, a 4N hydrogen chloride-ethyl acetate solution was added. The mixture was concentrated under reduced pressure and crystallized with isopropyl ether to yield 12 mg (49%) of the title compound.

EXAMPLE 31-2

6-Methoxyspiro[tetralin-2,3'-morpholine] hydrochloride was synthesized in the same manner as in Example 31-1.

EXAMPLE 31-3

7-Methoxyspiro[tetralin-2,3'-morpholine] hydrochloride was synthesized in the same manner as in Example 31-1.

EXAMPLE 31-4

6,7-Dimethoxyspiro[tetralin-2,3'-morpholine] hydrochloride was synthesized in the same manner as in Example 31-1.

Table 38 and 39 show the structural formulas, physical properties and NMR spectra of these compounds.

TABLE 38

| Example | Structural Formula | Melting Point (°C.) or Physical Property | $^1$H-NMR(ppm, CDCl$_3$) |
|---|---|---|---|
| 31-1 | | 164–166 | δ: 1.70–1.90(2H, m), 1.91–2.05(1H, m), 2.70–2.93(4H, m), 2.94(2H, t, J=4.4Hz), 3.52(2H, s), 3.71(2H, t, J=4.8Hz), 7.00–7.12(4H, m) |
| 31-2 | | 212–215 | δ: 1.68–1.85(1H, m), 1.86–2.03(2H, m), 2.65–2.90(4H, m), 2.93(2H, t, J=4.6Hz), 3.51(2H, s), 3.71(2H, t, J=4.8Hz), 3.77(3H, s), 6.63–6.74(2H, m), 7.01(1H, d, J=8.4Hz) |

TABLE 39

| Example | Structural Formula | Melting Point (°C.) or Physical Property | ¹H–NMR(ppm, CDCl₃) |
|---|---|---|---|
| 31-3 | MeO-[tetralin]-spiro-morpholine·HCl | 230–235 | δ: 1.65–2.04(3H, m), 2.65–2.87(4H, m), 2.93(2H, t, J=5.6Hz), 3.51(2H, s), 3.70(2H, t, J=5.4Hz), 3.77(3H, s), 6.63(1H, d, J=2.6Hz), 6.72(1H, dd, J=8.2, 2.8Hz), 7.03(1H, d, J=8.2Hz) |
| 31-4 | MeO, MeO-[tetralin]-spiro-morpholine·HCl | 212–215 | δ: 1.68–1.84(1H, m), 1.85–2.07(2H, m), 2.63–2.90(4H, m), 2.95(2H, t, J=4.8Hz), 3.52(2H, s), 3.71(1H, t, J=5.2Hz), 3.84(6H, s), 6.56, 6.62(1H each, s) |

EXAMPLE 32-1

1'-Methylspiro[tetralin-2,3'-piperazine]

To a suspension of lithium aluminum hydride (114 mg, 3 mmol) and aluminum chloride (400 mg, 3 mmol) in ether (5 ml), a suspension of 1'-methylspiro[tetralin-2,3'-piperazine]-2',5'-dione (80 mg, 0.33 mmol) in ether (2 ml) was added, while the former was stirred under ice cooling conditions, followed by further stirring at room temperature for 10 minutes. After a 1N aqueous potassium hydroxide solution was added, the precipitate was filtered off. The filtrate was washed by sequential additions of a 1 N aqueous potassium hydroxide solution and chloroform. After the mother liquor was eluted with saturated saline, the organic layer was dried over anhydrous sodium sulfate. The solvent was distilled off under reduced pressure to yield the title compound (50 mg, 70%) as an oil.

EXAMPLE 32-2

6,7-Dimethoxy-1'-methylspiro[tetralin-2,3'-piperazine] dihydrochloride was synthesized in the same manner as in Example 32-1 and then dissolved in ethyl acetate. To this solution, a 4N hydrogen chloride-ethyl acetate solution was added. After mixture concentration under reduced pressure, isopropyl ether was added to yield the dihydrochloride as a powder.

EXAMPLE 32-3

1'-(4-Methoxyphenyl)-4'-methylspiro[tetralin-2,3'-piperazine]

1'-methylspiro[tetralin-2,3'-piperazine] (50 mg, 0.23 mmol) was dissolved in ethyl acetate (4 ml)-saturated aqueous potassium carbonate solution (4 ml). While the solution was vigorously stirred, p-methoxybenzoyl chloride (51 mg, 0.3 mmol) was added. After the organic layer was separated, the solvent was concentrated under reduced pressure. The obtained residue was subjected to silica gel column chromatography for elution with n-hexane-ethyl acetate (9:1) to yield 60 mg (74%) of the title compound as a crude crystal.

Table 40 shows the structural formulas, physical properties and NMR spectra of these compounds.

TABLE 40

| Example | Structural Formula | Melting Point (°C.) or Physical Property | ¹H–NMR(ppm, CDCl₃) |
|---|---|---|---|
| 32-1 | [tetralin]-spiro-piperazine (N-Me, NH) | oil | δ: 1.76–2.03(2H, m), 2.04–2.60(8H, m), 2.65–3.08(6H, m), 7.02–7.20(4H, m) |
| 32-2 | MeO, MeO-[tetralin]-spiro-piperazine (N-Me, NH)·2HCl | powder | δ: 1.70–2.00(2H, m), 2.15–2.60(8H, m), 2.62–3.10(6H, m), 3.83, 3.84(3H each, s), 6.57, 6.60(1H each, s) |

TABLE 40-continued

| Example | Structural Formula | Melting Point (°C.) or Physical Property | $^1$H–NMR(ppm, CDCl$_3$) |
|---|---|---|---|
| 32-3 | (structure shown) | 121–123 | δ: 1.60–1.80(1H, m), 2.18–2.43(6H, m), 2.43–2.58(1H, m), 2.67–2.88(2H, m), 3.00–3.22(2H, m), 3.40–3.70(3H, m), 3.83(3H, s), 6.87(2H, d, J=8.8Hz), 7.12(4H, s), 4.44(2H, d, J=8.8Hz) |

PREPARATION EXAMPLE 1

| (1) Compound of Example 9-21 | 10.0 g |
|---|---|
| (2) Lactose | 60.0 g |
| (3) Corn starch | 35.0 g |
| (4) Gelatin | 3.0 g |
| (5) Magnesium stearate | 2.0 g |

A mixture of 10.0 g of the compound of Example 9-21, 60.0 g of lactose and 35.0 g of corn starch was sieved through a 1 mm mesh sieve, using 30 ml of a 10% by weight aqueous solution of gelatin (containing 3.0 g of gelatin); the resulting granules were dried at 40° C. and again sieved. The obtained granules were mixed with 2.0 g of magnesium stearate and compressed. The resulting core tablets were sugar coated using an aqueous suspension of sucrose, titanium dioxide, talc and gum arabic, followed by glazing with beeswax to yield 1,000 coated tablets.

PREPARATION EXAMPLE 2

| (1) Compound of Example 9-21 | 10.0 g |
|---|---|
| (2) Lactose | 70.0 g |
| (3) Corn starch | 50.0 g |
| (4) Soluble starch | 7.0 g |
| (5) Magnesium stearate | 3.0 g |

A mixture of 10.0 g of the compound of Example 9-21 and 3.0 g of magnesium stearate was granulated using 70 ml of an aqueous solution of soluble starch (containing 7.0 g of soluble starch); the granules were dried and mixed with 70.0 g of lactose and 50.0 g of corn starch. The resulting mixture was compressed to yield 1,000 tablets.

EXPERIMENTAL EXAMPLE

Determination of monoamine uptake inhibitory activities

Serotonin (5-HT) Uptake inhibitory activity

Experiments were carried out in accordance with the method of Hyttel et al. [Psychopharmacology, Vol. 60, p. 13, 1978]. Whole rat brains were homogenized in a 40-fold volume of ice cooled 0.32M sucrose solution containing 10 μM pargyline, and centrifuged for 10 minutes (600×g). The supernatant was centrifuged for 55 minutes (2,500×g). The resulting sediment was suspended in a Krebs-Ringer phosphate buffer (pH 7.4, 122 mM NaCl, 4.82 mM KCl, 0.972 mM CaCl$_2$, 1.21 mM MgSO$_4$, 12.7 mM Na$_2$HPO$_4$, 2.97 mM NaH$_2$PO$_4$, 0.162 mM EDTA-sodium, 10 mM glucose, 1.14 mM ascorbic acid), previously saturated with a mixed gas (95% oxygen and 5% carbon dioxide). To 900 μl of this suspension, a DMSO solution (10 μl) of the test drug was added, followed by 5 minutes of incubation at 37° C. 100 μl (final concentration 10 nM) of 3H-5-HT was then added, followed by 5 minutes of incubation at 37° C. Subsequently, the reaction mixture was filtered through a GF/B filter under reduced pressure; the filter was washed with 4 ml of the above-mentioned buffer. The radioactivity on the filter was measured by the liquid scintillation method.

The amount of drug that caused a 5-HTk uptake reduction of 50% (50% inhibitory concentration, IC$_{50}$) is shown in Table 19.

Norepinephrine (NE) uptake inhibitory activity

Using rat cerebral cortex, with $^3$H-NE as substrate, the same procedure as for 5-HT was followed (Table 19).

Monoamine oxidase B (MAO-B) inhibitory activity

Whole rat brains were homogenized in a 10-fold volume of ice cooled 0.32 mM sucrose solution and diluted with a 10-fold volume of 10 mM phosphate buffer (pH 7.4). To 90 μl of this enzyme specimen, 1 μl of the test drug solution was added, followed by 10 minutes of incubation at 37° C. To the mixture, 10 μM of 14C-phenylethylamine was added, followed by 5 minutes of incubation at 37° C. After the reaction was stopped by the addition of 20 μl of 3M hydrochloric acid, 1 ml of water-saturated toluene-ethyl acetate (1:1) was added. The radioactivity of the metabolite migrated in the organic layer was measured by the liquid scintillation method. The drug concentration that caused an MAO-B activity reduction of 50% (IC$_{50}$) is shown in Table 2.

$^{45}$Ca$^{2+}$ uptake inhibition experiments

Rat cerebral cortex was homogenized with a 10-fold volume of 0.32M sucrose solution to yield a crude synaptosome fraction (100×g for 10 minutes, 12,000×g for 20 minutes). This fraction was homogenized in Tris buffer [neutralized with 132 mM sodium chloride, 5 mM potassium chloride, 1.3 mM magnesium chloride, 1.2 mM sodium dihydrogen phosphate, 1.2 mM calcium chloride, 10 mM glucose and 20 mM Tris base, saturated with a mixed gas (95% oxygen and 5% carbon dioxide)]. To 900 μl of this suspension, a DMSO solution (10 μl) of the test drug was added, followed by 10 minutes of incubation at 37° C. 100 μl (final concentration 30μM) of a veratrine solution (containing 0.18 μci $^{45}$Ca$^{2+}$) was then added, followed by 10 minutes of incubation at 37° C. Subsequently, the reaction mixture was quenched by the addition of 4 ml of an ice cooled EGTA solution (120 mM sodium chloride, 5 mM potassium chloride, 5 mM EGTA, pH 7.5), and subjected to aspiration filtration through a GF/B filter; the filter was washed with two 4 ml portions of a washing solution (132 mM sodium chloride, 5 mM potassium chloride, 1.3 mM magnesium chloride, 1.2 mM calcium chloride, 20 mM Tris base, pH 7.5). The radioactivity on the filter was measured by the liquid scintillation method. The results are shown in Table 21.

$^{45}Ca^{2+}$ uptake suppression rates were calculated as follows:

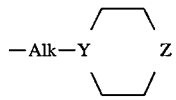

A: $^{45}Ca^{2+}$ uptake stimulated by 30 μM veratrine for 10 minutes in the presence of test drug B: $^{45}Ca^{2+}$ uptake in the absence of veratrine and in the presence of test drug C: $^{45}Ca^{2+}$ uptake stimulated by 30 μM veratrine for 10 minutes in the absence of test drug D: $^{45}Ca^{2+}$ uptake in the absence of veratrine and test drug

TABLE 19

| Example Number | Monoamine Uptake Inhibitory Activity (IC$_{50}$ in μM) | |
| --- | --- | --- |
| | 5-HT | NE |
| 5-10 | 0.0096 | 0.83 |
| 5-11 | 0.0045 | 0.50 |
| 5-14 | 0.011 | 0.18 |
| 7-1 | 0.022 | 4.77 |
| 7-5 | 0.03 | 3.35 |
| 9-7 | 0.70 | 0.059 |
| 9-8 | 0.18 | 0.035 |
| 9-9 | 0.28 | 0.062 |
| 9-19 | 0.80 | 0.09 |
| 9-20 | 0.32 | 0.054 |
| 9-21 | 0.34 | 0.097 |
| 9-22 | 0.19 | 0.067 |
| 30-2 | 0.0095 | 0.28 |

From Table 19, it is seen that desired compound (I) of the present invention or salt thereof exhibits excellent monoamine uptake inhibitory activity.

TABLE 20

| Example Number | $^{45}Ca$ Uptake Inhibitory Activity (% inhibition at 10 μM) |
| --- | --- |
| 5-9 | 92 |
| 5-10 | 88 |
| 5-14 | 74 |
| 7-1 | 90 |
| 7-3 | 95 |
| 7-5 | 87 |
| 7-6 | 106 |
| 7-9 | 109 |

From Table 20, it is seen that desired compound (I) of the present invention or salt thereof exhibits excellent Ca ion uptake inhibitory activity.

TABLE 21

| Example Number | MAO-B Inhibitory Activity (IC$_{50}$ in μM) |
| --- | --- |
| 9-1 | 0.28 |
| 9-6 | 2.51 |
| 9-7 | 1.63 |
| 9-16 | 0.59 |
| 9-18 | 1.49 |

TABLE 21-continued

| Example Number | MAO-B Inhibitory Activity (IC$_{50}$ in μM) |
| --- | --- |
| 9-19 | 0.89 |
| 9-21 | 0.68 |
| 9-23 | 2.83 |
| 9-32 | 0.53 |
| 9-45 | 0.060 |

From Table 21, it is seen that desired compound (I) of the present invention or salt thereof exhibits excellent MAO-B inhibitory activity.

What is claimed is:

1. A compound represented by the formula:

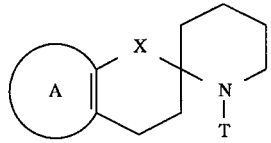

wherein
(a) ring A represents a benzene ring which may be substituted by 1 to 3 substituents independently selected from the group consisting of halogen atoms, a $C_{1-6}$ alkoxy group and a hydroxyl group; and T represents a group represented by the formula:

—Alk—Y⟨   ⟩Z wherein Alk represents a $C_{1-10}$ alkylene group which may be substituted by an oxo group; Y represents a nitrogen atom or —CH<; and Z represents an oxygen atom, >CH—(CH$_2$)$_q$—W or >N(CH$_2$)$_q$—W wherein q represents an integer from 0 to 4, and W represents a hydrogen atom or a $C_{6-14}$ aryl or 5- or 6-membered heterocyclic group containing 1 to 3 nitrogen, sulfur or oxygen hetero atoms independently selected from the group consisting of 2-thienyl, 3-thienyl, 2-pyridyl, 3-pyridyl, 4-pyridyl, 2-furyl, 3-furyl, 1-pyrrolidinyl, 2-pyrrolidinyl, 3-pyrrolidinyl, 1-piperazinyl and 2-piperazinyl, said aryl or heterocyclic group being optionally substituted with 1 to 3 substituents independently selected from the group consisting of (i) halogen atoms, (ii) a $C_{1-6}$ alkyl group, (iii) a $C_{3-8}$ cycloalkyl group, (iv) a $C_{1-6}$ alkoxy group, (v) a nitro group, (vi) a cyano group, (vii) a sulfonyl group, (viii) a hydroxyl group, (ix) an amino group, (x) a mono- or di-$C_{1-6}$ alkylamino group, (xi) a carbamoyl group, (xii) a mono- or di-$C_{1-6}$ alkylcarbamoyl group, (xiii) a phenyl group, (xiv) a benzyl group and (xv) a $C_{1-6}$ alkyl-carbonyl group; or (b) ring A represents a benzene ring substituted by 1 or 2 substituents independently selected from the group represented by the formula:

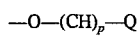

wherein p represents an integer from 0 to 4; and Q represents a $C_{6-14}$ aryl or 5- or 6-membered heterocyclic group containing 1 to 3 nitrogen, sulfur or oxygen hetero atoms independently selected from the group consisting of 2-thienyl, 3-thienyl, 2-pyridyl, 3-pyridyl, 4-pyridyl, 2-furyl, 3-furyl, 1-pyrrolidinyl, 2-pyrrolidinyl, 3-pyrrolidinyl, 1-piperazinyl and 2-piperazinyl, which may be substituted by 1 to 3 substituents independently selected from the group consisting of (i) a halogen atom, (ii) a $C_{1-6}$ alkyl group, (iii) a $C_{3-8}$ cycloalkyl group, (iv) a $C_{1-6}$ alkoxy group, (v) a nitro group, (vi) a cyano group, (vii) a sulfonyl group, (viii) a hydroxyl group, (ix) an amino group, (x) a mono- or di-$C_{1-6}$ alkylamino group, (xi) a carbamoyl group, (xii) a mono- or di-$C_{1-6}$ alkylcarbamoyl group, (xiii) a phenyl group, (xiv) a benzyl group and (xv) a $C_{1-6}$ alkyl-carbonyl group; and T represents a $C_{1-6}$ alkyl, $C_{2-10}$ alkenyl or $C_{2-10}$ alkynyl group; and X represents —$CH_2$—, —CO— or —CH(OH)—, or a pharmaceutically salt thereof.

2. A compound according to claim 1, which is (R)-(+)-1'-[2-4-(3-tri-fluoromethylphenyl)piperazine-1-yl)ethyl]-3,4-dihydro-6-methoxyspiro[naphthalene-2(1H),2'-piperidine] or a pharmaceutically acceptable salt thereof.

3. A compound as in claim 1, wherein Q is a phenyl group which may be substituted by 1 to 3 substituents independently selected from the group consisting of halogen atoms, a $C_{1-6}$ alkyl group and a $C_{1-6}$ alkoxy group.

4. A compound as in claim 1, wherein Z represents an oxygen atom, >CH—($CH_2$)—W or >N($CH_2$)$_q$—W wherein W is (i) a hydrogen atom or (ii) a phenyl group which may be substituted by 1 to 3 substituents independently selected from the group consisting of halogen atoms, a $C_{1-6}$ alkyl group and a $C_{1-6}$ alkoxy group.

5. A compound as in claim 1, wherein X is a methylene group.

6. A composition for treating a neuropathy which comprises an effective amount of a compound as claimed in claim 1 and a pharmaceutically acceptable carrier.

7. A composition for treating a dysmnesia which comprises an effective amount of a compound as claimed in claim 1 and a pharmaceutically acceptable carrier.

8. A composition for inhibiting a monoamine uptake which comprises an effective amount of a compound as claimed in claim 1 and a pharmaceutically acceptable carrier.

9. A composition for inhibiting a calcium ion uptake which comprises an effective amount of a compound as claimed in claim 1 and a pharmaceutically acceptable carrier.

10. A composition for inhibiting a monoamine-oxidase B which comprises an effective amount of a compound as claimed in claim 1 and a pharmaceutically acceptable carrier.

* * * * *

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

On the title page, and in column 1, line 2:
[54] TITLE

"SPIRO[NAPHTHALENE-2(1H),2'-PIPERIDINE] AND THEIR USE"
should read --SPIRO[NAPHTHALENE-2(1H),2'-PIPERIDINE]
COMPOUNDS AND THEIR USE--.

[57 ABSTRACT]

Line 11, "a" should be deleted.

COLUMN 1

Line 2, "AND" should read --COMPOUNDS AND--.
Line 4, "BACK GROUND" should read --BACKGROUND--.
Line 11, "relate" should read --relates-- and
"producting" should read --producing--.

COLUMN 2

Line 19, "$CH_2$-," should read -- -$CH_2$-, --.

COLUMN 3

Line 59, "| $T^©$ " should read --| $T^1$ --.

COLUMN 4

Line 25, "alomatic" should read --aromatic--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 6

Line 20, "group" (first occurrence) should read
      --groups--.

COLUMN 8

Line 16, "heteroyclic" should read --heterocyclic--.

COLUMN 9

Line 16, Phenyl" should read --a phenyl--.
    Line 30, "propyonylamino," should read
      --propionylamino,--.

COLUMN 10

Line 32, "followings:" should read --the following:--.
    Line 49, "defined" should read --defined by--.
    Line 58, "groups" should read --group--.

COLUMN 11

Line 41, "goroup" " should read --group"--.
    Line 42, "defined" should read --defined by--.
    Line 66, ">CH1' $(CH_2)_q$-W" should read -->CH-$(CH_2)_q$-W--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 12

Line 27, "alkinyl" should read --alkynyl--.
    Line 56, "1 "D" " should read --1, "D"--.

COLUMN 13

Line 2, "10" should be deleted.
    Line 4, "ring B" should read --"ring B"--.
    Line 6, "have Spe-" should read --have. Spe- --.
    Line 18, "grous," should read --group,--.
    Line 19, "a amino" should read --an amino--.
    Line 21, "groups" should read --group--.
    Line 52, "-(CH$_2$)2-" should read -- -(CH$_2$)$_2$- --.

COLUMN 14

Line 6, "preferred. (C)" should read --preferred. ¶(C)--.
    Line 7, "ring A" should read --"ring A"--.
    Line 66, "an" should be deleted.

COLUMN 16

Line 51, "Cyclization 1̂" should read --Cyclization 3̂--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 17

Line 1, "Hydrolysis ②" should read --Hydrolysis ②--.
Line 42, "nyldimetylsilane)" should read
--nyldimethylsilane)--.
Line 56, "reaction ③," should read --reaction ③,--.

COLUMN 19

Line 47, "With" should read --with-- and "16" should read --10--.

COLUMN 20

Line 14, "-16°" should read -- -10°--.
Line 34, "\\ should read --\\
        $T^{©}$"                $T'$ --.
Line 41, "\\ should read --\\
        $T^{©}$"                $T'$ --.
Line 48, "\\ should read --\\
        $T^{©}$"                $T'$ --.
Line 56, "\\ should read --\\
        $T^{©}$"                $T'$ --.
Line 64, "\\ should read --\\
        $T^{©}$"                $T'$ --.

UNITED STATES PATENT AND TRADEMARK OFFICE
CERTIFICATE OF CORRECTION

PATENT NO. : 5,591,849

DATED : January 7, 1997

INVENTOR(S) : KANEYOSHI KATO ET AL.

It is certified that error appears in the above-identified patent and that said Letters Patent is hereby corrected as shown below:

COLUMN 21

Line 10, "$\setminus_{T^{©}}$" should read --$\setminus_{T'}$--.
Line 18, "$\setminus_{T^{©}}$" should read --$\setminus_{T'}$--.
Line 31, "130°C." should read --130°C.,--.
Line 52, "100°C." should read --100°C.,--.
Line 54, "time" (first occurrence) should read --temperature--.
Line 63, "$\setminus_{T^{©}}$" should read --$\setminus_{T'}$--.

COLUMN 22

Line 8, "$\setminus_{T^{©}}$" should read --$\setminus_{T'}$--.
Line 14, "$\setminus_{T^{©}}$" should read --$\setminus_{T'}$--.
Line 23, "C." should read --C.,--.
Line 31, "Louis" should read --Lewis--.

COLUMN 24

Line 40, "examples," should read --example,--.
Line 49, "a" should read --an--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 27

Line 1, "Table 1" should read --Tables 1--.
　Table 1, under "Reference Example 1-4", "J=5, 4Hz),"
　　should read --J=5.4 Hz),-- and "J=5, 2Hz),"
　　should read --J=5.2 Hz),--.

COLUMN 31

Line 17, "-morpholine-5'-one]" should read
　　--morpholine]-5'-one--.
　Line 25, "wager" should read --water--.

COLUMN 34

Table 5, under "Reference Example 4-2", "2.00-2.16(1H, m,"
　　should read --2.00-2.16(1H, m),--.
　Line 50, "in" should read --in Reference Example 5-1.--.
　Line 53, "REFERENCE EXAMPLE 5-1." should be deleted.

COLUMN 36

Table 7, under "Reference Example 6-1", ".1.99" should
　　read --1.99-- and "$\Delta\upsilon$=29,8Hz)," should read
　　--$\Delta\upsilon$=29.8Hz),--.

COLUMN 38

Line 19, "Table 8" should read --Tables 8--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 39

Line 47, "quint," should read --quint, J=7Hz),
　　　2.74-2.94 (4H, m), 4.37 (1H,--.

COLUMN 40

Line 24, "(4H, J=7Hz), 2.74-2.94 (4H, m), 4.37 (1H,"
　　　should read --(4H,--.

COLUMN 42

Line 49, "2'(1H)naphthalene]" should read --2'(1H)-
　　　naphthalene]--.

COLUMN 43

Line 31, "TO" should read --To--.

COLUMN 44

Line 21, "$C_{15}H_{22}ClNo.+e,fra/5+ee\ H_2O):$" should read
　　　--$C_{15}H_{22}ClNO\cdot1/5H_2O):$--.

COLUMN 45

Line 38, "of," should read --of--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 46

Line 25, "[naphthalene(1H)," should read
--[naphthalene-2(1H),--.
Line 29, "-1-" should read -- -1'- --.
Line 44, "lene-(1H)," should read --lene-2(1H),--.
Line 48, "thalene-(1H)," should read --thalene-2(1H),--.
Line 53, "thalene-(1H)," should read --thalene-2(1H),--.

COLUMN 47

Line 3, "4yl)" should read --4-yl)--.
Line 9, "thalene-(1H)," should read --thalene-2(1H),--.
Line 13, "(1H)," should read --2(1H),--.
Line 30, "(3,3diphenylpropyl)" should read
--(3,3-diphenylpropyl)--.
Line 35, "(3,3diphenylpropyl)" should read
--(3,3-diphenylpropyl)--.

COLUMN 51

Table 15, under "Example 5-13", "(2) $C_{17}H_{25}ClNO_2O_2$" should read --(2) $C_{17}H_{25}ClN_2O_2$--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 55

Table 17, under "Example 5-21", "212-246" should read --2.12-2.46--.

COLUMN 57

Table 18, under "Example 5-24", "274.48" should read --278.48--.

COLUMN 61

Line 1, "[naphthalene-(1H)," should read --[naphthalene-2(1H),--.

COLUMN 62

Table 20, "(docomposed)" should read --decomposed--.
Line 39, "($C_{28}H_{41}C_{12}N_3O_2 \cdot 2H_2O$):" should read --($C_{28}H_{41}Cl_2N_3O_2 \cdot 2H_2O$):--.
Line 43, "EXAMPLE 7-1 described" should read --Example 7-1 described--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 64

Line 18, "2'-piperidine]hy-" should read --2'-piperidine] 2hy- --.
Line 23, "hydro-" should read --3 hydro- --.

COLUMN 65

Table 21, under "Example 7-6", "$N_2O \cdot H_2O$" should read --$N_3O \cdot H_2O$--.

COLUMN 71

Line 16, "4 8%" should read --48%--.

COLUMN 72

Line 18, "(1H)," should read --2(1H),--.
Line 23, "thalene-(1H)," should read --thalene-2(1H),--.

COLUMN 75

Line 60, "(2-pro" should read --(2-pro- --.

COLUMN 76

Line 24, "(limida-" should read --(1-imida- --.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 79

Table 27, under "Example 9-8", "7.29(1H,s), 7.30(2H,s)," should read --7.26(2H,s), 7.35(2H,s)--.

COLUMN 85

Table 30, under "Example 9-21", "(2H,s," should read --(2H,s),--; under "Example 9-22", "3.15" should read --3.16--; and under "Example 9-23", "6.891" should read --6.89--.

COLUMN 91

Table 33, under "Example 9-35", "$C_{24}H_2Cl_7NOF$." should read --$C_{28}4_{38}ClNOF$.--; "(8H,m," should read --(8H,m),--; "J=9Hz," should read --J=9Hz),--; and "J=8Hz," should read --J=8Hz),--; under "Example 9-36", "dd,J=9Hz)," should read --dd,J=9.3Hz), 7.06(1H,d,J=8Hz), 7.10(1H,d,J=9Hz),--; and under "Example 9-37", "(8H,m," should read --(8H,m),-- and "(2H,m)," should read --(3H,m), and Table 33, under Example 9-37, "3.21" should read -- 3.29--.

COLUMN 97

Table 36, under "Example 9-49", "(2H, 2)," should read --(2H, s),--

COLUMN 102

Line 37, "Elemental" should read -- ¶ Elemental--.

UNITED STATES PATENT AND TRADEMARK OFFICE
CERTIFICATE OF CORRECTION

PATENT NO. : 5,591,849

DATED : January 7, 1997

INVENTOR(S) : KANEYOSHI KATO ET AL.

Page 12 of 15

It is certified that error appears in the above-identified patent and that said Letters Patent is hereby corrected as shown below:

COLUMN 103

Line 32, "Elemental" should read --¶ Elemental--.

COLUMN 104

Line 54, "[[naphtha-" should read --[naphtha- --.

COLUMN 106

Line 64, "(δCDCl$_3$," should read --(δ, CDCl$_3$,--.

COLUMN 107

Line 17, close up right margin.
Line 46, "C$_{15}$H$_{21}$ClN$_2$O$_3$,H$_2$O)" should read
--C$_{15}$H$_{21}$ClN$_2$O$_3$.H$_2$O)--.

COLUMN 108

Line 23, "extracted was" should read --extract was--.

COLUMN 109

Line 30, "(S)-(-)3,4-" should read --(S)-(-)-3,4- --.

COLUMN 111

Line 6, "C$_{28}$H$_{38}$N$_3$OC$_{12}$F$_3$·¾H$_2$O):" should read
--C$_{28}$H$_{38}$N$_3$OCl$_2$F$_3$·¾H$_2$O):--.

UNITED STATES PATENT AND TRADEMARK OFFICE
CERTIFICATE OF CORRECTION

PATENT NO. : 5,591,849
DATED : January 7, 1997
INVENTOR(S): KANEYOSHI KATO ET AL.

It is certified that error appears in the above-identified patent and that said Letters Patent is hereby corrected as shown below:

COLUMN 112

Line 37, "Table 38" should read --Tables 38--.

COLUMN 115

Line 55, "Uptake" should read --uptake--.

COLUMN 116

Line 20, "3H-5-HT" should read --$^3$H-5-HT--.
Line 32, "(Table 19)." should read --(Table 41).--.
Line 39, "14C-phenylethylamine" should read --$^{14}$C-phenylethylamine--.
Line 46, "Table 2." should read --Table 43.--.

COLUMN 117

Line 5, "Table 21." should read --Table 42.--.
Line 12, "$^{45}$Ca$^{2+}$" should read --A: $^{45}$Ca$^{2+}$--.
Line 16, "$^{45}$Ca$^2$+" should read --$^{45}$Ca$^{2+}$--.
Line 19, "$^{45}$Ca$^2$+" should read --$^{45}$Ca$^{2+}$--.
Line 21, "TABLE 19" should read "TABLE 41--.
Line 39, "Table 19," should read --Table 41,--.
Line 43, "TABLE 20" should read --TABLE 42--.
Line 55, "Table 20," should read --Table 42,--.
Line 59, "TABLE 21" should read --TABLE 43--.

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

COLUMN 118

```
Line 2,  "TABLE 21" should read --TABLE 43--.
Line 11, "Table 21," should read --Table 43,--.
Line 61, "-O-(CH)_p-Q" should read -- -O-(CH_2)_p-Q--.
```

UNITED STATES PATENT AND TRADEMARK OFFICE
CERTIFICATE OF CORRECTION

PATENT NO. : 5,591,849

DATED : January 7, 1997

INVENTOR(S): KANEYOSHI KATO ET AL.

It is certified that error appears in the above-identified patent and that said Letters Patent is hereby corrected as shown below:

<u>COLUMN 119</u>

Line 13, "$C_{1-6}$ alkyl," should read --$C_{1-10}$ alkyl,--.
Line 16, "pharmaceutically" should read
    --pharmaceutically acceptable--.
Line 18, "tri-fluoromethylphenyl)" should read
    --trifluoromethylphenyl)--.

Signed and Sealed this

Sixteenth Day of September, 1997

Attest:

BRUCE LEHMAN

*Attesting Officer*     *Commissioner of Patents and Trademarks*